(12) United States Patent
Davis et al.

(10) Patent No.: US 10,549,005 B2
(45) Date of Patent: Feb. 4, 2020

(54) ADVANCED SCENT DISPERSION DEVICE

(71) Applicants: Darin Davis, Lindon, UT (US); Glenn Jakins, Provo, UT (US); Darrell Jakins, Provo, UT (US); Haruyoshi Miyagi, Highland, UT (US)

(72) Inventors: Darin Davis, Lindon, UT (US); Glenn Jakins, Provo, UT (US); Darrell Jakins, Provo, UT (US); Haruyoshi Miyagi, Highland, UT (US)

( * ) Notice: Subject to any disclaimer, the term of this patent is extended or adjusted under 35 U.S.C. 154(b) by 142 days.

(21) Appl. No.: 15/863,820

(22) Filed: Jan. 5, 2018

(65) Prior Publication Data

US 2018/0154036 A1    Jun. 7, 2018

Related U.S. Application Data

(63) Continuation-in-part of application No. 15/622,058, filed on Jun. 13, 2017.

(60) Provisional application No. 62/442,561, filed on Jan. 5, 2017, provisional application No. 62/442,558, filed on Jan. 5, 2017, provisional application No. 62/350,696, filed on Jun. 15, 2016.

(51) Int. Cl.
*A61L 9/12*         (2006.01)
*B01F 3/04*         (2006.01)

(52) U.S. Cl.
CPC ............... *A61L 9/127* (2013.01); *A61L 9/122* (2013.01); *B01F 3/04* (2013.01); *A61L 2209/111* (2013.01); *A61L 2209/12* (2013.01); *A61L 2209/133* (2013.01); *A61L 2209/15* (2013.01)

(58) Field of Classification Search
CPC .................................. A61L 9/127; B01F 3/04
See application file for complete search history.

(56) References Cited

U.S. PATENT DOCUMENTS

| | | | |
|---|---|---|---|
| 9,486,822 B2 * | 11/2016 | Johnson | A61L 9/127 |
| 9,586,228 B2 * | 3/2017 | Roemburg | A61L 9/127 |
| 2010/0284783 A1 | 11/2010 | Lolmede | |
| 2012/0079945 A1 | 4/2012 | Roberts | |
| 2014/0145005 A1 | 5/2014 | Westphal | |
| 2014/0334129 A1 | 11/2014 | McCavit et al. | |
| 2015/0273099 A1 | 10/2015 | Habbel | |
| 2016/0089466 A1 | 3/2016 | McMinn et al. | |
| 2017/0360980 A1 | 12/2017 | Jakins et al. | |

FOREIGN PATENT DOCUMENTS

WO    2016205836 A1    12/2016

* cited by examiner

*Primary Examiner* — Robert A Hopkins
(74) *Attorney, Agent, or Firm* — Amy Fiene; James Sonntag

(57) ABSTRACT

A scent delivery system includes a housing that releases a volatile substance from a porous body into the air. The housing may be part of a scent dispersion device that includes volatilization as directed by a fan and a controller within the housing.

20 Claims, 54 Drawing Sheets

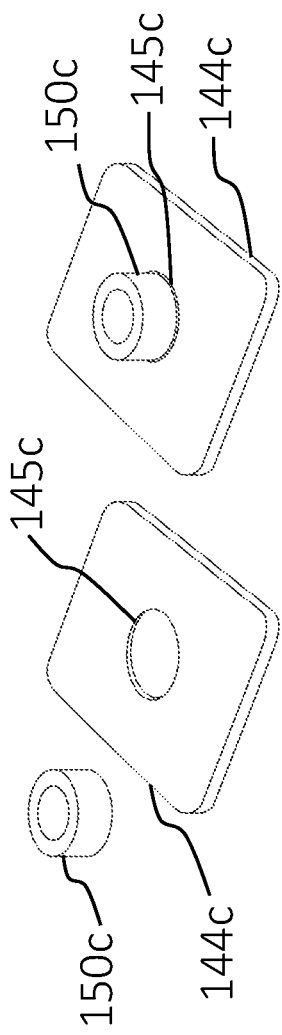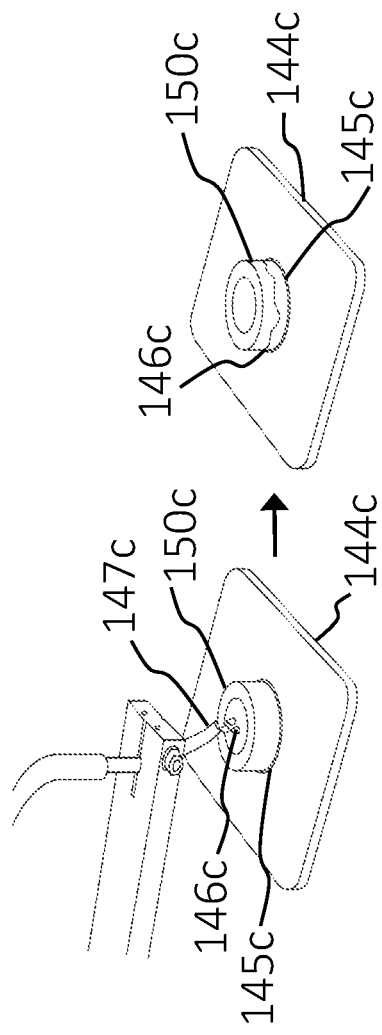
FIG. 68a  FIG. 68b  FIG. 69a  FIG. 69b

ADVANCED SCENT DISPERSION DEVICE

RELATED APPLICATIONS

This application claims priority to U.S. Provisional Patent Application 62/442,558, filed Jan. 5, 2017; United States Provisional Patent Application 62/442,561, filed Jan. 5, 2017; and also claims priority to U.S. Non-Provisional application Ser. No. 15/622,058, filed Jun. 13, 2017, which claims priority to U.S. Provisional Patent Application 62/350,696, filed Jun. 15, 2016, all of which are hereby incorporated by reference.

BACKGROUND

Air fresheners are common devices that release scents into the atmosphere. For example, they can be used to help create a comforting home environment or to help maintain the ambience of a professional office space. They can also be used to mask, neutralize, or counteract undesirable odors in hospitals and lavatories. There may even be potential health benefits from scents that boost mood and alleviate stress.

Despite growing use, air fresheners still leave much to be desired. For example, some devices include solid-based ingredients that drip messy wax or leave other residue that requires cleaning after use. Some devices, like wicks and reeds, present problems such as rapid scent loss, poor scent intensity, and lack of character. Some devices require a lengthy time for scent delivery or provide uneven scent distribution. Improvements to scent quality and scent delivery are needed.

Additional improvements are needed for the technology, cost, and design of air fresheners. For example, some devices have an unattractive aesthetic appearance or take up too much space to blend with an environment. Some devices necessitate an electrical outlet which can limit where they are placed in a given room. Some devices are heated which can yield unstable temperatures over time. Some devices have very little means of control once they are opened or turned on, which can shorten the life of the device. Thus, a need exists for one or more improvements on existing air fresheners.

SUMMARY

An exemplary scent dispersion device comprises a housing and a refill cartridge. The refill cartridge includes a porous material retaining a volatile substance. The refill cartridge is located within the housing and constructed such that air directed from an external fan is through and out the top of the refill cartridge to volatize the volatile substance into the air.

Another exemplary scent dispersion device comprises a housing that includes a plurality of air inlets at or near the base of the housing and that are configured to allow air flows up from underneath the housing, through the housing, and out from a top of the housing. A refill cartridge retains a volatile substance and is situated within the housing such that air flows flowing up through the housing volatize the volatile substance into the air.

A scent dispersion device may include a side arm for resting the device sideways as well as a removable clip for clipping the device to a structure for hanging the device. Other features may also be included.

A tray is configured to hold a plurality of scent dispersion devices within recesses of the tray. The tray contains a plurality of holes within a bottom surface of each recess and a fan located underneath the bottom surface of each recess directs air flows upward to enter air inlets of the plurality of devices and thus volatize the volatile substance within each device.

A computer-implemented method for controlling a scent dispersion device and a tray includes steps of presenting at least one control representation, and receiving at least one selection from the at least one presented control representation. For at least one of the selected control representations, the method further includes presenting at least one second-level setting associated with the selected control representation, receiving at least one selection from the at least one presented second-level setting, and implementing at least one selected control representation and at least one selected second-level setting.

An exemplary method is implemented at a computer system that includes one or more processors. An exemplary method may further be incorporated as a computer program product comprising one or more computer-readable storage media having thereon computer-executable instructions that are structured such that, when interpreted by one or more processors associated with a computing system, cause the computing system to perform method steps.

A method for making a scented refill cartridge includes making a central axial opening through a solid cylinder made of an absorbent scent retaining material, placing the cylinder within a recess on a platform, pouring liquid fragrance into the central opening to a level that is below a top surface of the cylinder to allow the liquid to be absorbed into the absorbent material, placing the cylinder within a cup, sealing the top opening with a first removable foil or film; and sealing the bottom opening with a second removable foil or film to seal the cylinder within the interior of the cup. The scented refill cartridge is configured to be included in a scent dispersion device which includes a housing, fan, and controller, with optional cover that can be decorated.

A system or apparatus for making a scent-absorbed wick includes one or more of a pouring station, sealing station, and labeling station. The pouring station includes a first movable horizontal surface with multiple recesses. Each recess is configured for holding an absorbent structure. The pouring station further includes a structure for pouring liquid fragrance onto the absorbent structure. Structure is further provided for moving successive recesses in turn into and out of the pouring station.

BRIEF DESCRIPTION OF DRAWINGS

FIG. 68a illustrates a wick and a platform.

FIG. 68b illustrates a wick placed within a recess of a platform.

FIG. 69a illustrates scented fragrance being poured into a wick.

FIG. 69b illustrates the scented fragrance being absorbed into a wick.

DETAILED DESCRIPTION

The Scent Delivery System

Figure 1:
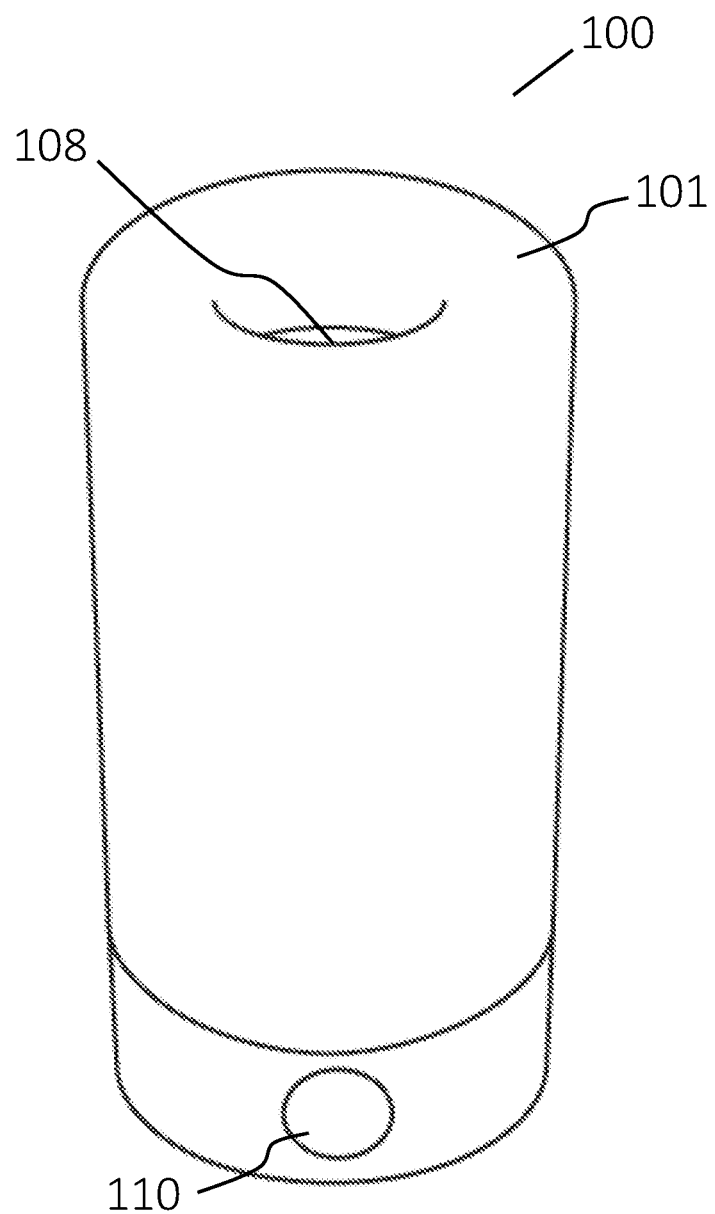
FIG. 1 illustrates a perspective view of a scent dispersion device.

An exemplary scent dispersion device comprises a housing and a refill cartridge. The refill cartridge includes a porous material retaining a volatile substance. The refill cartridge is located within the housing and constructed such that air directed from an external fan is through and out the top of the refill cartridge to volatize the volatile substance into the air.

Another exemplary scent dispersion device comprises a housing that includes a plurality of air inlets at or near the base of the housing and that are configured to allow air flows up from underneath the housing, through the housing, and out from a top of the housing. A refill cartridge retains a volatile substance and is situated within the housing such that air flows flowing up through the housing volatize the volatile substance into the air.

A scent dispersion device may include a side arm for resting the device sideways as well as a removable clip for clipping the device to a structure for hanging the device. Other features may also be included.

A tray is configured to hold a plurality of scent dispersion devices within recesses of the tray. The tray contains a plurality of holes within a bottom surface of each recess and a fan located underneath the bottom surface of each recess directs air flows upward to enter air inlets of the plurality of devices and thus volatize the volatile substance within each device.

A computer-implemented method for controlling a scent dispersion device and a tray includes steps of presenting at least one control representation, and receiving at least one selection from the at least one presented control representation. For at least one of the selected control representations, the method further includes presenting at least one second-level setting associated with the selected control representation, receiving at least one selection from the at least one presented second-level setting, and implementing at least one selected control representation and at least one selected second-level setting.

An exemplary method is implemented at a computer system that includes one or more processors. An exemplary method may further be incorporated as a computer program product comprising one or more computer-readable storage media having thereon computer-executable instructions that are structured such that, when interpreted by one or more processors associated with a computing system, cause the computing system to perform method steps.

A method for making a scented refill cartridge includes making a central axial opening through a solid cylinder made of an absorbent scent retaining material, placing the cylinder within a recess on a platform, pouring liquid fragrance into the central opening to a level that is below a top surface of the cylinder to allow the liquid to be absorbed into the absorbent material, placing the cylinder within a cup, sealing the top opening with a first removable foil or film; and sealing the bottom opening with a second removable foil or film to seal the cylinder within the interior of the cup. The scented refill cartridge is configured to be included in a scent dispersion device which includes a housing, fan, and controller, with optional cover that can be decorated.

A system or apparatus for making a scent-absorbed wick includes one or more of a pouring station, sealing station, and labeling station. The pouring station includes a first movable horizontal surface with multiple recesses. Each recess is configured for holding an absorbent structure. The pouring station further includes a structure for pouring liquid fragrance onto the absorbent structure. Structure is further provided for moving successive recesses in turn into and out of the pouring station.

An exemplary scent delivery system includes a scent dispersion device that includes a housing that releases a volatile substance into the air as directed by a fan. Within the housing, a refill cartridge includes a porous body that retains the volatile substance. Also within the housing is a fan and a controller, the fan being controlled by the controller for directing air up through the housing. The refill cartridge is located in air flow directed by the fan and constructed such that air flow directed from the fan flows through the refill cartridge and out of the housing to volatilize the volatile substance into air.

Also described is a refill cartridge that comprises a cup support containing a porous body that retains the volatile substance. The refill cartridge is located in air flow directed by the fan and constructed such that air flow directed from the fan flows from a bottom of the body to a top of the body along exterior and interior wall surfaces of the body, and out of the housing to volatilize the volatile substance into air.

Also described is a standalone housing which contains a scent refill cartridge and a fan. The housing is generally cylindrical and vertically aligned to provide an upward air path through the housing and release scent from the cartridge through an orifice of the housing into an external environment. With the device turned on, the fan draws air through air inlets of the housing and forces the air upward through the interior of the housing. The air inlets are below the fan, and can be of any suitable configuration, such as one or more air inlets in the bottom of the housing or on the side of the housing.

The fan is powered by a battery and is controlled by a controller. The battery and controller are contained in the housing at any suitable location, such as below the fan in a position configured to allow air flow.

The battery may be any suitable battery. A rechargeable battery is suitable and may include within the housing recharging circuits. The recharging circuit may include a plug in the housing for a charging jack, or a wireless inductive charging system. While the device is a standalone device, an embodiment includes that an electrical port be used so that the device can be connected to an electrical outlet for activating the device and/or recharging the device.

An exemplary device 100 is shown in FIG. 1 and includes housing 101, orifice 108, and a manual input 110. A scented refill cartridge (not shown) is nested within an interior of the housing 101. The manual input 110 may include one or more buttons or other manual mechanism to activate and de-activate the device. The manual input may further provide a means of programming the device. The orifice 108 provides a curved donut hole-like or funnel-shaped opening which promotes scented air flow into the surroundings.

While the device is described having a vertical orientation relative to a ground surface, the device may assume alternate orientations (e.g. horizontal, angled, upside down, etc.) with air flows following the orientations.

Figures 2, 3:
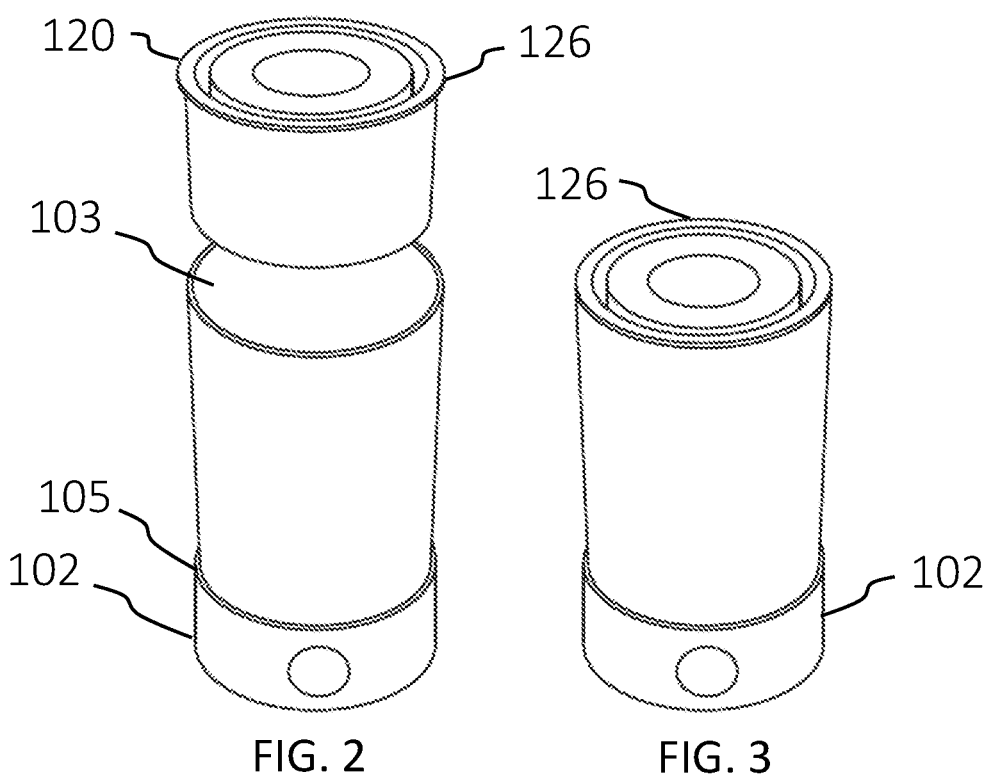
FIG. 2 illustrates a perspective view of a base and a cartridge.
FIG. 3 illustrates a perspective view of a base and a cartridge.
Figures 4, 5:
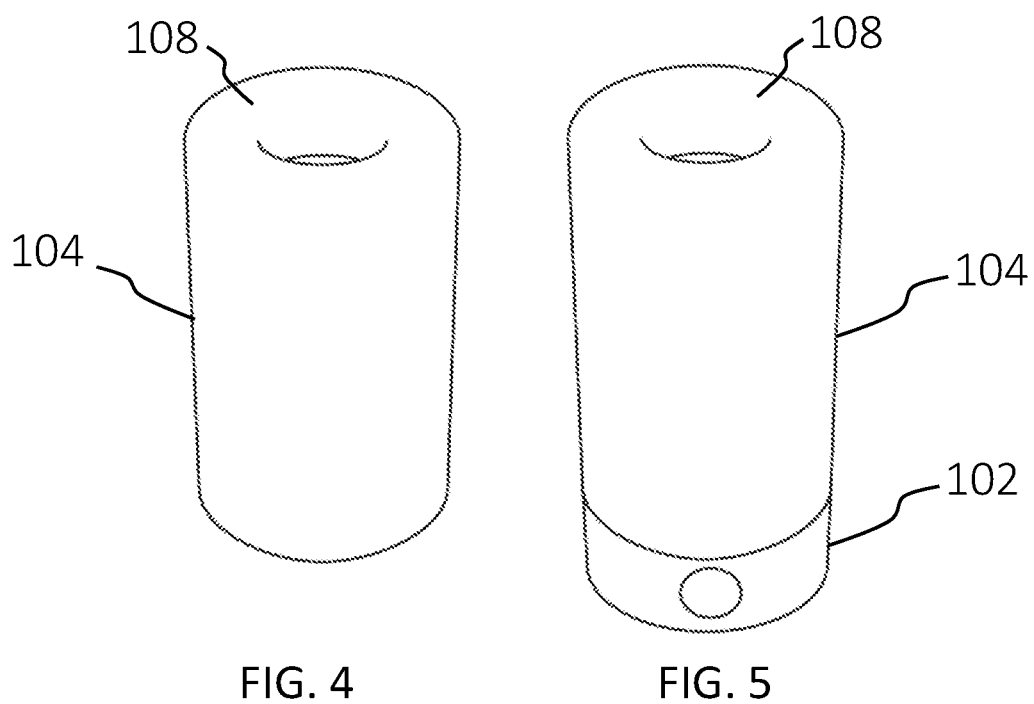
FIG. 4 illustrates a perspective view of a cover.
FIG. 5 illustrates a perspective view of a scent dispersion device.

An embodiment includes that the housing be a single unit. Alternatively, the housing may comprise two parts, a base and a cover. Turning to FIGS. 2, 3, 4, and 5, various views of an exemplary device are shown including a scent refill cartridge 120 and a housing that comprises a base 102 and outer cover 104. To assemble the device, the cartridge 120 is inserted into a cylindrical hollow 103 of the base 102, as seen in FIGS. 2 and 3. The cover 104, as shown in FIGS. 4 and 5, can be engaged and disengaged from the base 102 to allow a user to replace the cartridge 120. The device may be used without the cover 104 and still be fully operable.

Once inside the base 102, the cartridge 120 lays generally flush with the base 102, as shown in FIG. 3. The fit of the cartridge 120 within the base 102 is a snug, friction fit. The cartridge 120 may include an outer lip 126 that extends radially outward from upper edges of the cartridge 120, the outer lip 126 effectively acting as a stop which restricts the cartridge 120 from further longitudinal displacement toward the bottom of the base 102. The outer lip 126 further provides a finger hold for removing the cartridge 120 from the base 102 in order to replace it with a new cartridge.

The outer cover 104 is shown in FIG. 4. A suitable configuration is for the cover 104 to be a hollow cylinder with a dome-like top and that can be slidably engaged to the base 102. The cover 104 further includes an orifice 108 for air to exit through after it is blown up and through the refill cartridge by the fan, the orifice 108 effectively serving as a vent that provides an air path to the outside environment. The orifice 108 may also include components (e.g., scented oils, liquids, etc.) to combine with the scented air exiting the device.

For the base 102, structure may include a shoulder 105 as shown in FIGS. 2 and 3 or other restrictive means that stops the cover 104 from sliding any further on the base 102. Contact between the cover 104 and the shoulder 105 completes attachment of base 102 to cover 104. The cover 104 fits to the outer surface of the base 102 with a sliding or friction fit such that it can be easily attached and removed. The fully attached position of cover 104 and base 102 is shown in FIG. 5.

Figure 6:
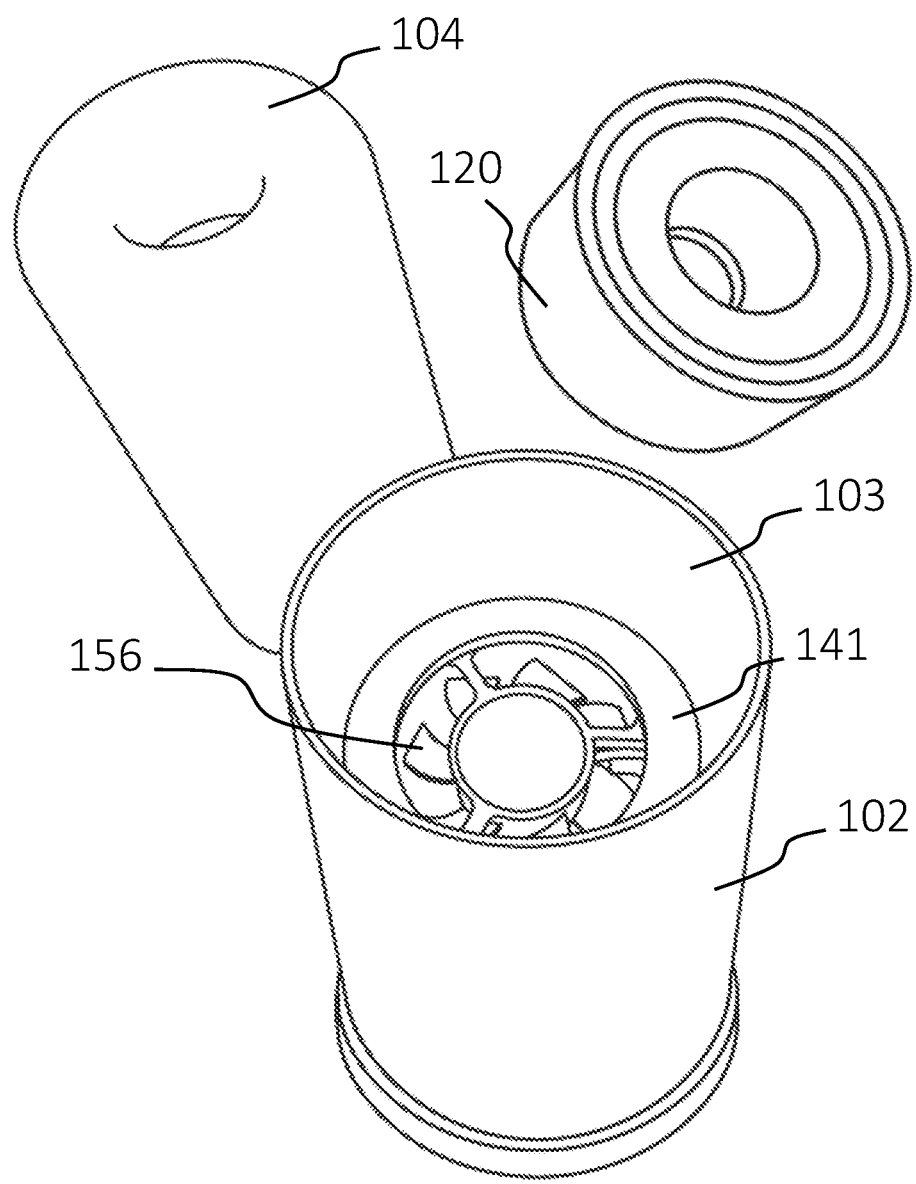
FIG. 6 illustrates a perspective view of an unassembled scent dispersion device including a base, cover, and cartridge.

Turning to FIG. 6, the cover 104, cartridge 120, and base 102 are shown. A fan 156 is located within the hollow 103 of the base 102 and is configured to push air upward toward the top of the base 102. The fan includes air holes such as the holes shown which allow air to travel in a generally unobstructed path through the fan. Located above the fan 156 is an annular flange 141 or shoulder that extends radially inward from the interior walls of the hollow 103. The width of the flange 141 provides a support for the cartridge 120. The cartridge 120 and flange 141 can be stacked so as to provide a generally unobstructed air flow through the cartridge 120.

When the cartridge 120 is inserted into the hollow 103 and a cover 104 is placed over the base 102, there is an interior space defined between the top of the cover 104 and the top of the cartridge 120 in which air flows toward the orifice 108. The air flow in the interior space can be improved by shaping or streamlining the interior space. For example, air flow may be directed outside of the orifice 108 by contours, such as angled and/or curved surfaces along the underside of the top of the cover 104. This can be accomplished by molding a shaped interior during molding of the cover 104.

Figure 7:
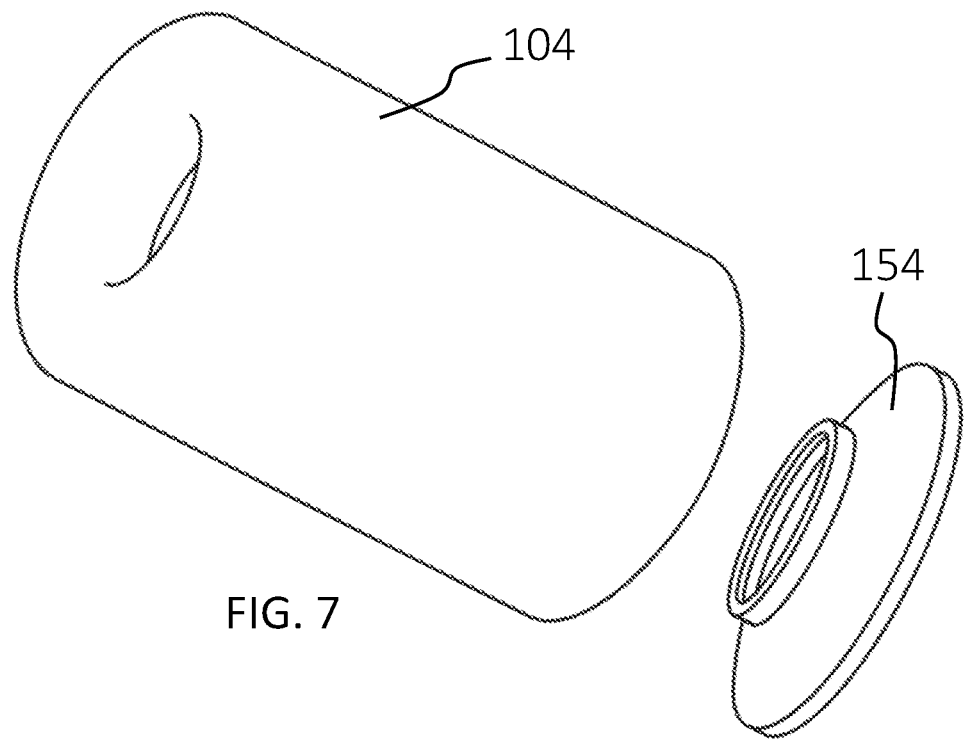
FIG. 7 illustrates a perspective view of a cover and an insert ring.
Figure 8:
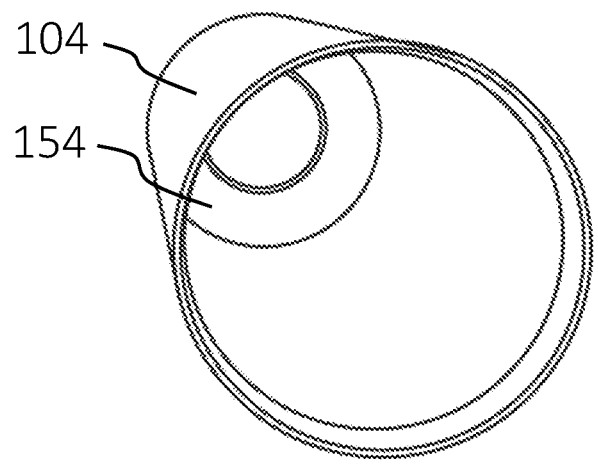
FIG. 8 illustrates a perspective view of a cover and an insert ring.
Figure 9:
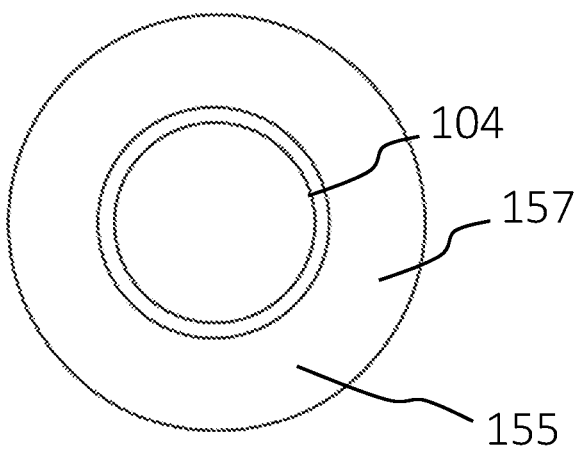
FIG. 9 illustrates a top view of an insert ring.
Figure 10:
FIG. 10 illustrates a perspective view of an insert ring.
Figure 11:
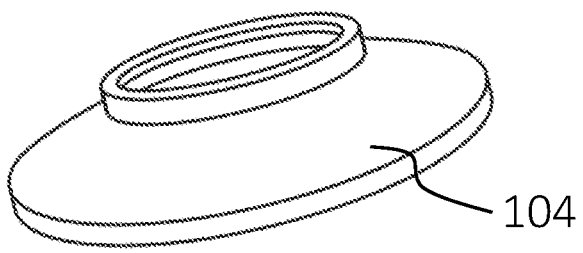
FIG. 11 illustrates a perspective view of an insert ring.
Figure 12:
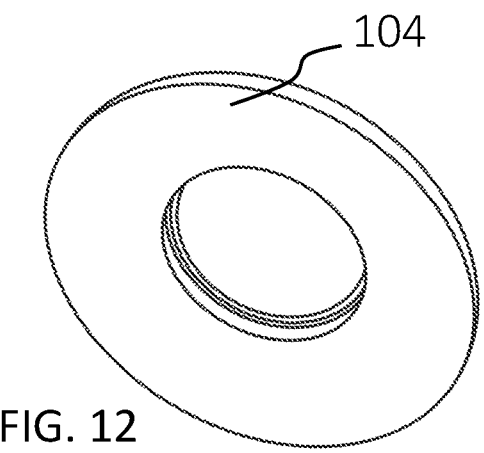
FIG. 12 illustrates a perspective view of an insert ring.
Figure 24:
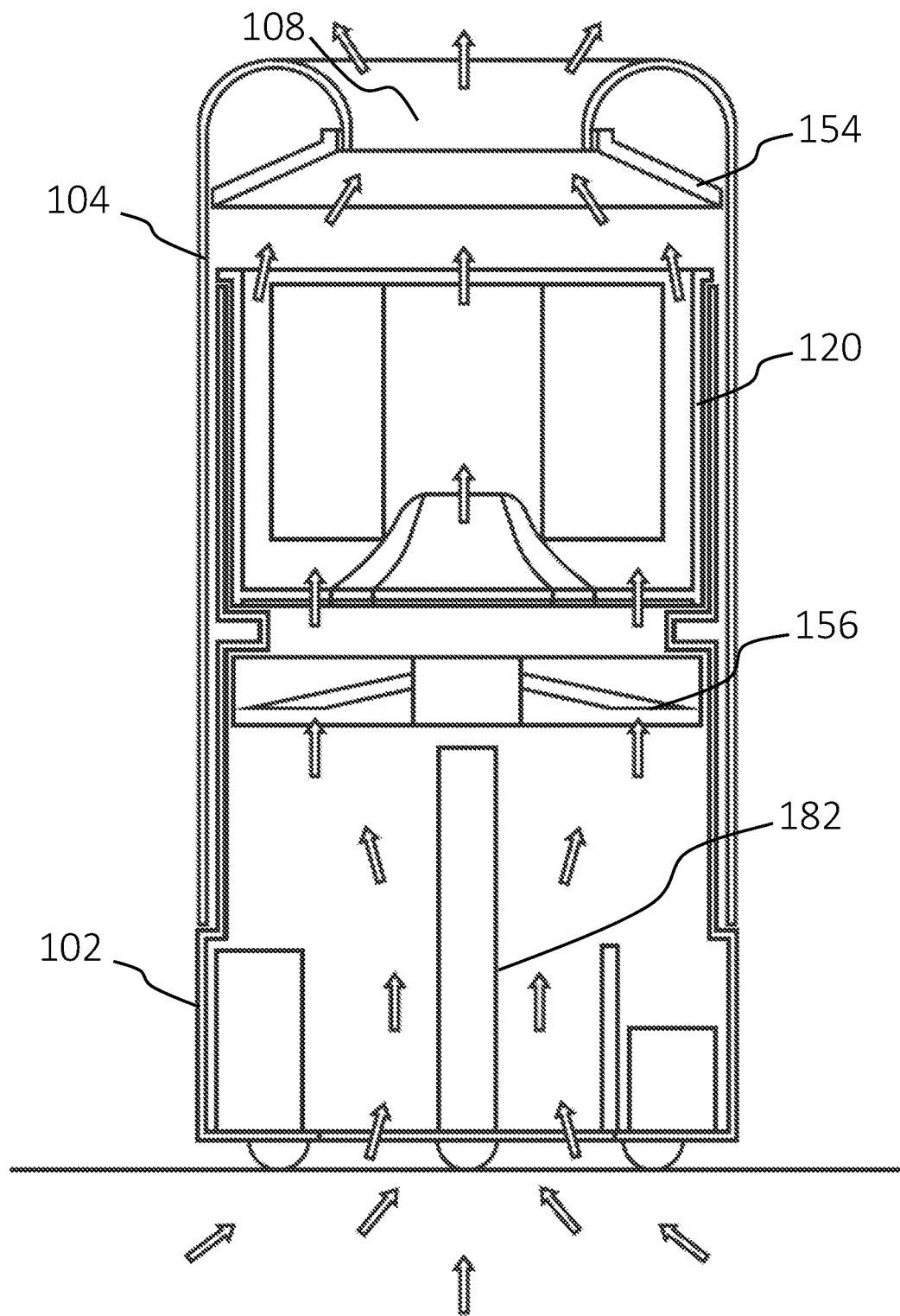
FIG. 24 illustrates exemplary air flows through a scent dispersion device.
Figure 25:
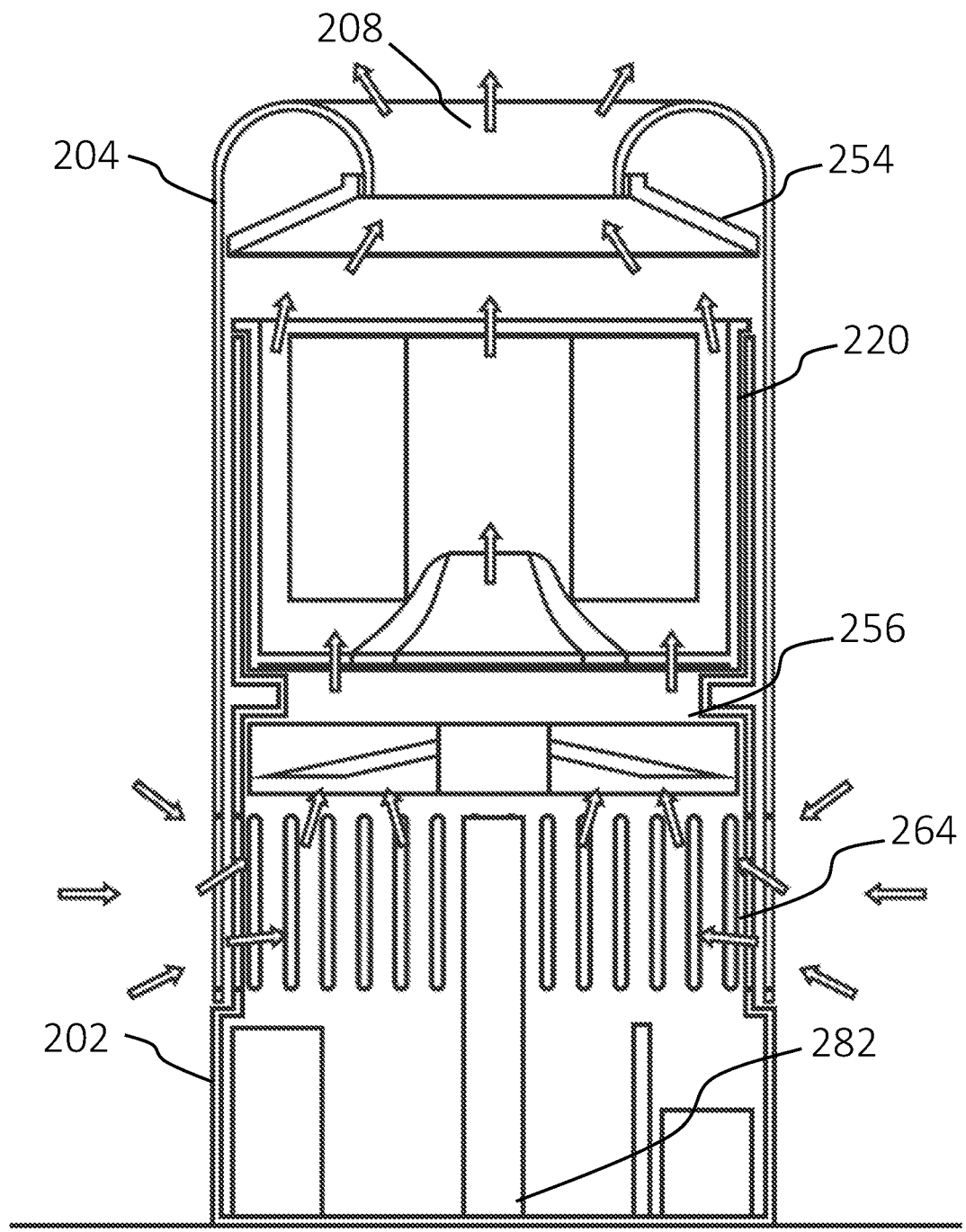
FIG. 25 illustrates exemplary air flows through a scent dispersion device.

Alternatively, as shown in FIG. 7, a removable insert ring 154 may be provided as an insert for the cover 104. The insert ring 154 may be described as a flexible disc with angled sides and an axial hole therethrough. The insert ring 154 is inserted into the hollow interior of the cover 104 and pressed up against the underside of the cover 104. In an attached position, the insert ring 154 is held in place underneath the top of the cover 104 by a friction fit or other attachment (e.g., bonded, screwed together, etc.). The hole of the ring is concentric with the orifice 108 of the cover 104, the hole of the ring being similar in diameter. For example, the hole of the ring may be smaller in diameter to fit at least partially within the orifice, be of the same diameter as the orifice, or be slightly larger in diameter than the orifice 108 to fit around inner walls of the orifice. An exemplary attached position of the insert ring and cover is illustrated in FIGS. 8, 24, and 25.

Various views of the insert ring are provided in FIGS. 9, 10, 11, and 12. The ring is defined by a ring wall 155 that can be inserted at least partially around or within the orifice 108 of the cover 104. The ring includes a wing 157 that extends radially outward and slightly angles away from the ring wall 155. The top surface of the ring wall 155 is generally flat, or may be rounded in a concave or convex manner. The bottom surface of the wing 104 is also generally flat or rounded in a slightly concave or convex manner. With the insert ring 104 in place, air pockets getting trapped within the top rounded dome of the cover 104 are prevented because the wing 104 covers the rounded concave or donut shape surface of the underside of the cover 104, and is configured to direct air flow smoothly out of the housing.

Figure 13:
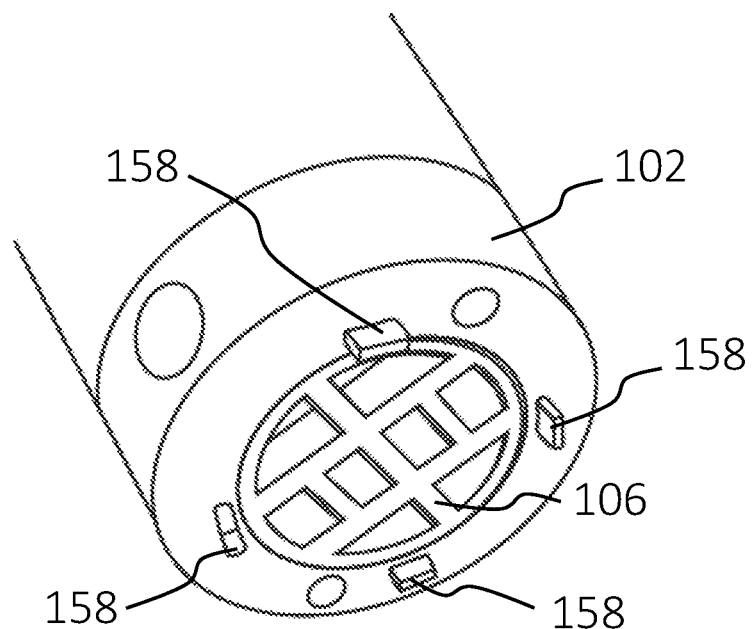
FIG. 13 illustrates a perspective view of a bottom portion of a base.
Figure 14:
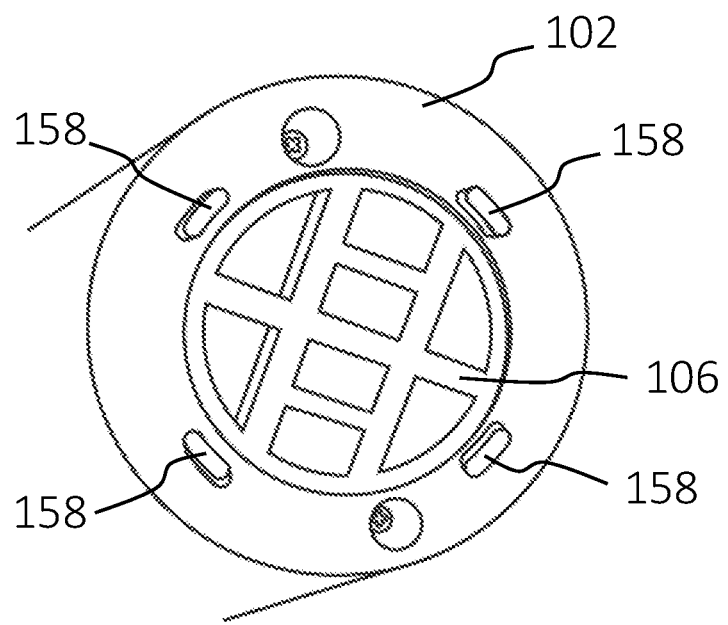
FIG. 14 illustrates a perspective view of a bottom portion of a base.

The air flow through the housing originates from one or more air inlets located on side walls of the housing 101 or underneath the base 102. Passage of air flow from underneath the housing 101 is enabled by raising the base 102 above a ground surface level. An exemplary plurality of legs 158 are shown underneath the base 102 in FIGS. 13 and 14. Each leg 158 extends downward from underneath the base 102. The legs 158 are spaced apart so as to support the base and allow for air flow. As shown, the legs 158 are spaced on opposite sides from each other on the underside of the base 102 and are sufficiently narrow in width to allow air flow circulation underneath the base 102. The plurality of legs may raise the housing by a height. Non-limiting exemplary heights include 0.10-0.20 cm, 0.21-0.25 cm, 0.26-0.30 cm, 0.31-0.40, 0.41-0.50 cm, etc.

In addition, the underneath surface of the base 102 may include a panel 106 that defines one or more air inlets. An air inlet may be any one or more of an opening, vent, flue, shaft, duct, channel, passage, pipe, or pipeline. The panel 106 may be molded as part of the base 102, or alternatively, the panel 106 may be a separate unit that attaches to the base 102. The panel 106 may be centrally located on the underneath surface of the base 102 as shown. The panel 106 is configured such that air may be directed up from underneath the base 102 and through the housing in a generally vertical direction.

The base and cover of the scent dispersion device are configured to allow easy removal and replacement of the scented refill cartridge. The cartridge is likewise configured to be easily removable and replaceable from the base. The cartridge provides structure to direct an air stream directed against the cartridge and disperse a scent into the surrounding environment. A suitable configuration includes a solid porous material in a cylindrical form.

Figure 15:
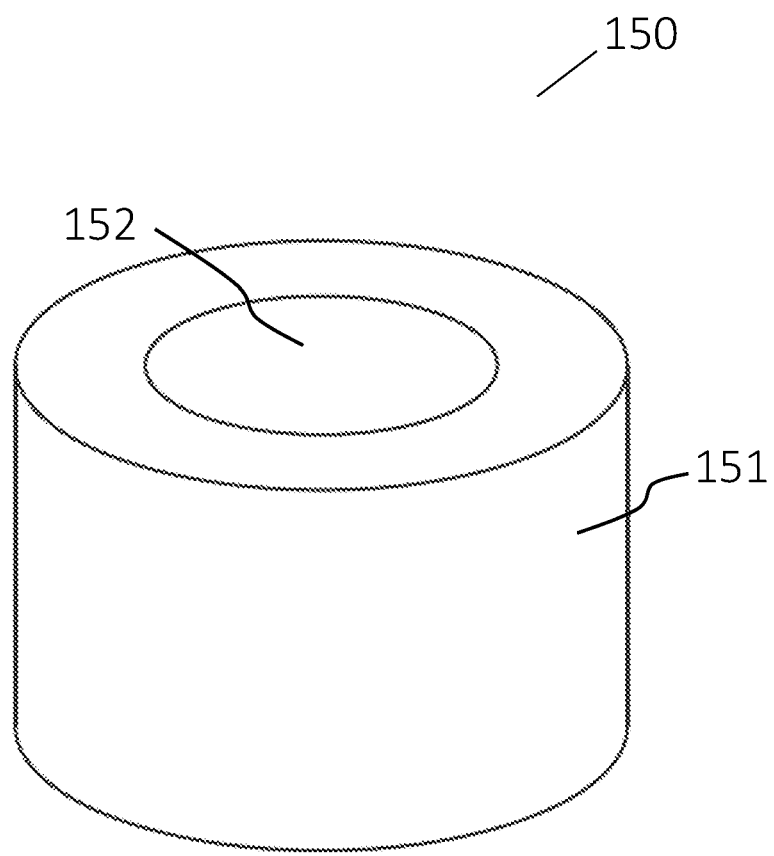
FIG. 15 illustrates a perspective view of a wick.

Turning to FIG. 15, a porous material in the form of an exemplary wick 150 is shown. Being porous allows the wick 150 to hold a volatile liquid scent. Suitable porous materials for the wick 150 include, for example, one or more of dried wood pulp, other wood forms (e.g. natural wood, recycled wood, etc.), cellulose, foams of natural or synthetic polymers, natural or synthetic fibers, ceramics, porcelain, plastics, fabrics, cotton, glass, and composites thereof.

The wick may take a variety of shapes, such as a sphere, ovoid, ellipsoid, pyramid, trapezoid, polyhedron, cuboid, etc. The wick 150 as shown includes a generally cylindrical body 151 formed with a hole or central axial opening therethrough. The cylindrical body 151 includes a generally flat top surface and a generally flat bottom surface. The body 151 further includes generally flat exterior surface walls and generally flat interior surface walls.

The volatile liquid scent can be any suitable diluted or undiluted oil or water-based scent material in the liquid state that volatilizes into vapor in air. This includes scented oils, essential oils, and any suitable fragrance composition. Applications may further include odoriferous and stinky materials. Also contemplated are volatile materials that have a medicinal, biological, or like application. The device does not include a heater to volatilize the liquid, so suitable materials are those that vaporize or evaporate sufficiently in the fan directed air stream without heating.

Figure 16:
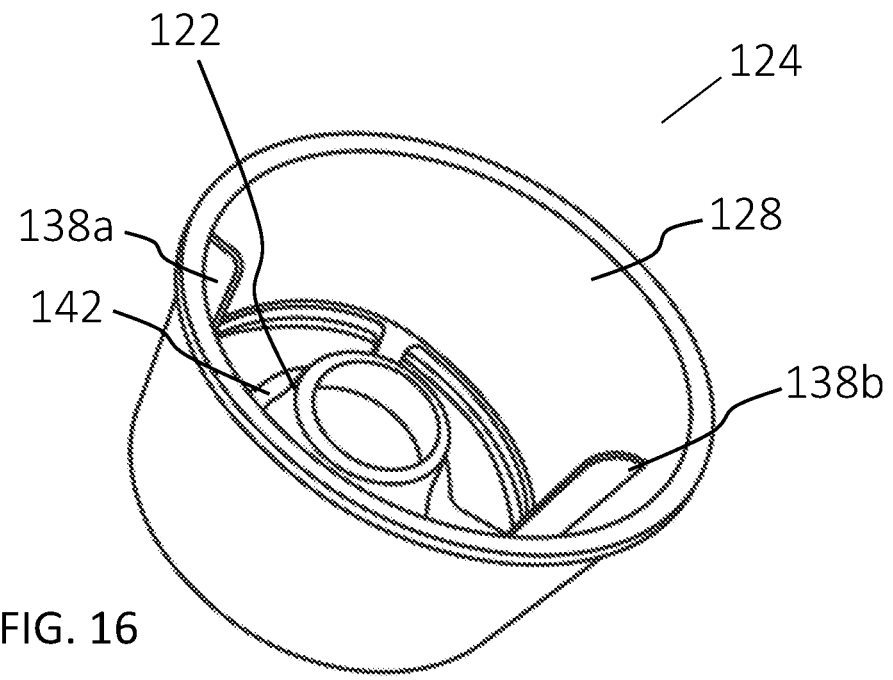
FIG. 16 illustrates a perspective view of a cup support.
Figure 17:
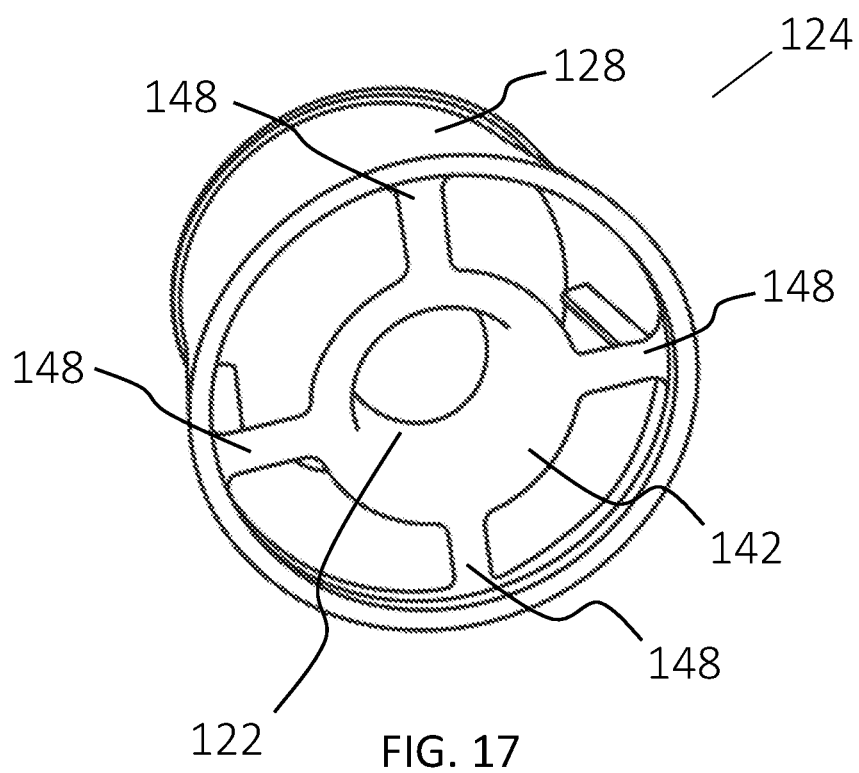
FIG. 17 illustrates a perspective view of a cup support.

As shown in FIGS. 16 and 17, an exemplary suitable cup support 124 for the wick 150 is shown. To increase the surface area for air flow and emission of scent from the porous material, the cup support 124 includes one or more holes on both ends. The cup support 124 as shown includes structure to direct air into the holes and thus diffuse evaporated scent into the air stream.

The cup support 124 includes solid lateral side walls 128 and a bottom forming a cup-like shape. The walls 128 may be vapor impermeable. The walls 128 and bottom define a space for containing a wick. The bottom includes one or more of a narrowing stream constrictor 142 and a support section 148. As shown in FIGS. 16 and 17, the narrowing stream constrictor 142 is surrounded annularly by the support section 148.

The narrowing constrictor 142 of the cup support 124 includes walls that form a funnel shape. In the vertical direction, the curved walls start by defining a large central opening at the bottom of the cup and then gradually curve and taper inward to direct and streamline the air flow upward toward the top of the cup. The walls are configured to extend at least partially within the cup space. Upper edges of the walls form a smaller opening relative to the large central opening.

In the downward facing direction, the curved walls that define the large opening at the bottom of the cup curve downward and radially outward to a horizontally extending direction so as to be partially extended toward the side walls of the cup, perpendicular to the cup axis. In this manner, the walls radially extend outward to form an annular ridge around the large opening, and may be used to support the wick in certain embodiments.

Extending radially outward from the narrowing constrictor 142 is a support section. The support section 148 includes one or more holes that provide space for air to flow upward into the cartridge from the fan. An exemplary support section 148 is shown formed by four arms that extend radially outward in opposing directions from the constrictor 142 and connect with side walls 128 of the cup support 124.

Alternatives include a bottom structure without a narrowing constrictor and/or without a support section. The bottom structure may simply have holes and/or alternative structure that allows air to flow and/or streamlines air flow through the cartridge. Also, the wick itself may have curvature that streamlines air flow. For example, inner walls may curve outwardly similar in nature to the curvature of the constrictor.

The cup support 124 may include vertical ridges 138a and 138b that are configured to hold the wick in place relative to the cup support 124. As shown in FIGS. 16 and 17, the vertical ridges 138a and 138b extend radially inward and vertically upward from the base support.

The ridges are diametrically opposed along interior walls of the cup support 124 so as to engage the wick from opposite sides. Distal ends of the ridges 138a and 138b converge with two of the four diametrically opposed arms as shown. The ridges and arms have planar alignment, which helps to streamline air flow. Variations may include other configurations, for example, four ridges with each of the ridges in alignment with respective arms.

At proximal ends, the ridges 138a and 138b have curved upper edges rather than sharp edges that could dig in and tear or otherwise damage the wick 150. The curved upper edges further allow the wick 150 to easily slide in and out of the cup support 124. At distal ends, alternatives include that the ridges curve or bend to form horizontal supports for the wick and that prevent the wick from longitudinal displacement toward the distal end of the cup.

Figure 18:
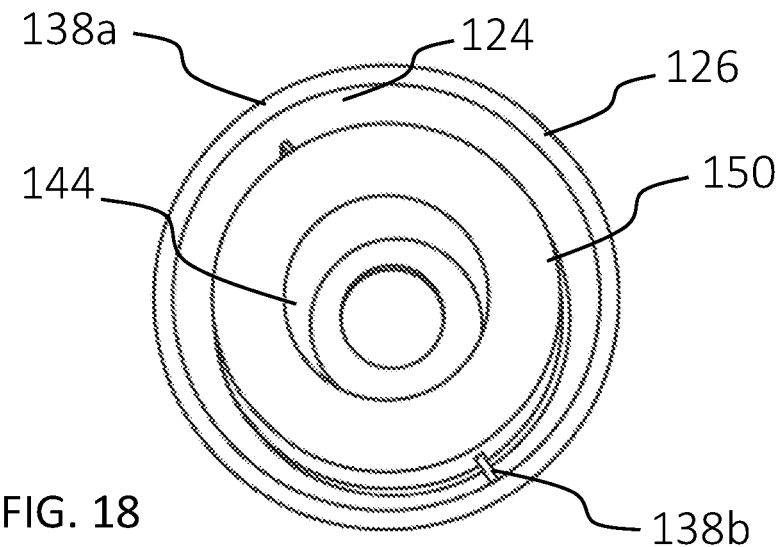
FIG. 18 illustrates a perspective view of a refill cartridge.
Figure 19:
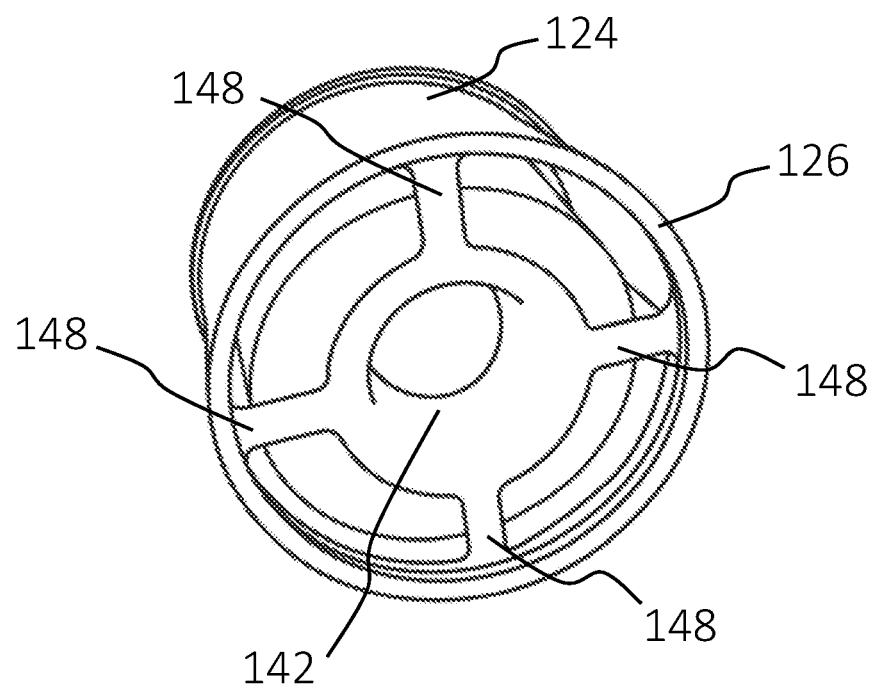
FIG. 19 illustrates a perspective view of a refill cartridge.

In FIGS. 18 and 19, the wick 150 is shown positioned within the interior space defined by the cup support 124. The wick 150 may be held in place by the ridges 138a and 138b and/or be partially supported by the support section 148 and/or the constrictor 142. The wick 150 is centered coaxially within the cup support 124, the hole of the wick 150 being generally aligned with a central hole of the cup support 124. The constrictor 142 at least partially extends up through the opening of the wick 150. The central hole of the wick 150 is generally in axially alignment with the funnel opening of the constrictor 142.

Also, the outer diameter of the wick 150 is less than the inner diameter of the cup support 124 so as to leave a vertical annular space around the outer walls of the wick 150. The space defined between inner walls of the cup support and outer walls of the wick provide for air pathways along the exterior wall surface of the wick 150. The annular space provides air pathways that go from the bottom opening of the cup support 124 to the top opening of the cup support 124. Air flows can travel along sidewalls of the wick 150 and within the interior walls of the wick. The contact between the exterior surface walls of the cup support 124 and inner walls of the base 102 is a friction fit, negating any space therein for air to flow.

Initially, air flows up from the base openings and then bifurcates to the constrictor 142 and the annular space around exterior surface walls of the wick. The constrictor 142 directs air flow along inner walls of the wick 150 while the space between the cup and the wick directs air flow along outer walls of the wick 150. With openings provided by the support section 148 at the bottom of the wick, air that flows to the exterior surface walls also flows along the bottom surface of the wick 150. The two air flows (i.e., flow along exterior surface walls of the wick and flow along inner walls of the wick) converge at the top of the wick 150, to flow along the top surface of the wick 150 and up toward the top of the housing and out through the orifice of the cover.

With the inner hole of the wick, outer walls of the wick, and top and bottom surfaces of the wick exposed to air flow, the wick is configured for an even air flow distribution over the entire outer surface, or a substantial portion of the outer surface, of the wick, which results in efficient evaporation and optimal scent release through the top of the housing.

The cup support 124 contains a scented wick 150 that has absorbed or otherwise retained a liquid fragrance or other volatile liquid. The cup support is advantageous for several reasons. For example, the cup support keeps fingers clean during handling, including set up, clean up, replacement, use, etc. This is unlike other aroma devices that use wax that drips onto the ground and that must be cleaned off or otherwise removed from the device. The wick is also advantageous because it is long-lasting, with steady scent released into the air as provided by a fan. The distribution of the scent is favorable because of the air pathways that direct air flow steadily and efficiently. There is no need to wait for a device to heat up or have other delays in release of scent because the fan and wick combination provide an instant scent release that permeates the atmosphere. Other advantages are readily apparent.

Figure 20:
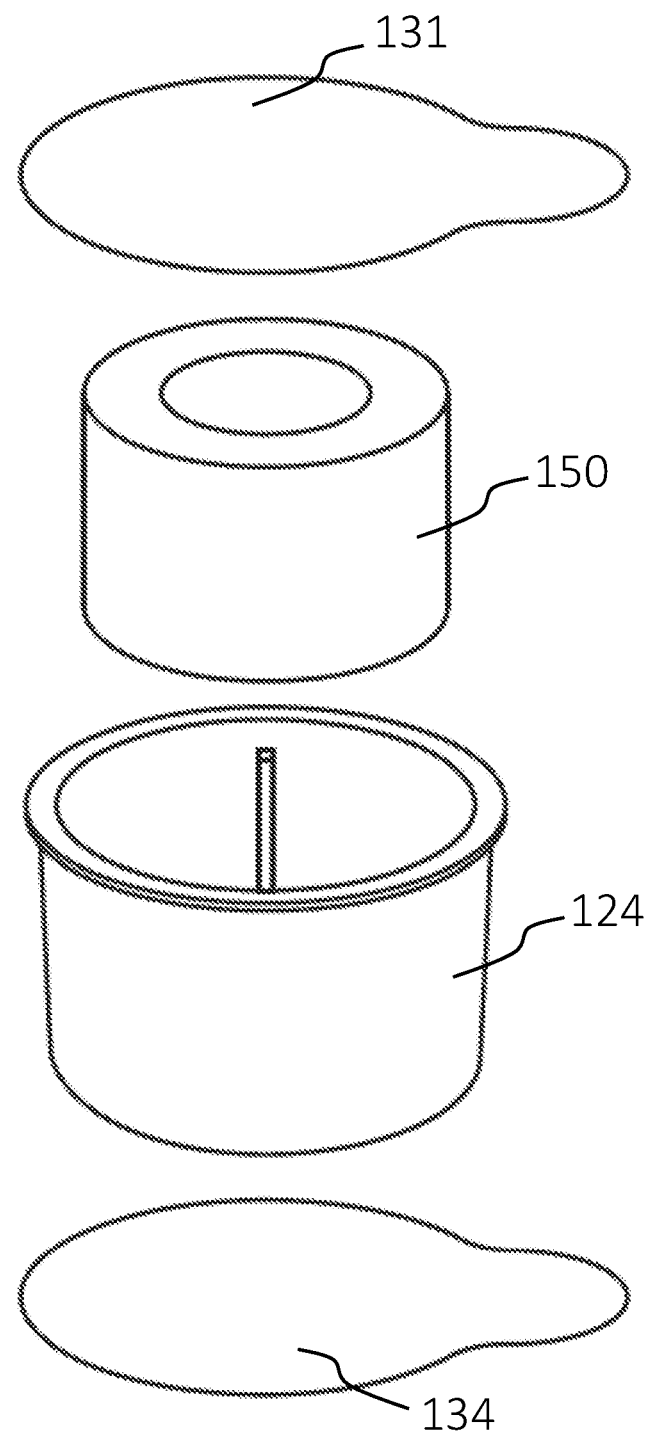
FIG. 20 illustrates an extruded view of a refill cartridge with top and bottom seals.

When the life of a refill cartridge in the device is spent, it can be replaced with a new one from storage. To prevent the liquid fragrance, or other volatile liquid, from being lost during storage, the stored refill cartridge is suitably sealed in packaging or a container. Turning to FIG. 20, components of a cartridge are shown in an extruded view including a wick 150, a support cup 124, a top seal 131, and a bottom seal 134. The top and bottom seals 131 and 134 cover respective top and bottom openings of the refill cartridge during storage. The seals are comprised of a flexible impermeable material (e.g., metal foil or polymer film) that are joined to the support cup with a removable adhesive to seal the interior off from scent release.

The seals lay generally flat on top and bottom surfaces of the refill cartridge. The height of the wick 150 is less than the height of the cup support 124 so that the top seal 131 lays flat across the top opening of the cup support. Also, the constrictor and support section are configured to be fully contained within the cup support so that the bottom seal 134 lays flat across the bottom opening of the cup support.

Non-limiting exemplary dimensions of the wick include an outer diameter between 1.25 to 1.59 inches, 1.60 to 1.75 inches, and 1.76 to 2.00 inches, an inner diameter between 0.50 to 1.00 inch, 1.10 to 1.25 inches, and 1.26 to 1.50 inches, and a height between 0.75 to 1.00 inch, 1.10 inch to 1.25 inches, and 1.26 inches to 2.00 inches. Other dimensions are anticipated.

Figure 21:
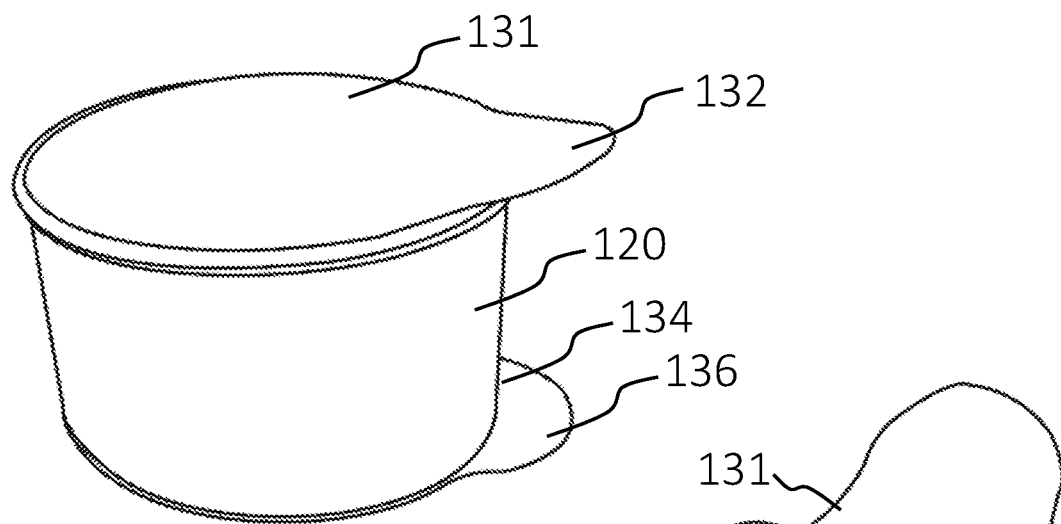
FIG. 21 illustrates a perspective view of a refill cartridge with top and bottom seals.
Figure 22:
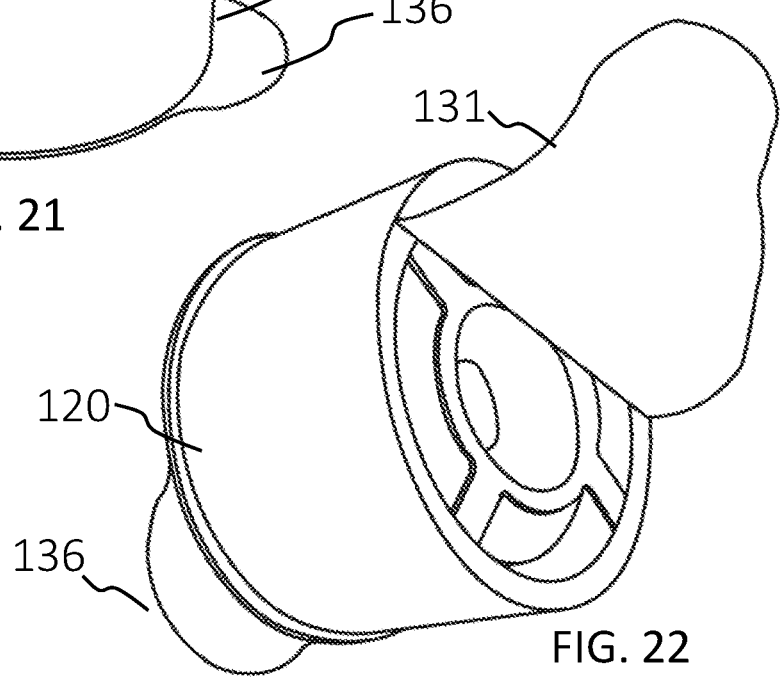
FIG. 22 illustrates a perspective view of a refill cartridge with top and bottom seals.
Figure 23:
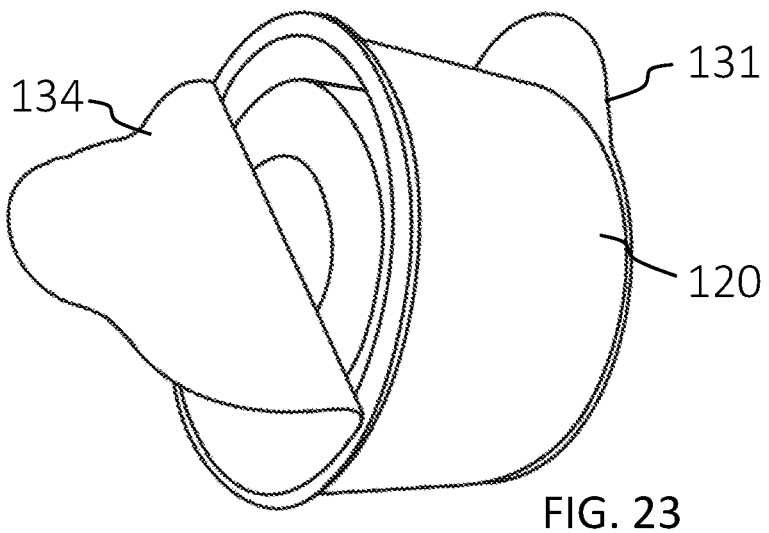
FIG. 23 illustrates a perspective view of a refill cartridge with top and bottom seals.

FIGS. 21, 22, and 23 show an exemplary cartridge 120 with a top seal 131 and a bottom seal 134 and respective pull tabs 132 and 136 for opening the cartridge 120. The top and bottom seals 131 and 134 extend to circumferential edges of the top and bottom openings of the cup support. Pull tabs 132 and 136 are extended members of the seals that extend radially outward from the circumferential edges so that the user may easily grasp them to remove top and bottom seals 131 and 134 by peeling or pulling them away from the cartridge 120. Top and bottom seals 131 and 134 are removed prior to the cartridge 120 being inserted into the base 102. An embodiment includes that the seals be re-sealable so as to further the life of the wick 150 after each use.

To use the device, the seals are removed from the refill cartridge 120 and the refill cartridge 120 is inserted into the base 102. The cover 104 with insert ring 154 is placed over the base 102 to form the housing. Once activated, the fan 156 directs air through bottom air inlets underneath the base 102 and through the housing as pushed by the fan until it reaches the top orifice and exits the housing. Air flows are shown in FIG. 24.

The fan 156 is shown located generally near or slightly below the midline of the base. A suitable location of the refill cartridge 120 is directly above the fan 156 or as close as practical to the fan 156. In an alternative configuration, the cartridge is placed below the fan or in a different position that still utilizes air flow to push air and thereby release scent from the cartridge.

Controller

In the example shown, a controller 182 is positioned vertically lengthwise rather than horizontally lengthwise to optimize passage of air flow up and around the controller 182. The controller 182 controls the fan 156. In addition to turning the fan 156 on or off, the controller 182 also controls the fan speed. The controller 182 may include settings so that the device turns on at intervals of time, for example, every 30 minutes, every 60 minutes, or every 90 minutes. The controller 182 may also provide the user with any suitable system including wireless communication, such as Wi-Fi or Bluetooth. This can be in conjunction with an app on a cell phone or tablet, or with a dedicated user interface. With wireless communication, the controller may be in communication with any suitable device to provide data or user input. For example, sensors (motion, chemical, particle, temperature, moisture, etc.) may be provided to signal an event or condition. The controller may be programmable to determine operation of the fan based upon sensor and user inputs, and the time.

The controller is programmable and can incorporate almost any suitable function for operating the fan and any optional light and other added components (e.g. LED, sound generator, sensor, etc.). With wireless communication combined with a user interface and any number of various devices, the fan can be regulated based upon time, environmental conditions, preset settings, and communications from the user. This allows the operation of the device to be efficient and power saving.

Accordingly, the battery can last a long time due to low power consumption by efficient control of the fan operation by the controller. In addition, the air flow path is designed for efficiency lowering power consumption. Furthermore, the present device does not require a heater, which is power hungry and inefficient for dispersing materials into the air. The device can operate for a long time without intervention or maintenance due to the long battery life, and the potentially large capacity of the refill cartridge, which is only limited by dimensions of the device. The device is stand-alone since it is battery powered, and wirelessly controlled and regulated.

The components of the device may be constructed by any suitable method, such as any one of or a combination of molding, milling, machining, bending, stamping, cutting or the like. The components may be manufactured of any suitable material which includes any one or a combination or composite of thermosetting or thermoplastic polymers that are synthetic or natural (polyethylene, polypropylene, nylon, etc.), metals (aluminum, steel, etc.), and/or wood.

The vaporization of the scent is assisted by the air flow, and not by a heater. Air flow is optimized by providing a straight upward vertical air flow up through and out of the device, with streamlining and construction to minimize friction and impediments to the air flow. Instead of increasing air flow with a larger fan, air flow is optimized by this streamlining, allowing a relatively low power consumption of the fan while maintaining a large air flow.

In tests of an exemplary prototype an air flow as high as 2.2 meters per second measured by anemometer near the exit was obtained. Due to the inner wall design directing air flow out the top opening, the device almost works like a blow gun. Despite a relatively small size of the device, the fragrance/room coverage is quite significant. It is expected that a higher air flow and air speed can be obtained by optimizing the design and increasing the size of the device. The device can clearly be scaled up and down depending on where it is to be used and how it is to be used.

The device is easily maintained. Assembly and disassembly for maintenance, refill cartridge replacement, change of outer cover, can be accomplished by sliding components and locking components without the use of tools or other like assists.

Alternatives

Turning to FIG. 25, an alternative device is shown that includes side air inlets 264. The side air inlets go through a visible portion of the base that is not concealed by the cover or alternatively, through the base and cover, with respective air inlets in alignment. With side air inlets, air is pulled through the housing from the side air inlets rather than through the bottom of the base 202. The rest of the air flow is similar, being directed through the cartridge 220 to the orifice 208 of the cover 204. The insert ring may also be used 254 like it was before. The device need not be raised from the ground surface to draw air flow. An embodiment may include both side air inlets and bottom air inlets, in which case the device would still be raised from the ground surface. The controller 282 may be placed vertically as shown, however, it may instead be placed in other orientations. For example, a horizontal orientation that is below the side openings may be used to avoid obstruction of air flow.

Note that the air inlets, whether they be inlets underneath the base or side inlets, may be adjusted. For example, the inlets may include vents that allow the user to vary the opening size of the inlets and thus modify the rate of air flow. Other means of controlling air flow may be used as well.

Figure 26:
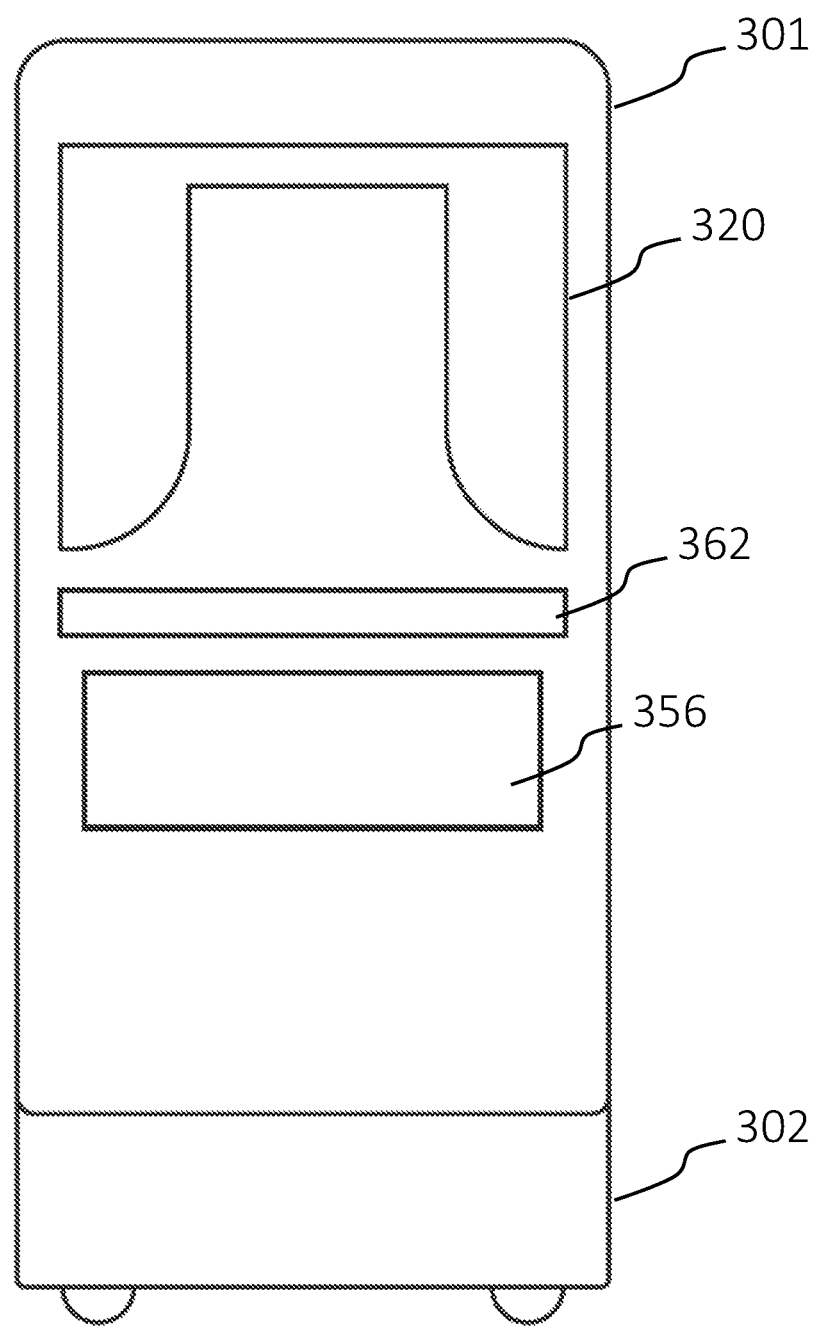
FIG. 26 illustrates a scent dispersion device with a filter.

A filter may be placed in an appropriate place to scrub the air. The directed air by the fan flows through the filter before or after it flows through the fan within the housing. In FIG. 26, an embodiment of the device is shown that includes a filter 362 positioned between the fan 356 and the refill cartridge 320. The filter 362 is configured to scrub the air before the air flows through the refill cartridge and out of the top of the housing 301. In this manner, the quality of air can be improved and allow inhalation and enjoyment of the scented air to be improved. The filter 362 is placed in the device in the same manner as the cartridge by simply inserting the filter 362 through the top opening of the base 302.

The filter 362 may have a friction fit against the sides of the interior walls of the base 302 to hold it in place. Also, an inner shoulder or radial flange within the base 302 may be used to support the filter 362, similar to the shoulder or flange that supports the cartridge 320. Alternatively, the filter 362 may rest against a protective covering of the fan 362. The filter 104 may be a replaceable, removable component.

Variations on the filter include the use of ionization, air cleaners, and/or air purification systems. The structure may include that the filter be positioned just above the fan, and then the other cleaning means, such as the ionization, air cleaner, and/or air purification system, be positioned just above the filter. The directed air by the fan may flow through the filter before or after it flows through the other cleaning means within the housing. Alternatively, other stacking arrangements may be used. Also, one or more of the filter, ionization, air cleaners, and/or air purification systems may be combined as one or more units.

One or more of the other components may be replaceable and reusable like the filter. In some instances, one or more of the components may be used instead of the filter, in which case, they would by positioned just above the fan, below the fan, or in another suitable arrangement that is configured to provide air flow through the housing in a manner that still releases scent.

Figure 27:
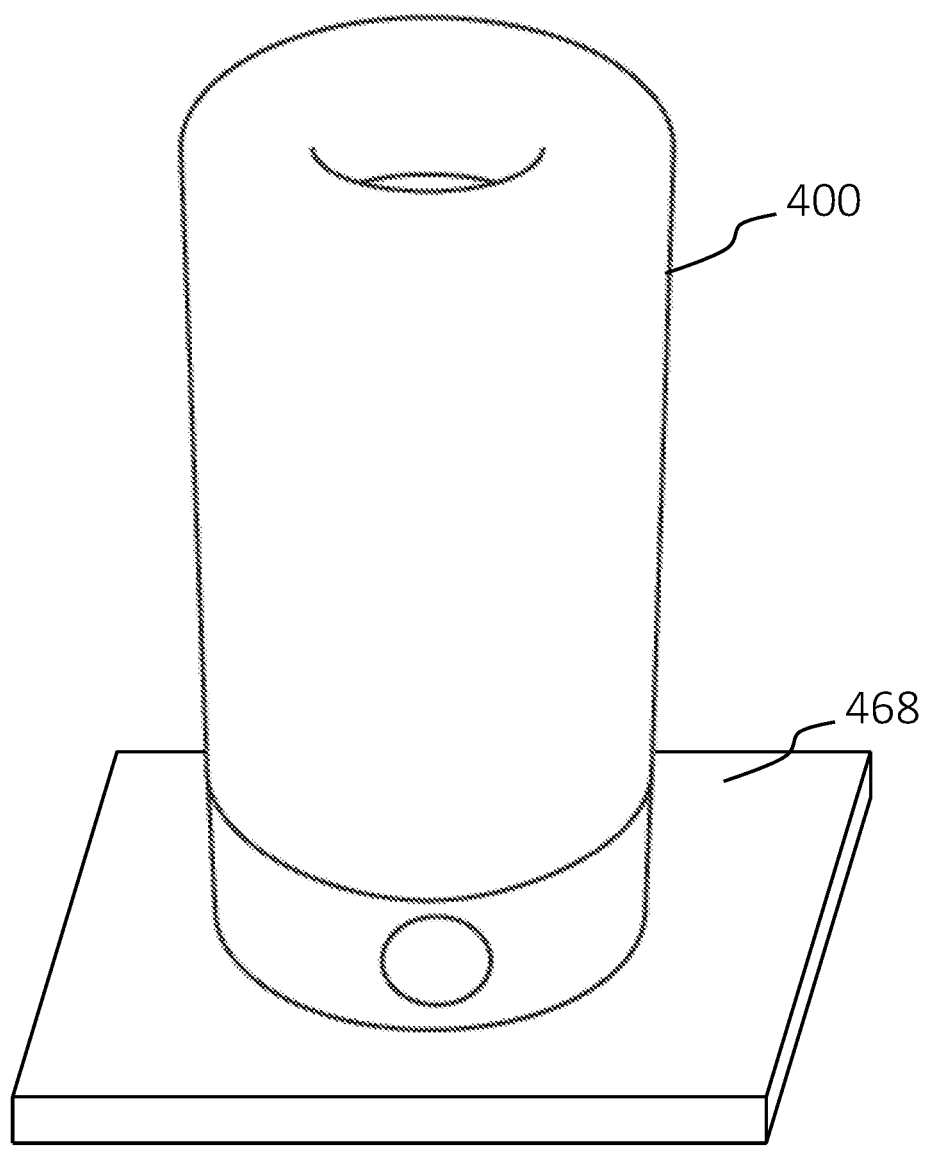
FIG. 27 illustrates a scent dispersion device including a docking station.

Turning to FIG. 27, the device 400 is shown with a charging dock 468 by which the device 400 may be charged. The charging dock 468 is a platform upon which the device 400 may be placed. The dock 468 may provide a flat surface, a recessed opening, or an inclined surface and have other variations commonly found in the art. Instead of a dock 468, a speaker charger or blue tooth speaker may be used to charge the device 400. Also, a wireless charging station may be used, such as a flat surface that the device 400 lays on and that allows the device 400 to charge wirelessly.

Figure 28:
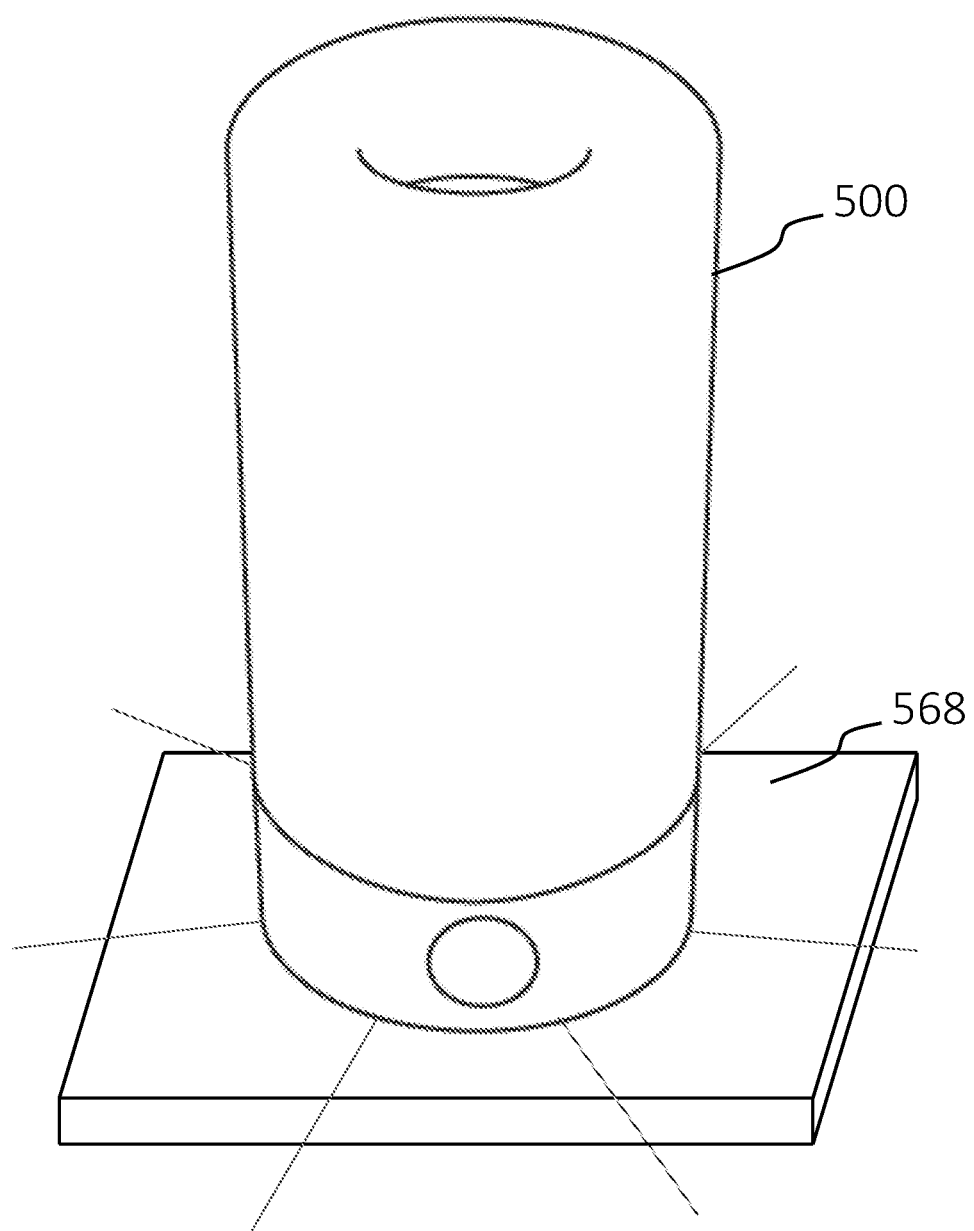
FIG. 28 illustrates a scent dispersion device including a docking station with lights.

The dock 568 may include a light-up feature with lights that light up as illustrated in FIG. 28. The dock 568 may light up when the device is connected to the dock or when the device is being charged by the dock 568. The dock 568 may light up depending on the type of fragrance in the cartridge. For example, each fragrance may be linked to a particular color, such that a certain shade of light lights up when an associated fragrance is being used in the device. Examples of associated lighting include purple lights to indicate lavender fragrance, light blue lights for linen fragrance, green lights for apple fragrance, and yellow lights for lemon grass fragrance. Not only does the light indicate the fragrance, but it psychologically reinforces or otherwise enhances the scent.

The dock 568 may also light up depending on the time of day. For a particular time of day, the dock may light up with a certain brightness, such as a bright light when it is daytime and a dim light when it is nighttime. The lighting is bright enough so that users can see it even during the daytime.

Besides a particular color, hue, or brightness, other types of lighting features, such as twinkling lights, blinking/solid, or lights shining in succession for a moving light effect, and other types of lighting may be used to indicate features of the device and communicate to the user.

Figure 29:
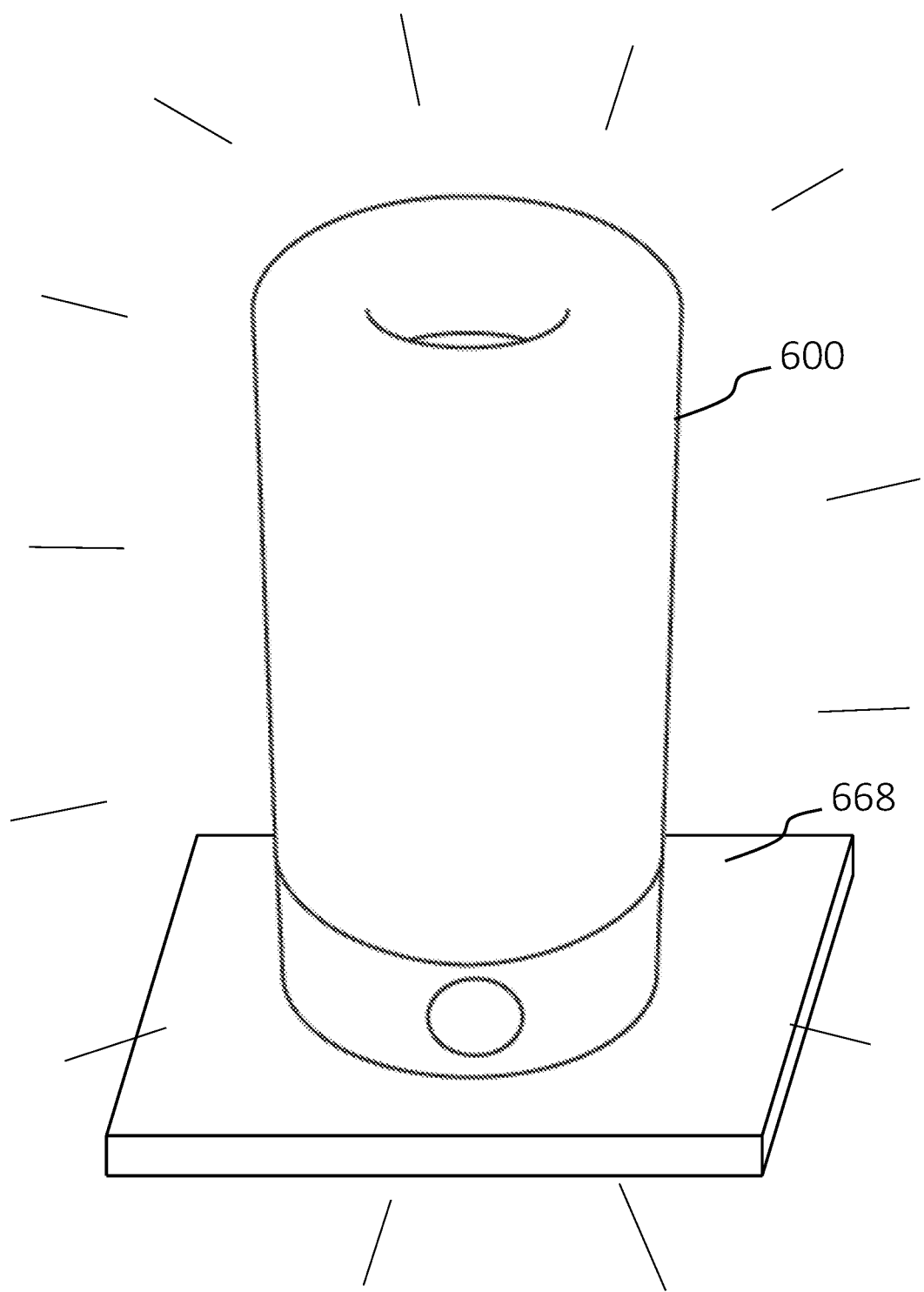
FIG. 29 illustrates a perspective view of a scent dispersion device with lights.

The device may include one or more lights that light up when the device is being used. FIG. 29 shows an example where the whole device 600 lights up. The dock 668 may or may not light up along with the device 600.

Figure 30:
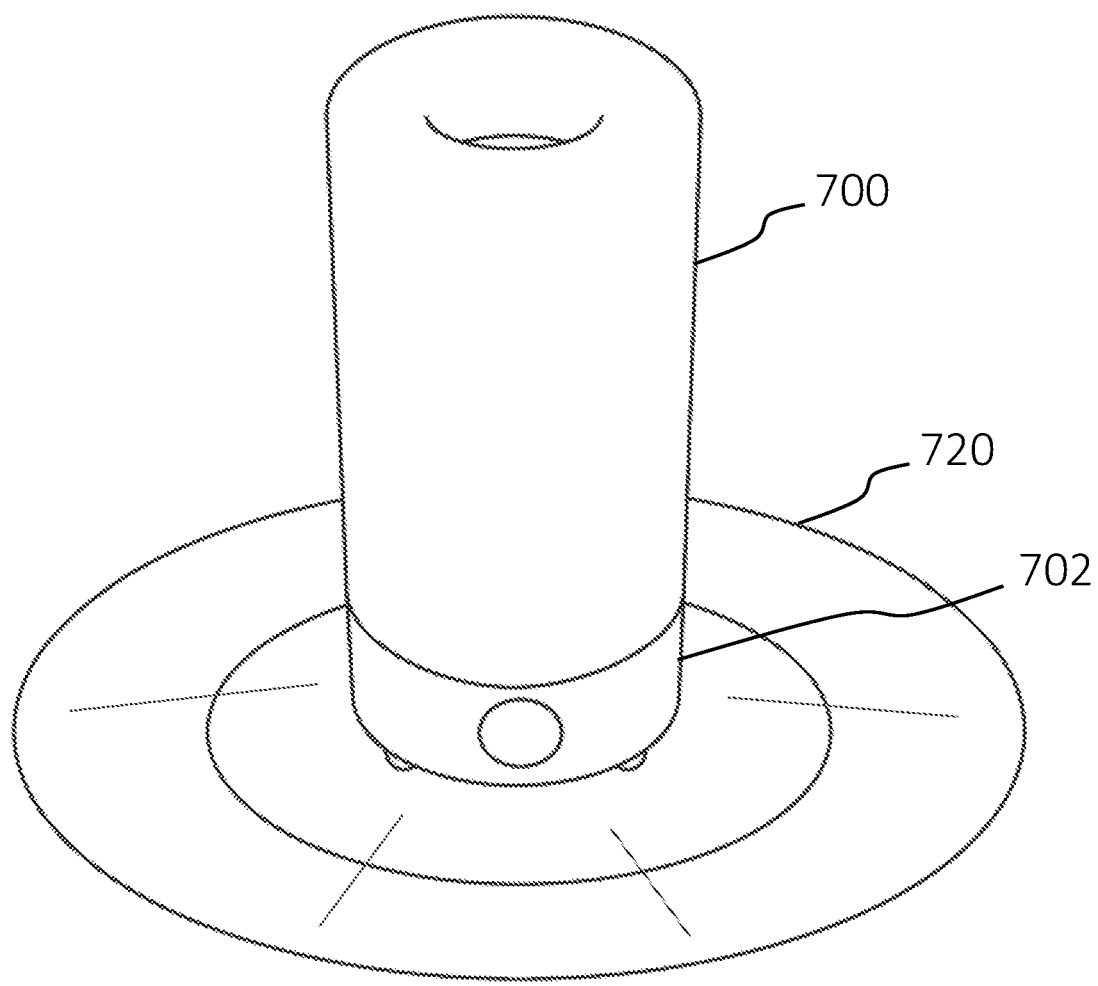
FIG. 30 illustrates a perspective view of a scent dispersion device with lights.

FIG. 30 shows the device 700 giving light from underneath the base 702. Lights from underneath the base 602 may light up in an evenly distributed manner around the device 700. Variations include that the dock also provide lighting that is evenly distributed in the same manner.

Figure 31A:
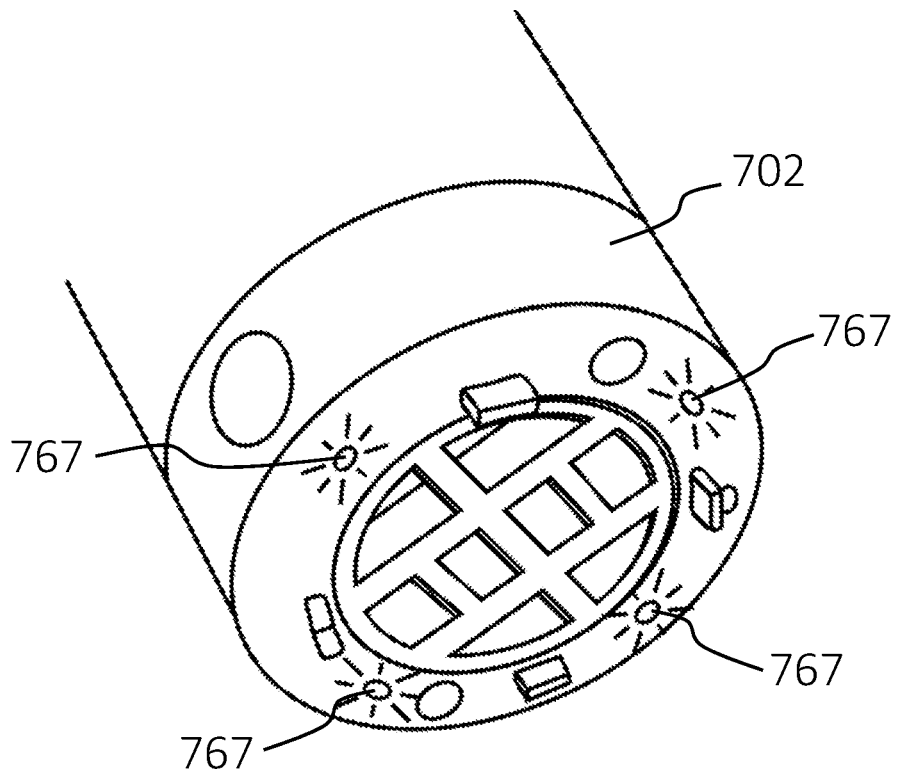
FIG. 31a illustrates a perspective view of a scent dispersion device with lights.
Figure 31B:
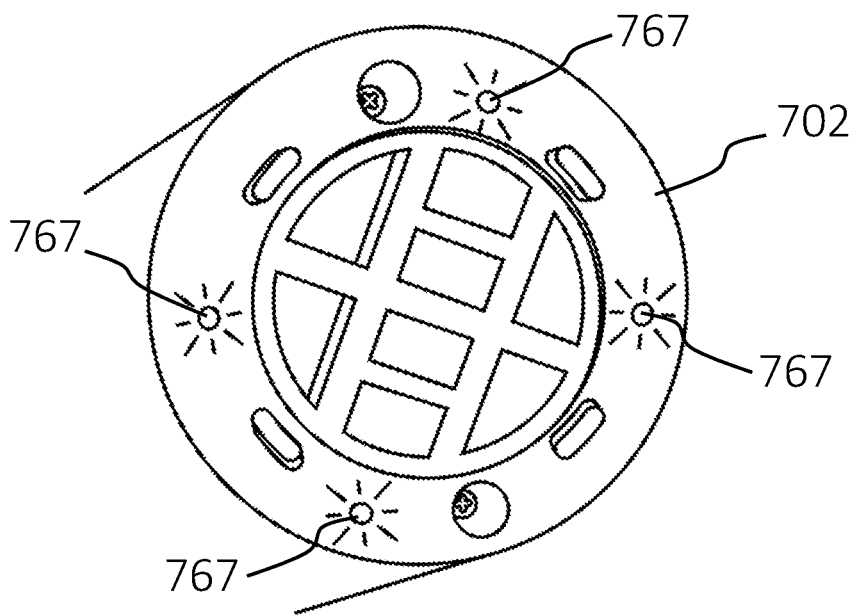
FIG. 31b illustrates a perspective view of a scent dispersion device with lights.

The lights may be LED lights, or other lights, that are located on the bottom panel of the device. Exemplary lights 767 are shown at opposite ends around edges on base 702 in FIGS. 31a and 31b.

Figures 32A, 32B:
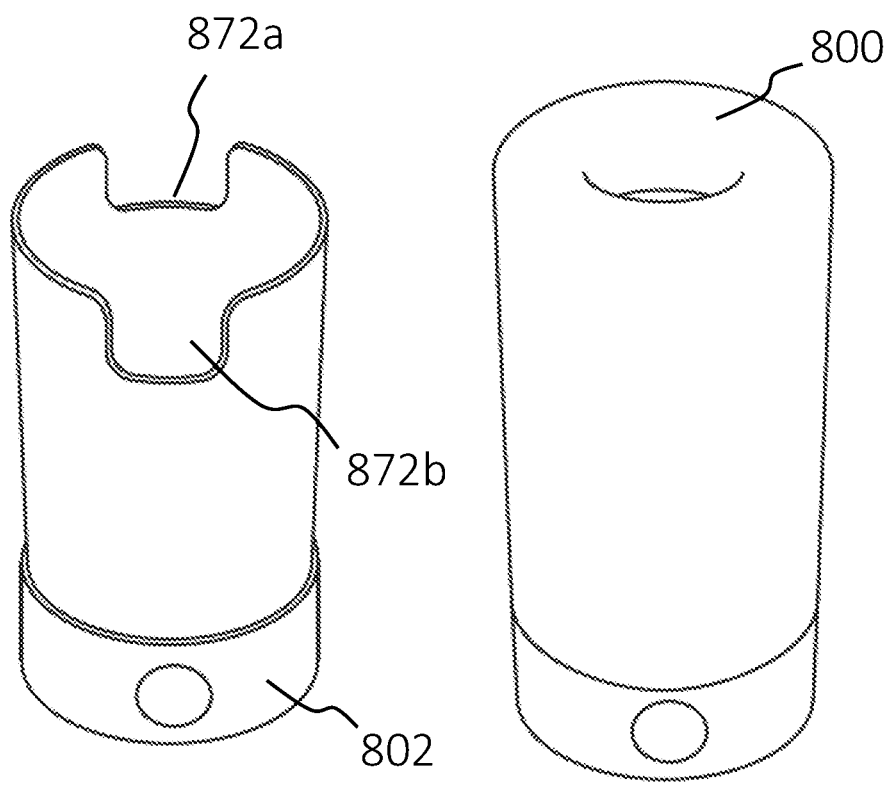
FIG. 32a illustrates a perspective view of a base with notches.
FIG. 32b illustrates a perspective view of a scent dispersion device.

FIGS. 32a and 32b illustrate a device 800 that includes a base 802 with notches 872a and 872b to allow the user to easily grasp the cartridge on opposite sides to remove a cartridge from the base. The notches 872a and 872b are defined by cutouts along the top edges of the base 802, the notches 872a and 872b being diametrically opposed from each other. The notches 872a and 872b have a depth that extend far enough into the base walls to provide gaps in the base that allow a user to use fingers to grasp part of the cartridge walls. The notches may extend to the base of the cartridge or farther. For example, the notches may extend to a filter located below the cartridge. Because the walls of the cartridge are solid, air does not readily escape through the notches 872a and 872b.

Figure 33:
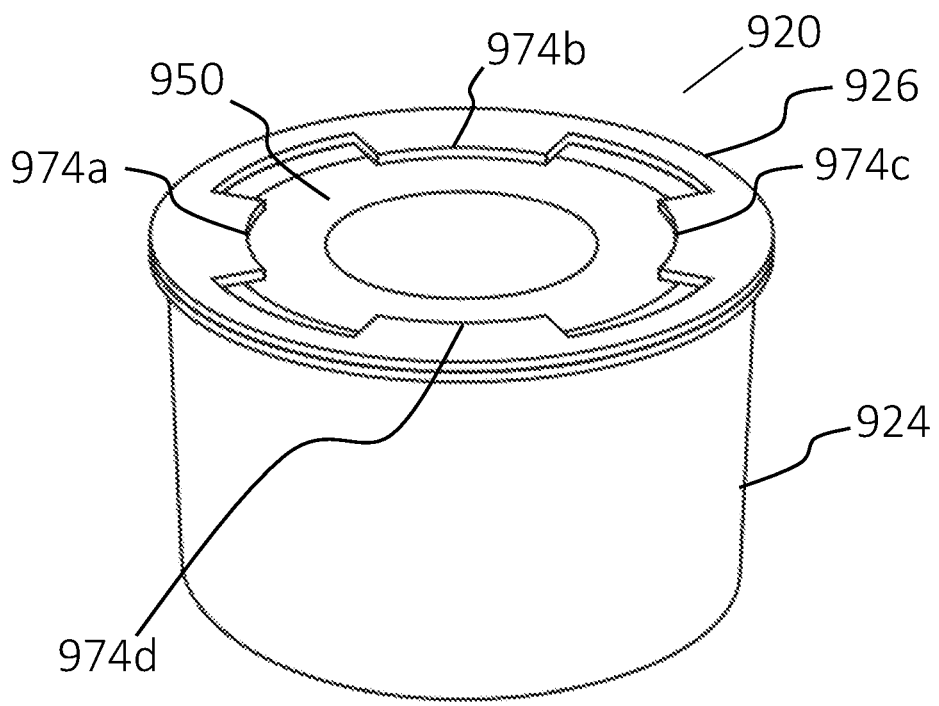
FIG. 33 illustrates a cartridge with locking tabs.
Figure 34:
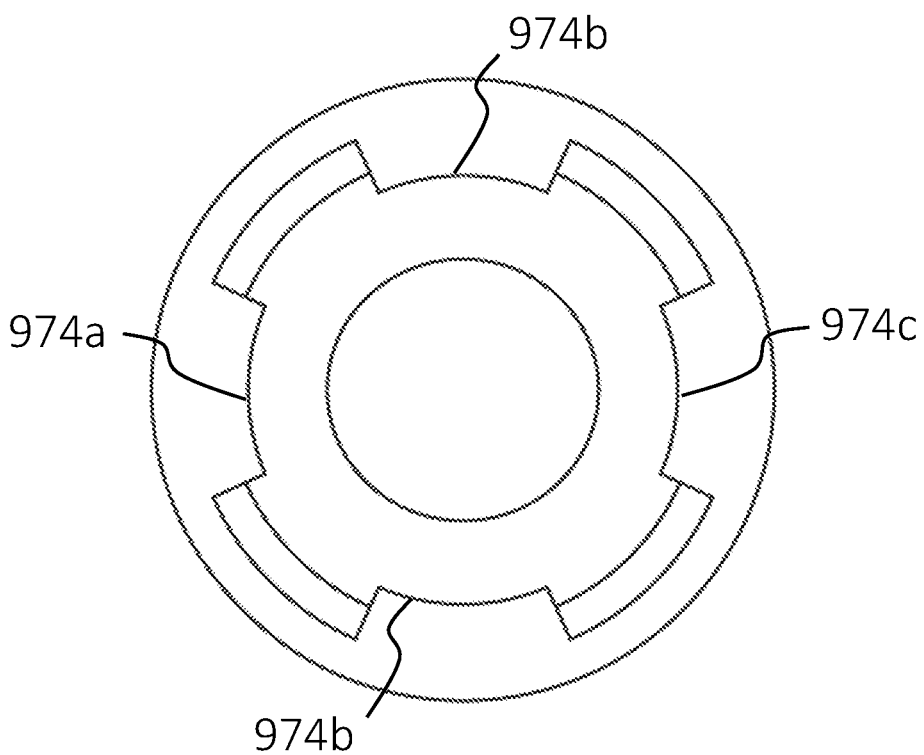
FIG. 34 illustrates a cartridge with locking tabs.

It may be desirable to keep the wick more securely held within the cartridge. FIGS. 33 and 34 illustrate locking tabs 974a, 974b, 974c, and 974d that hold the wick 950 inside the cup support 924 as an alternative construction for the cartridge 920. The tabs 974a, 974b, 974c, and 974d are elements that extend radially inward from the annular lip 926. They overlap edges of the wick 950 to hold it in place and make it difficult to remove from the cup support 924. They are of a flexible material which allow a user to still remove the wick 950 if necessary. For example, they may be made of the same material as the cup support, being molded as a natural extension of the annular lip.

Figure 35:
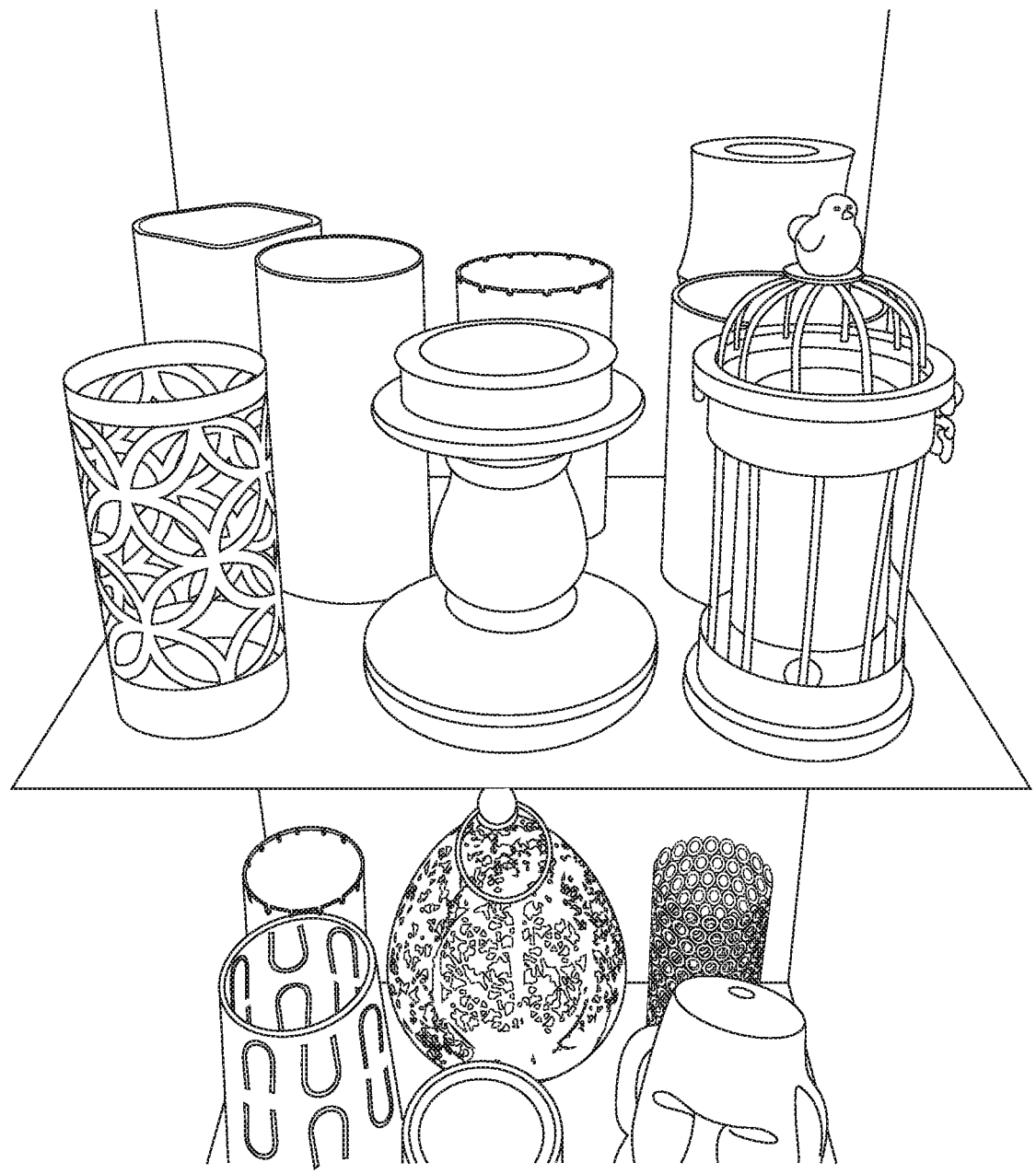
FIG. 35 illustrates a variety of decorative shells.
Figure 36:
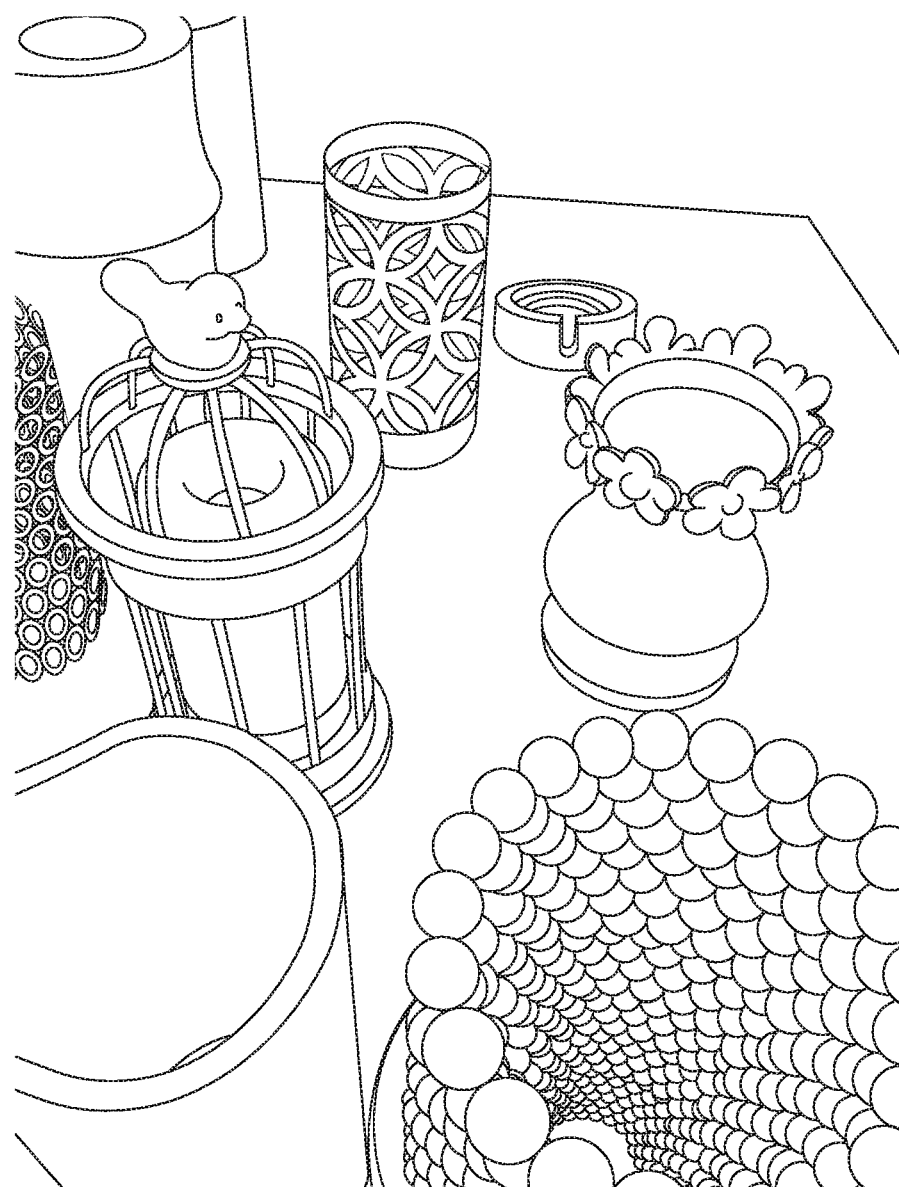
FIG. 36 illustrates a variety of decorative shells.

The cover may be plain or include one or more decorative elements. Alternatively, to provide additional aesthetic appeal and to comport with the décor of different rooms and color schemes, a variety of decorative shells that surround the device may be used. The shells may fit over the device, or contain the device within a shell housing. In some cases, the shells allow the device to be visible or partially visible. In other cases, the shells substantially obscure or completely hide the device. The shells may be of different sizes and shapes to add additional appeal and enable creative décor. The shell may be plain or may include several decorative elements, such as a sculpture, candle holder, model, etc. Examples of shells are shown in FIGS. 35 and 36.

The Kit

Figure 37:
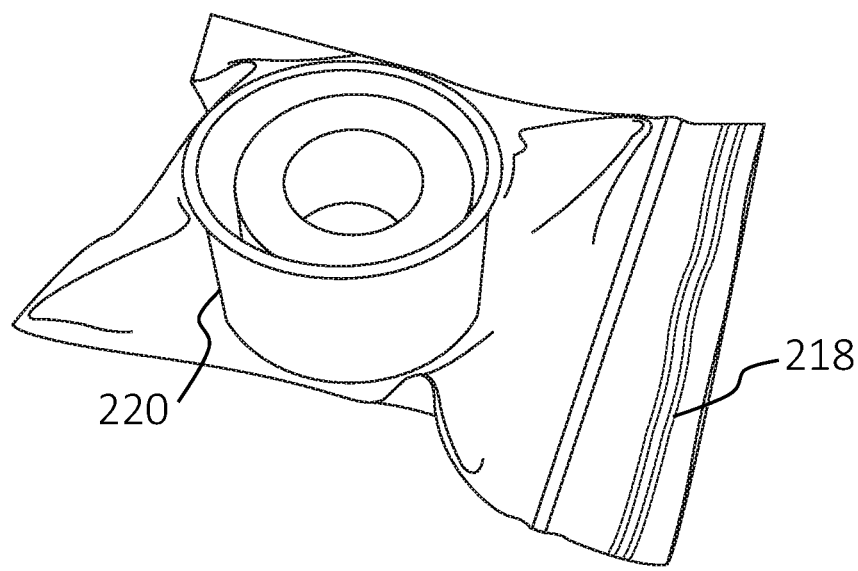
FIG. 37 illustrates a cartridge in a plastic bag.

As an alternative to top and bottom seals, the cartridge may be shipped and stored in conjunction with a container. As shown in FIG. 37, the cartridge 220 may be shipped, stored, and used in conjunction with a plastic bag 218. The plastic bag may have a removable seal, such as a sliding mechanism found in common plastic bags.

Figure 38:
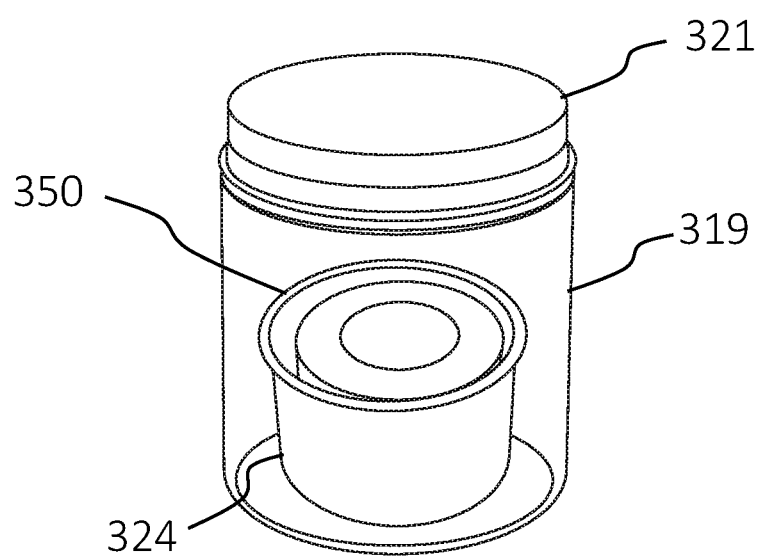
FIG. 38 illustrates a cartridge in a sealed jar with a lid.

The device may further include that the wick or other type of porous material is configured to be used in a kit. The kit may include that the cartridge be put in a container with a removable lid, the removal of the lid providing an opening that allows scent to be naturally volatilized in the air. As shown in FIG. 38, an exemplary kit includes a cup support 324 and wick 350 that is contained within a jar 319 (e.g., plastic, glass, etc.) that has a lid 321 (e.g., plastic, metal, etc.). Liquid fragrance may be poured into the jar 319, the wick absorbing the liquid fragrance therein. Although the wick 350 is shown with the cup support 320 as part of a cartridge, embodiments include the jar without a cup support. With a means of closure, such as a lid shown, the release of fragrance is controlled. Various other containers with and without lids are anticipated for use.

Note that the engagement of the cover and the base may vary. While the cover is described as being a single element, variations include that the cover include two parts that wrap around the base and join at ends. The two parts may be joined by a hinge that allow the two parts to open and close around the base.

Also, a slidable engagement to the base may be replaced by the cover fitting over the base and being engaged to the base by a locking mechanism. Other variations are also possible.

Figure 40:
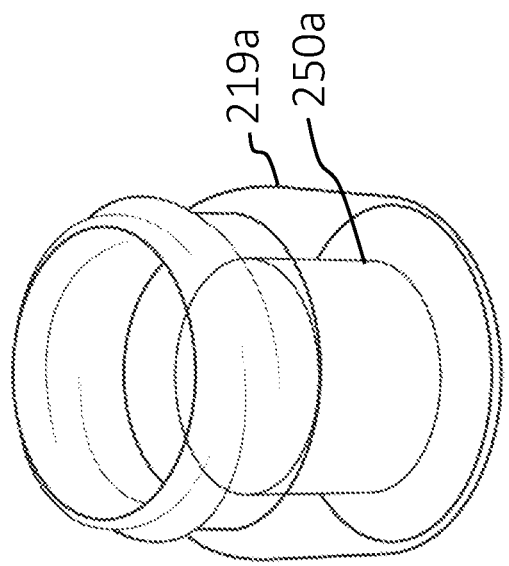
FIG. 40 illustrates a wick placed in an open jar.
Figure 39:
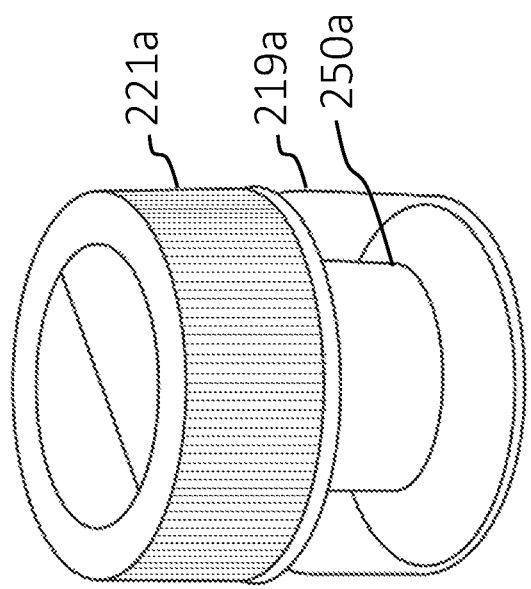
FIG. 39 illustrates a wick in a sealed jar with a lid.

FIGS. 39 and 40 show a jar 219*a* with a hollow interior that holds a wick 250*a*. The exemplary wick 250*a* has no central hole therethrough. To prepare the wick 250*a* with liquid fragrance, the wick 250*a* is placed within the cavity of the jar 219*a*. Liquid fragrance is then poured into the jar 219*a*. The jar height exceeds that of the wick 250*a* such that liquid fragrance does not spill outside of the jar before it is absorbed within the wick 250*a*. A raised outlet or other pouring mechanism may be used to pour liquid into the jar 219*a*.

A lid 221*a* may be used to seal the jar 219*a*. For example, the lid 221 may be secured with a snap, friction, twist, or other type of fit. The lid 221*a* may be any kind of covering that can be used to seal the jar 219*a* so that the liquid fragrance does not escape.

Mini Size

Variations may simplify the scent dispersion device to include more or less features than presented herein. An embodiment includes simply a single unit housing with a cartridge. The housing may consist of a base only. Alternatively, the housing may comprise two parts, a base and a cover. Various features discussed within the application may be included or not included. This allows the device to be smaller and more portable.

Figure 41:
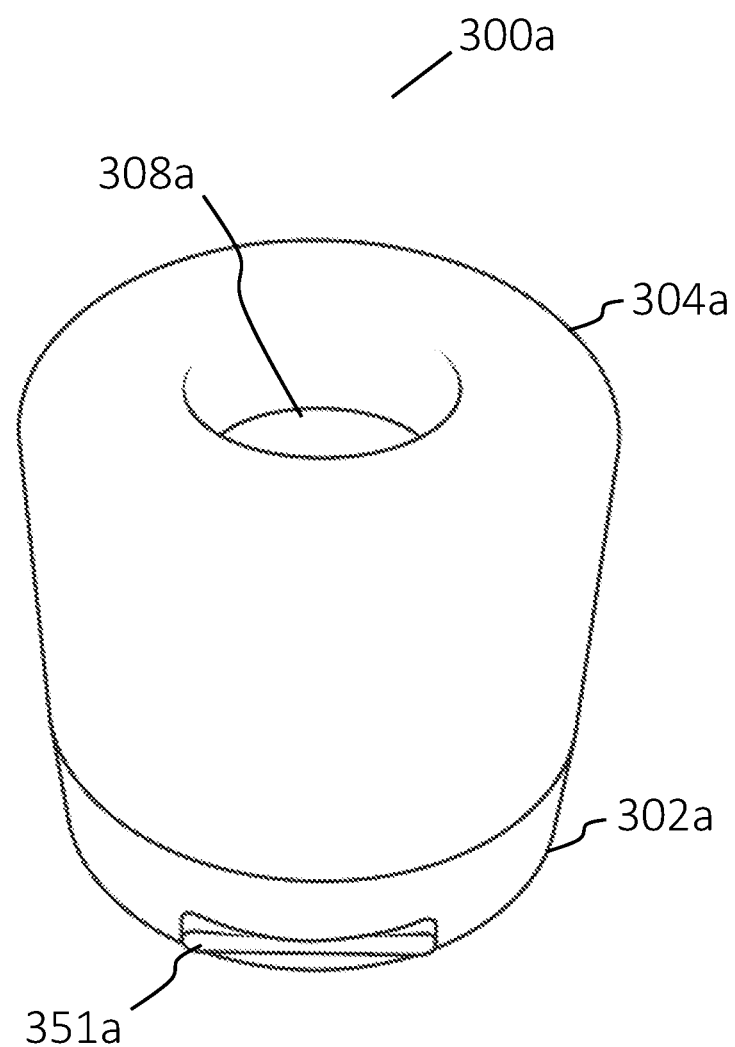
FIG. 41 illustrates a perspective view of a mini scent dispersion device.
Figure 46:
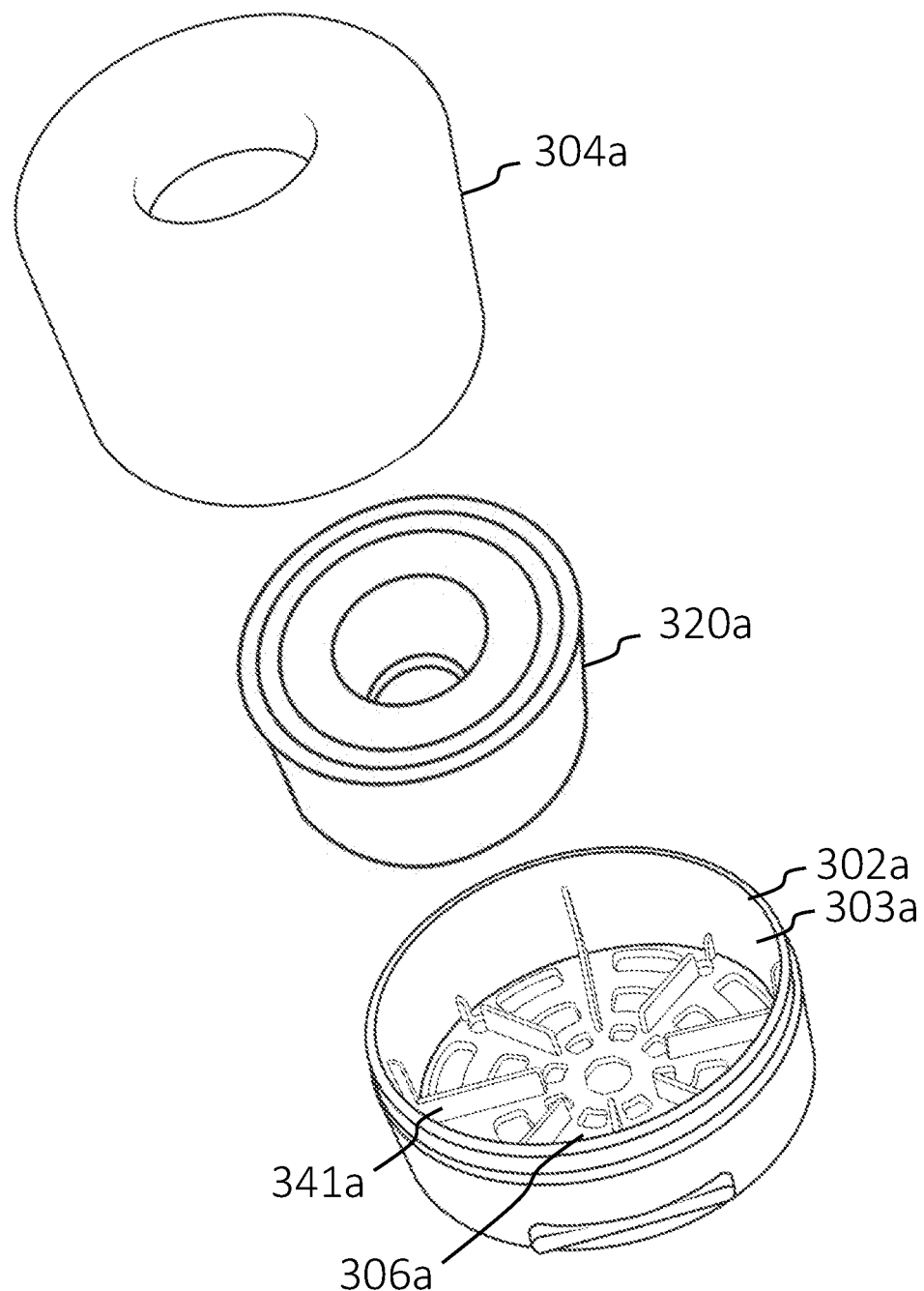
FIG. 46 illustrates an extruded view of a base, cartridge, and cover.

An exemplary mini device 300*a* as shown in FIG. 41 includes a base 302*a*, cover 304*a*, and orifice 308*a*. The base 302*a* is configured to hold one or more scent cartridges, however, it is simplified so as to include no fan and no battery. In addition, variations may include an exemplary side arm 351*a* as shown and which will be discussed in further detail below. With reference to FIG. 46, to assemble the device, the cartridge 320*a* is inserted into a cylindrical hollow of the base 302*a*. The cover 304*a* can be engaged and disengaged from the base 302*a* to allow a user to replace the cartridge 320*a*. The device may be used without the cover 304*a* and still be fully operable.

For the base, structure may include a shoulder as shown in FIGS. 2 and 3 or other restrictive means that stops the cover 304*a* from sliding any further on the base 302*a*. Contact between the cover 304*a* and the shoulder 305*a* completes attachment of base 302*a* to cover 304*a*. The cover 304*a* fits to the outer surface of the base 302*a* with a sliding or friction fit such that it can be easily attached and removed. The fully attached position of cover 304*a* and base 302*a* is shown in FIG. 41. An alternative attachment may include a snap fit or a screw type engagement with axial threads.

When the cartridge 320*a* is inserted into the hollow and a cover 304*a* is placed over the base 302*a*, there is an interior space defined between the top of the cover 304*a* and the top of the cartridge 320*a* in which air flows toward the orifice 308*a*. The air flow in the interior space can be improved by shaping or streamlining the interior space. For example, air flow may be directed outside of the orifice 308*a* by contours, such as angled and/or curved surfaces along the underside of the top of the cover 304*a*. This can be accomplished by molding a shaped interior during molding of the cover 304*a*.

Figure 42:
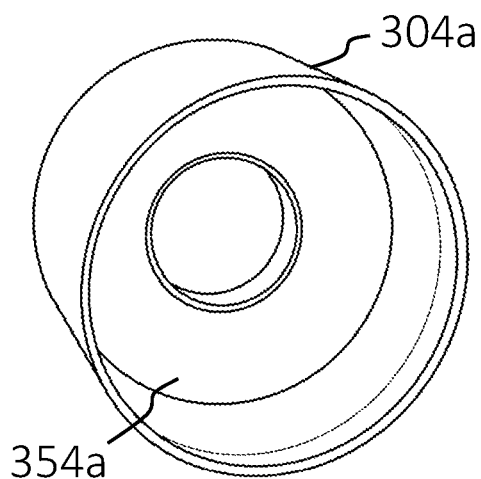
FIG. 42 illustrates a perspective view of a cover and an insert ring.

Turning to FIG. 42, an insert ring 354*a* is shown being used to direct air flow out through the orifice 308*a* of the cover 304*a*. Like insert ring 154, the insert ring 354*a* may be described as a flexible disc with angled sides and an axial hole therethrough. The insert ring 354*a* is inserted into the hollow interior of the cover 304*a* and pressed up against the underside of the cover 304*a*. In an attached position, the insert ring 354*a* is held in place underneath the top of the cover 304*a* by a friction fit or other attachment (e.g., bonded, screwed together, etc.). The hole of the ring is concentric with the orifice 308*a* of the cover 304*a*, the hole of the ring being similar in diameter. For example, the hole of the ring may be smaller in diameter to fit at least partially within the orifice 308*a*, be of the same diameter as the orifice 308*a*, or be slightly larger in diameter than the orifice 308*a* to fit around inner walls of the orifice 308*a*. An exemplary attached position of the insert ring and cover is illustrated in FIG. 42.

Figure 43:
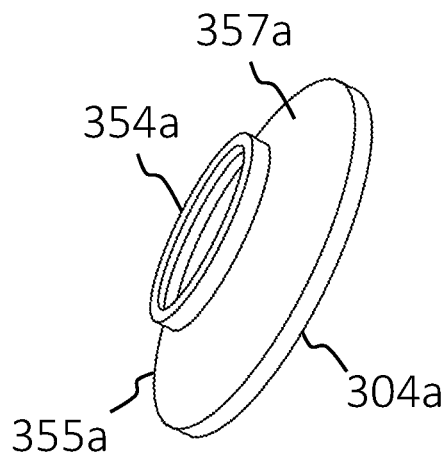
FIG. 43 illustrates a perspective view of an insert ring.

A perspective view of the insert ring 354*a* is provided in FIG. 43, the insert ring 354*a* having the same dimensions or scaled down dimensions of the insert ring 154 in FIGS. 9, 10, 11, 12. The insert ring 354*a* is defined by a ring wall 355*a* that can be inserted at least partially around or within the orifice 308*a* of the cover 304*a*. The ring includes a wing 357*a* that extends radially outward and slightly angles away from the ring wall 355*a*. The top surface of the ring wall 355*a* is generally flat, or may be rounded in a concave or convex manner. The bottom surface of the wing 304*a* is also generally flat or rounded in a slightly concave or convex manner. With the insert ring 304*a* in place, air pockets getting trapped within the top rounded dome of the cover 304*a* are prevented because the wing 304*a* covers the rounded concave or donut shape surface of the underside of the cover 304*a*, and is configured to direct air flow smoothly out of the housing.

Figure 44:
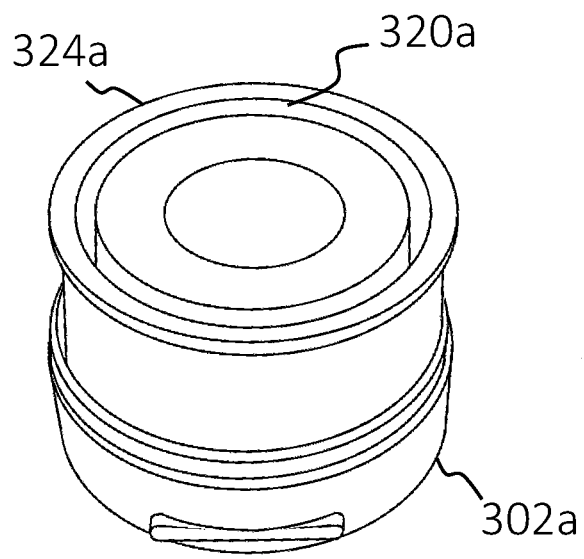
FIG. 44 illustrates a perspective view of a base with a refill cartridge.

Turning to FIG. 44, a refill cartridge 320*a*, including cup support and wick, is shown placed within base 302*a*. An exemplary embodiment includes that the refill cartridge 320*a* have a vertical height that is greater than the depth provided by the base 302*a*. This structure results in the refill cartridge 320*a* being taller than the sidewalls of the base 302*a*. This also results in the cartridge being easily removable and the overall device being smaller than the regular size device. Alternatives include a configuration like the one described above for the regular size scent dispersion device, with the cartridge 320*a* laying generally flush with the base 302*a*, as shown in FIG. 3. The fit of the cartridge 320*a* within the base 302*a* is a snug, friction fit.

The cover 304*a* is shown in FIG. 46. A suitable configuration is for the cover 304*a* to be a hollow cylinder with a dome-like top and that can be slidably engaged to the base 302a. The cover 304a further includes an orifice 308a for air to exit through after it is blown up and through the refill cartridge by the fan, the orifice 308a effectively serving as a vent that provides an air path to the outside environment. The orifice 308a may also include components (e.g., scented oils, liquids, etc.) to combine with the scented air exiting the device.

Figure 45:
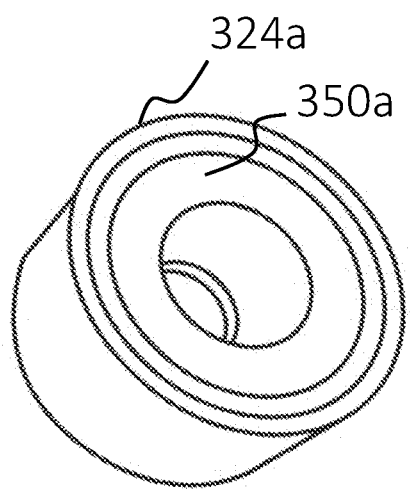
FIG. 45 illustrates a perspective view of a refill cartridge.

With reference to FIG. 45, the extruded view of the device indicates that the wick 350a is positioned within the interior space as defined by the cup support 324a. The wick can cup support may be the same as the wick and cup support for the regular device and shown in FIGS. 18 and 19, with the wick held in place by ridges and/or be partially supported by a support section and/or the constrictor. Variations include, however, that the wick be smaller in dimension. The wick 350a is centered coaxially within the cup support 324a, the hole of the wick 350a being generally aligned with a central hole of the cup support 324a. The same type of constrictor described for FIGS. 16 and 17 may be used, with the constrictor at least partially extending up through the opening of the wick 350a. The central hole of the wick 350a is generally in axially alignment with the funnel opening of the constrictor 342a.

Also, the outer diameter of the wick 350a is less than the inner diameter of the cup support 324a so as to leave a vertical annular space around the outer walls of the wick 350a. The space defined between inner walls of the cup support and outer walls of the wick provide for air pathways along the exterior wall surface of the wick 350a. The annular space provides air pathways that go from the bottom opening of the cup support 324a to the top opening of the cup support 324a. Air flows can travel along sidewalls of the wick 350a and within the interior walls of the wick. The contact between the exterior surface walls of the cup support 324a and inner walls of the base 302a is a friction fit, negating any space therein for air to flow.

With the inner hole of the wick, outer walls of the wick, and top and bottom surfaces of the wick exposed to air flow, the wick is configured for an even air flow distribution over the entire outer surface, or a substantial portion of the outer surface, of the wick, which results in efficient evaporation and optimal scent release through the top of the housing.

Additionally, the central hole of the cup support 324a and center hole of the wick 350a may be aligned with a central axis of the base 302a. Radial support flanges 341a are located on a bottom surface panel 306a of the base so as to support the cup support 324a. The flanges 341a are elongate members or ridges that extend upward from a bottom surface of the base, outward from inner sidewalls of the base 302a, or a combination thereof. A ridge on the bottom surface may form a continuous ridge with a ridge that extends upward on an inner sidewall. The ridges are spaced apart from each other so as to be able to support a cup support and raise it a height from bottom air inlets located on the bottom surface panel 306a of the base 302a.

Variations include flanges that only extend from the bottom of the base but that do not actually touch the interior walls of the base 302a. As shown, the flanges 341a may also have flange portions that extend at least partially upward along the interior walls of the base 302a. In this manner, the flanges may provide a friction fit engagement with the inserted cup support 324a. Variations further include that the bottom of the base include an annular ridge, or inner shoulder like the inner shoulder 141 shown in FIG. 6.

Figure 47:
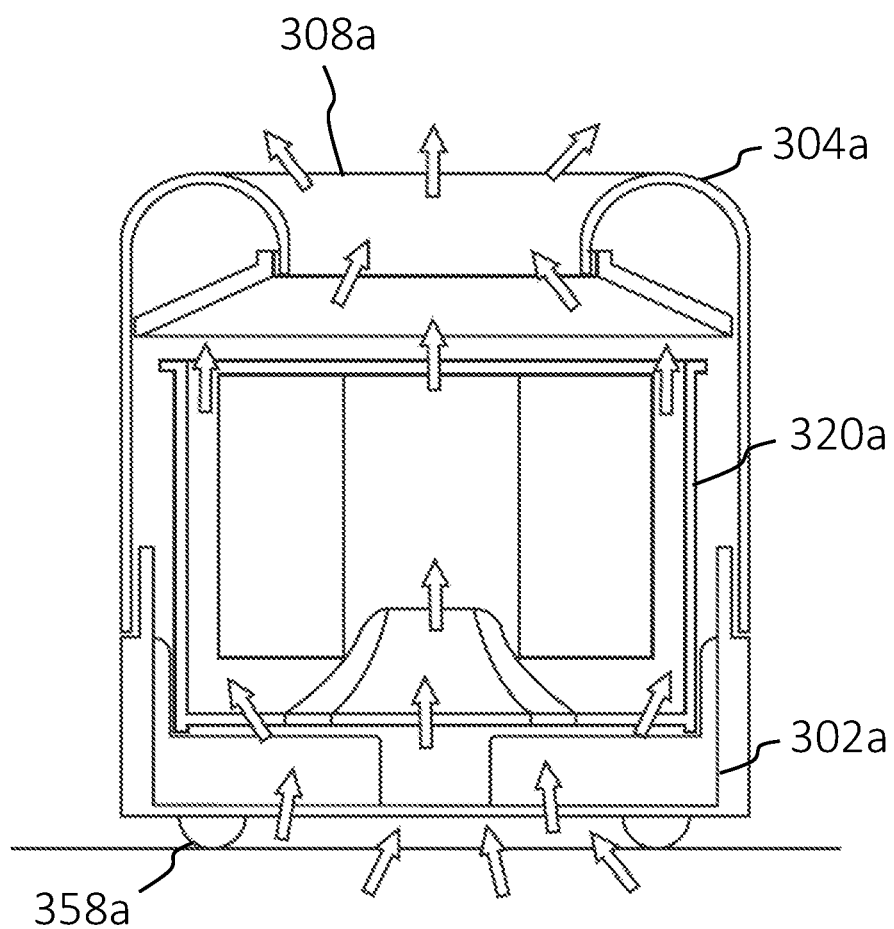
FIG. 47 illustrates air flows through a mini scent dispersion device.

The bottom surface panel 306a defines a plurality of air inlets in which air flow can enter the housing formed by base 302a and cover 304a. FIG. 47 depicts air flows that enter through the plurality of holes. Any type of air flows, such as air flows from ambient air or a fan placed underneath the device may direct air through bottom air inlets. The air flow arises from underneath the base 302a and through the housing as pushed by the air flows until they reach the top orifice and exit the housing. Air flows are indicated by arrows as shown in FIG. 47. The air flow may further originate from one or more air inlets located on side walls of the base 302a and/or cover 304a.

Passage of air flow from underneath the housing 101 may further be enabled by raising the base 302a above a ground surface level. An exemplary plurality of legs 358a are shown underneath the base 302a in FIG. 47. Each leg 358a extends downward from underneath the base 302a. The legs 358a are spaced apart so as to support the base 302a and allow for air flow. As shown, the legs 358a are spaced around the underside of the base 302a and are sufficiently narrow in width to allow air flow circulation underneath the base 302a. The plurality of legs 358a may raise the housing by a height. Non-limiting exemplary heights include 0.10-0.20 cm, 0.21-0.25 cm, 0.26-0.30 cm, 0.31-0.40, 0.41-0.50 cm, etc.

Another type of leg, attachment leg 373a, may be used to attach the device on a stand that includes a fan underneath the stand. The stand is configured to blow air up through the air inlets underneath the device. The side arm, leg, or combination thereof, may be used to align the device on a stand. With alignment, variations of the device with electrical or light up components may achieve an electrical connection with a stand and thereby receive power and control over those features.

An air inlet may be any one or more of an opening, vent, flue, shaft, duct, channel, passage, pipe, or pipeline. The panel 306a may be molded as part of the base 302a, or alternatively, the panel 306a may be a separate unit that attaches to the base 302a. The panel 302a is configured such that air may be directed up from underneath the base 302a and through the housing in a generally vertical direction.

Like the regular device that includes more features, the base and cover of the mini scent dispersion device are configured to allow easy removal and replacement of the scented refill cartridge. The cartridge is likewise configured to be easily removable and replaceable from the base. The cartridge provides structure to direct an air stream directed against the cartridge and disperse a scent into the surrounding environment. A suitable configuration includes a solid porous material in a cylindrical form, like the wick 350a shown in FIGS. 44 and 45.

An additional feature shown on the mini device 300a is a side arm 351a. The side arm may hook into openings of the stand to attach the device to the stand. When the device is laying on its side, the side arm 351a provides a flat surface that effectively prevents the device 300a from rolling.

Figure 48:
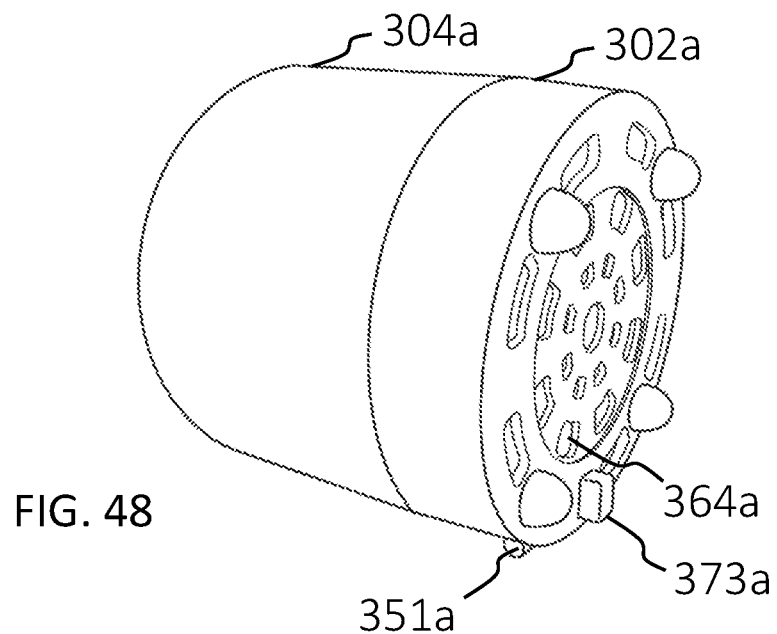
FIG. 48 illustrates a perspective view of a mini scent dispersion device laying on its side.
Figure 49:
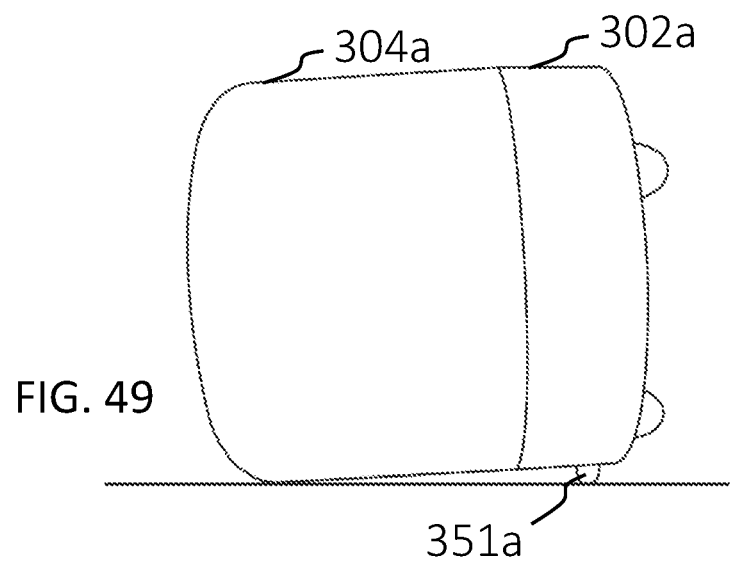
FIG. 49 illustrates a side view of a mini scent dispersion device laying on its side.

The side arm includes a ridge or elongate member that extends outward from the device 300a. The outwardly extending ridge includes a flat surface at its free end, the flat surface forming an offset tangent surface relative to the device 300a base. As shown in FIGS. 41, 48, and 49, side arm 351a is located on base 302a at or near the bottom end of the base 302a. Side portions of the side arm 351a jut outward so as to be in alignment with a middle of the side arm 351a and form a flat surface. The middle portion of the side arm 351a may be part of the surface, or in other words, flush with the surface of the device, and thus not be extended at all. The middle portion of the side arm 351a may instead be extended outward by a small distance, such as 0.1-1 mm, 1 mm-2 mm, 2 mm-3 mm, 3 mm-4 mm, and 4 mm-5 mm, or greater.

The side arm 351a allows the mini device 300a versatility such that it can be used standing upright or laying on its side. (see FIGS. 48 and 49). Air flow may thus flow in a horizontal direction through the device 300a. Having both horizontal and vertical positions lends the device 300a to being put in a plurality of places, and thus increases the versatility of the device 300a. Small places with short heights, for example, allow the device 300a to be placed horizontally, while narrow places with tall heights allow the device 300a to be placed vertically. The side arm 351a provides further advantages when used as part of the mega device, as discussed below. Note that a side arm 351a may also be included with a regular sized device.

Mega Size

In another variation, the scent dispersion device includes a tray 468a that holds a plurality of scent dispersion devices all together. Each device may have the same or different type of scented refill cartridge. Mix and match scents allow the user to create a personalized scent according to his or her desire. For example, each device may hold the same type of refill cartridge to create a strong scent. Alternatively, each device may hold a different refill cartridge to create a mixed scent.

Figure 50:
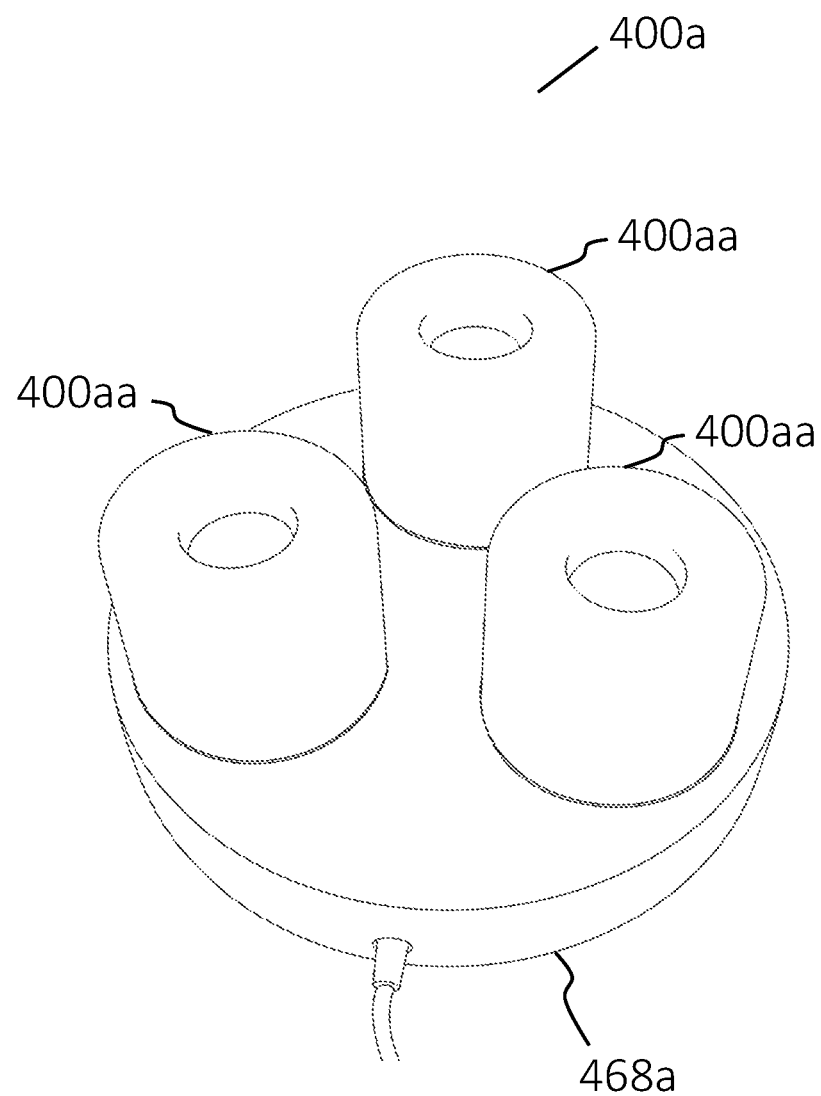
FIG. 50 illustrates a perspective view of a mega scent dispersion device.

The tray 468a in FIG. 50 is configured to hold a plurality of mini devices 400aa. As shown, three mini devices 400a are spaced equally apart around a round tray 468a. The tray 468a may be a stationary tray, or may be a lazy susan type tray that spins. To hold the mini devices 400a in place, the tray 568a may include recesses in which the mini devices are placed.

Figure 51:
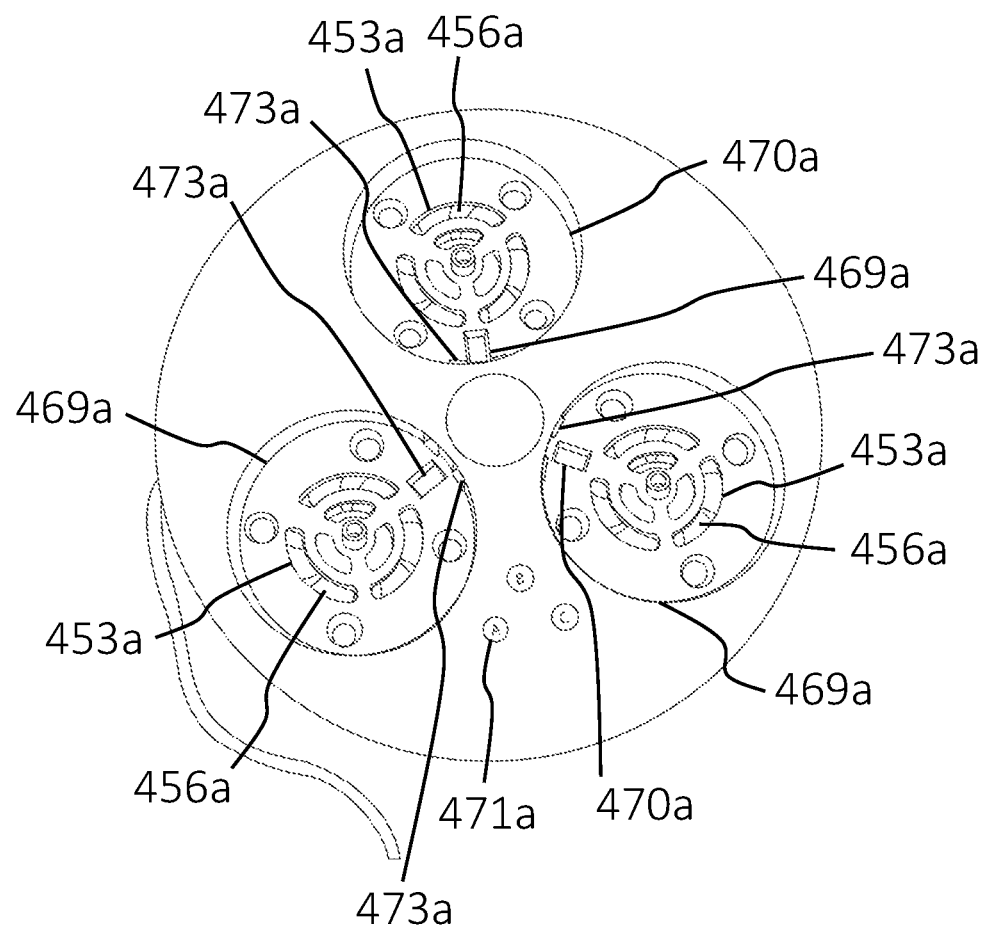
FIG. 51 illustrates a top perspective view of a tray.

FIG. 51 shows the tray 468a having recesses 469a, each recess having a fan 456a to blow air under a corresponding mini device 400aa. As shown, each recess includes a bottom surface that includes a plurality of holes 453a. Located below each recess is a fan 456a that is configured to direct air flows upward to enter air inlets underneath the mini devices 400aa.

The tray may be manually controlled by at least one manual control input, such as a push button or a touch screen display, that is physically located on the tray. For example, each button A, B, and C 471 shown in FIG. 51 corresponds to a distinct device on the tray. This allows a user to select which device is desired to be turned on or off and may further allow a user to perform other control as well. Additional buttons may be used, such as a button that activates and controls all of the devices at once. With one or more buttons, the device may further be manually programmed by pressing buttons in a prescribed manner. The buttons and button sequences used for the regular scent dispersion device may be incorporated into the tray control buttons. Additional control features are anticipated.

The tray may further be controlled by a controller in the tray as part of an automated scent management system where the controller controls one or more feature components of the tray. Computer-implemented access to the controller of the tray, whether it be a direct connection or by remote access (e.g. Bluetooth, etc.) allows the user to define settings or otherwise program the various feature components (e.g. time, lights, etc.). This allows the system to be independent and not require much, if any, user involvement. Like the scent dispersion device, the tray may include that manual control input be used to override automated control settings. The controller may control each device individually or control the devices together as a combination.

The controller may be attached or may be incorporated into the tray. The controller may further be configured to control any selected feature components of multiple scent devices in unison. Also, the controller may be configured to control any selected feature component of any single scent device, independent of control for other scent devices. The controller may be configured to control feature components of separate dispersion devices in an interdependent manner where control of any feature component in any scent device is conditional upon control, configuration, or definition. In one or more embodiments, the feature component is the same as the feature component in any one or more scent devices. For example, fan activation of one device may be controlled by a setting of a fan in another device. In one or more embodiments, the system feature component is different than the feature component in any one or more scent devices. For example, fan speed activation of one device controlled may be controlled by a fighting setting of a second device. In another example, the light in one device is only on when the fan is turned on in one or more of the devices.

Blending the scents by controlling each device separately or as a unit allows for a truly unique scent experience. For example, different scents can be made stronger with different fan speeds. Also, different scents can be diffused into the air at different times of the day according to set times. The possibilities promote scent creativity and enable personalized scent experiences.

With the mini devices removably inserted into respective recesses, air flows may be directed up through the mini devices and out into the external environment. Each fan may be controlled individually. For example, a variable fan speed may be controlled by a controller within the tray to control the scent intensity. This allows each mini device to have a different fan setting and results in a unique scent intensity that comes from blending the scents at different speeds.

Each mini device 400aa may lay within a recess on the tray 468a. Alternatively, attachment structure can be in place to secure the mini device 600b to the tray. As shown, each recess 469a includes a side arm cavity 473a, which is a hole or cavity located on an inner facing sidewall of the recess 469a. The side arm cavity 473a may actually be two small cavities that house end portions of a side arm 351a, with the center portion of the side arm 351a being flush, or approximately flush, with the device, the center portion fitting within the recess 469a without need for a side arm cavity 473a. The side arm 351a may be rigid such that it hooks into the side arm cavity 473a, securing the mini device to the tray 468a. The side arm 351a may exhibit resilient properties that allow it to be snapped into a side arm cavity 473a and effectively hold the device in place.

As shown, each recess 469 further includes an attachment cavity 470a. An attachment leg 373a on the underside of the mini device 400aa is insertably removed into the attachment cavity 470a. The attachment leg 373a as shown in FIG. 48 is an elongate member that is located underneath the base 302a and that extends outward from the base panel 306a. The attachment leg 373a may have a square or rectangular cross section and a flat end surface. Other shapes and sizes are also anticipated. The length of the attachment leg 373a may be the same as or shorter than the other legs 353a of the device. The insertion of the attachment leg 373a into the cavity 470a may be a loose fit, friction fit, or snap fit, the result being an aligned device with the tray in a suitable manner that further keeps the device in place with respect to the tray. Specifically, the attachment may prevent the device from rotating axially within the recess. A strong attachment, such as a snap attachment, may alternatively be used to prevent the device from being easily removed simply by lifting the device.

Electrical connections between the device and the tray may further be enabled with the attachment leg 373a being inserted into the attachment cavity 470a or the attachment of the side arm 351 into the side arm cavity 473a, with electrical connections on the device coming into contact with electrical connections on the tray. This may allow for light up features that may be on the device to be controlled, for example.

Figure 52:
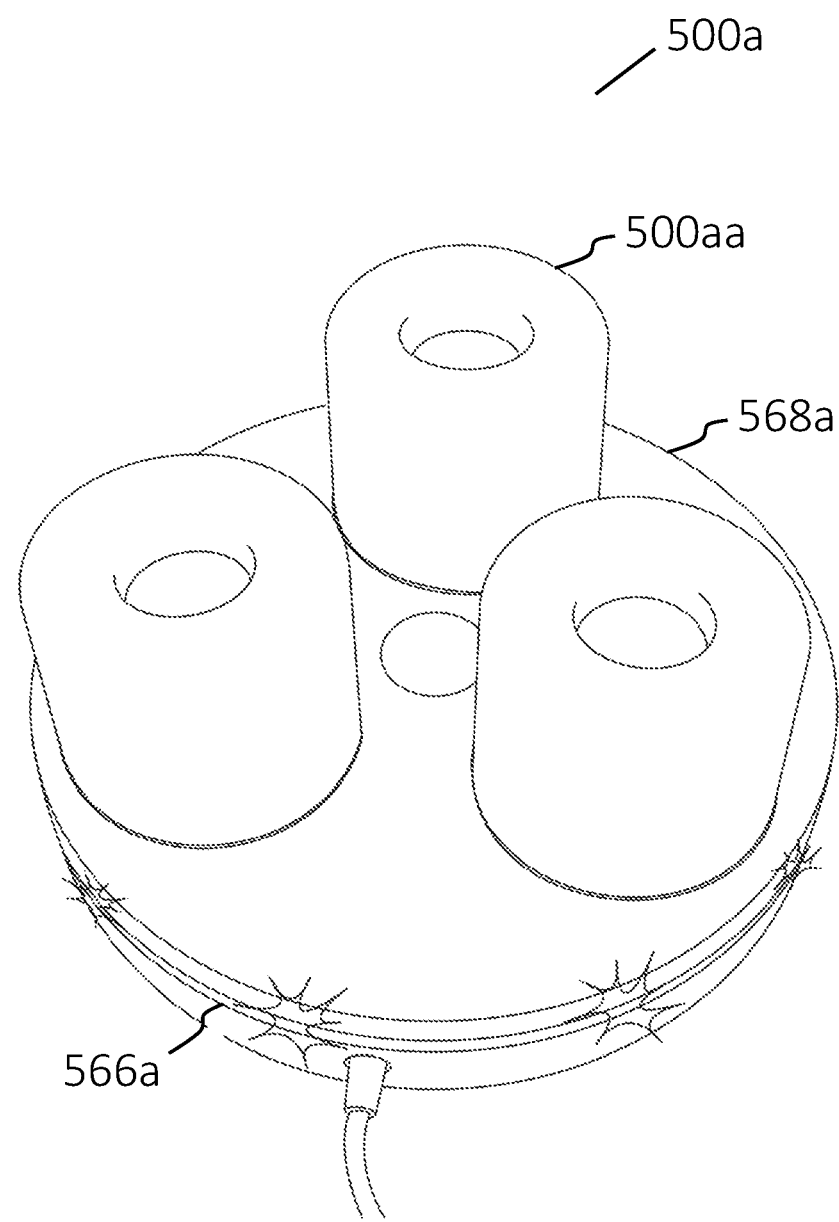
FIG. 52 illustrates a perspective view of a mega scent dispersion device that includes lights.

Turning to FIG. 52, a mega device 500 is shown with a tray 568a holding a plurality of mini scent dispersion devices 500aa. Furthermore, a lighting element 566a is included. An exemplary band of LED lights 566a is located around sidewalls that form the curved platform of the tray 568a. The band of LED lights 566a may be lit up according to manual controls, computer, controller, or other controls discussed herein.

The lights may light up when one or more devices is placed on or attached to the tray. The band of LED lights 566a may light up depending on the type of fragrance in one of the cartridges. Also, the band of LED lights 566a may light up depending on the time of day. For a particular time of day, the band of LED lights 566a may light up with a certain brightness, such as a bright light when it is daytime and a dim light when it is nighttime. The lighting is bright enough so that users can see it even during the daytime.

Besides a particular color, hue, or brightness, other types of lighting features, such as twinkling lights, blinking/solid, or lights shining in succession for a moving light effect, and other types of lighting may be used to indicate features of the device and communicate to the user.

A light or a set of lights may be associated with a particular cavity or a particular scent device, such that the lights reflect use of the respective cavity or of that particular scent device. The lights may light up when a device is being used. Lights may further be used to indicate whether one device, two devices, three devices, etc. is being used at a time.

Also, there may be multiple bands of LED lights that can be controlled. For example, a user may define a band of LED lights for a particular cartridge. In an example, one cartridge may be yellow, while another is green, and another is blue. Furthermore, the color of light may be associated with the fragrance of the respective cartridge. The lights may thus serve to indicate to others present what the mixture of scents is derived from.

The tray may be electrically powered or battery powered. Plugs and cords may or may not be used. The fan may be powered by a battery and controlled by a controller. With such a configuration, the battery and controller are contained in the housing at any suitable location, such as below the fan in a position configured to allow air flow.

The battery may be any suitable battery. A rechargeable battery is suitable and may include within the housing recharging circuits. The recharging circuit may include a plug in the housing for a charging jack, or a wireless inductive charging system. An embodiment includes that an electrical port be used so that the device can be connected to an electrical outlet for activating the device and/or recharging the device.

Device Hanger

Figure 53:
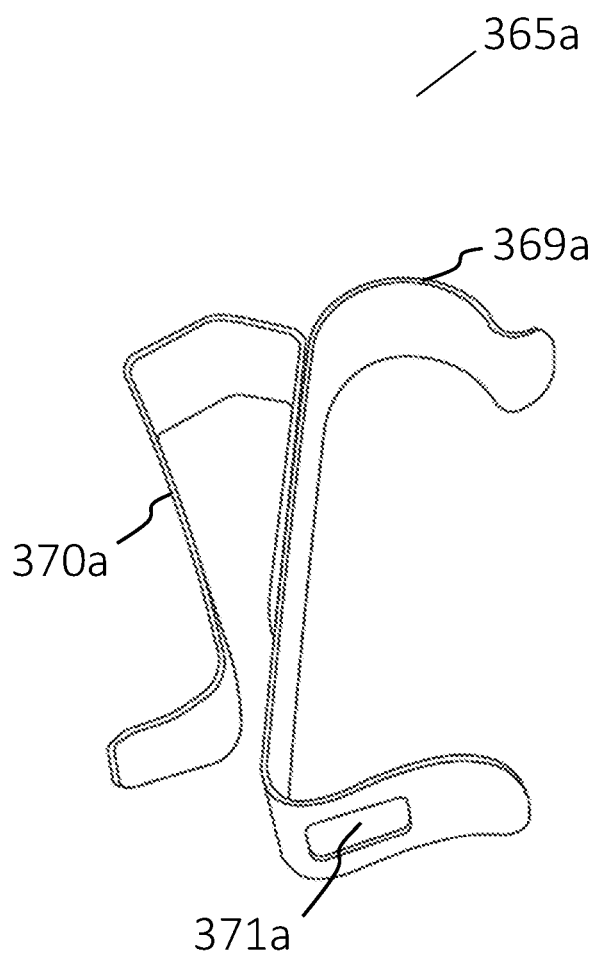
FIG. 53 illustrates a perspective view of a hanger.
Figure 54:
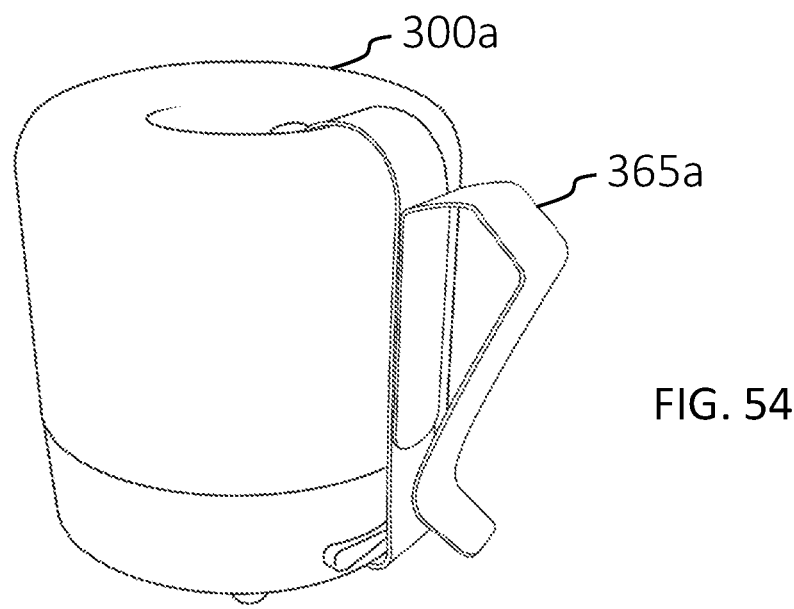
FIG. 54 illustrates a perspective view of a mini scent dispersion device with a hanger.
Figure 55:
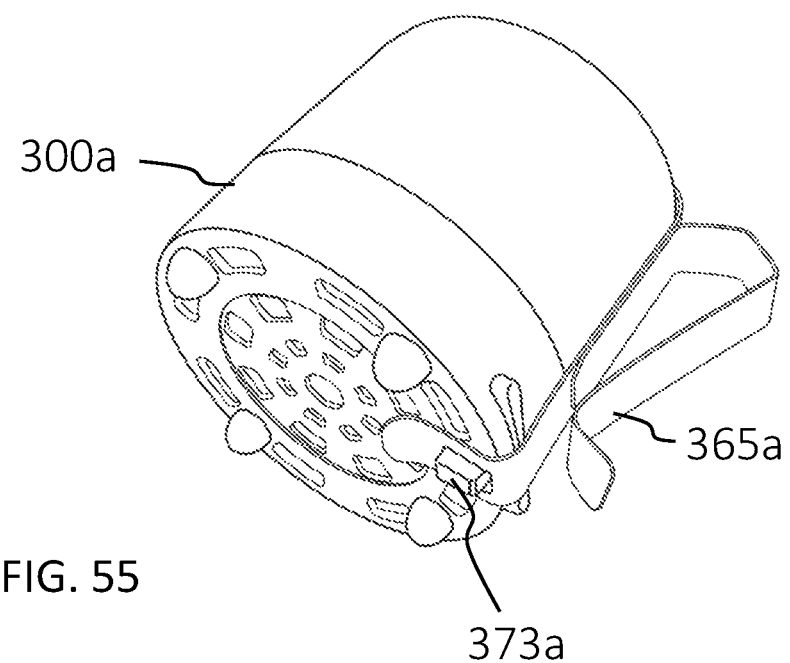
FIG. 55 illustrates a perspective view of a mini scent dispersion device with a hanger.

FIG. 53 shows a hanger 365a that can be used in conjunction with a mini device 300a to mount the mini device as a hanging fixture. The hanger 365a includes a double-sided hook 369a and a clip 369a. The hook 369a includes a generally flat elongate portion with two curved hook-like end portions. A first end portion is shown being curved to fit over a top surface of a cover and its interior portion. The first end portion further includes a free end that curves away from the curvature of the hook such that when the hook is mounted to the housing, the free end provides a small finger hold in which to pull the hook and remove it from the device.

The second end portion bends to conform to a bottom end of the base. For example, the end portion may bend at a 90 degree angle or approximately a 90 degree angle. The end portion may bend to conform to the curvature of the base. The end portion includes a hole 371a that is configured to allow the attachment leg to be removably inserted within the hole and create an attachment between the hanger and the housing. The hanger is thus wrapped around the device and secured to the device at both ends.

Figure 56:
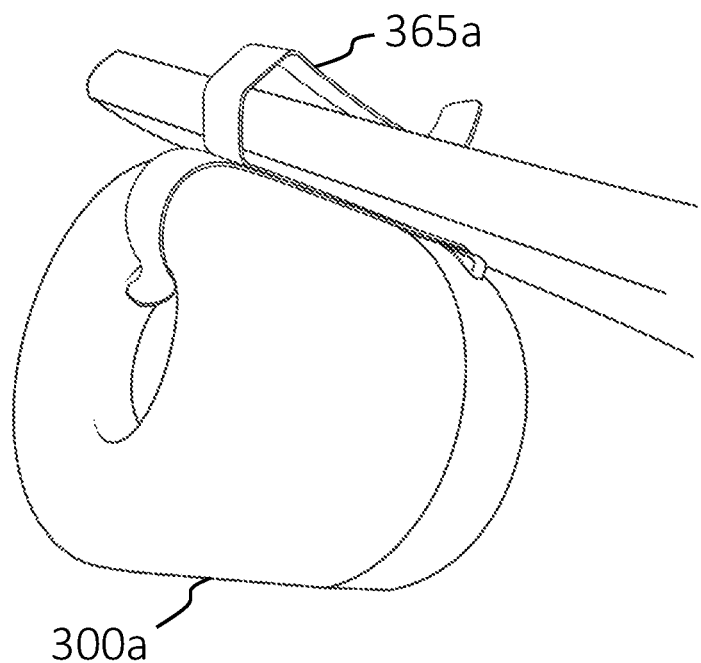
FIG. 56 illustrates a perspective view of a mini scent dispersion device attached to a sun visor.

On the side of the hanger 365a facing away from the device, a clip 370a is attached. The clip is a member that defines a wider section near its top and a narrow section at its free end such that it can grip whatever it is being mounted to. As shown in FIG. 56, the device is mounted by hanger 365a to a visor, such as a window visor of a vehicle.

Materials for one or both of the hook and clip include resilient properties that enable them to return to their initial shape after being stretched. The materials may include one or more of plastic, metal, or a combination thereof.

The Control

Figure 57:
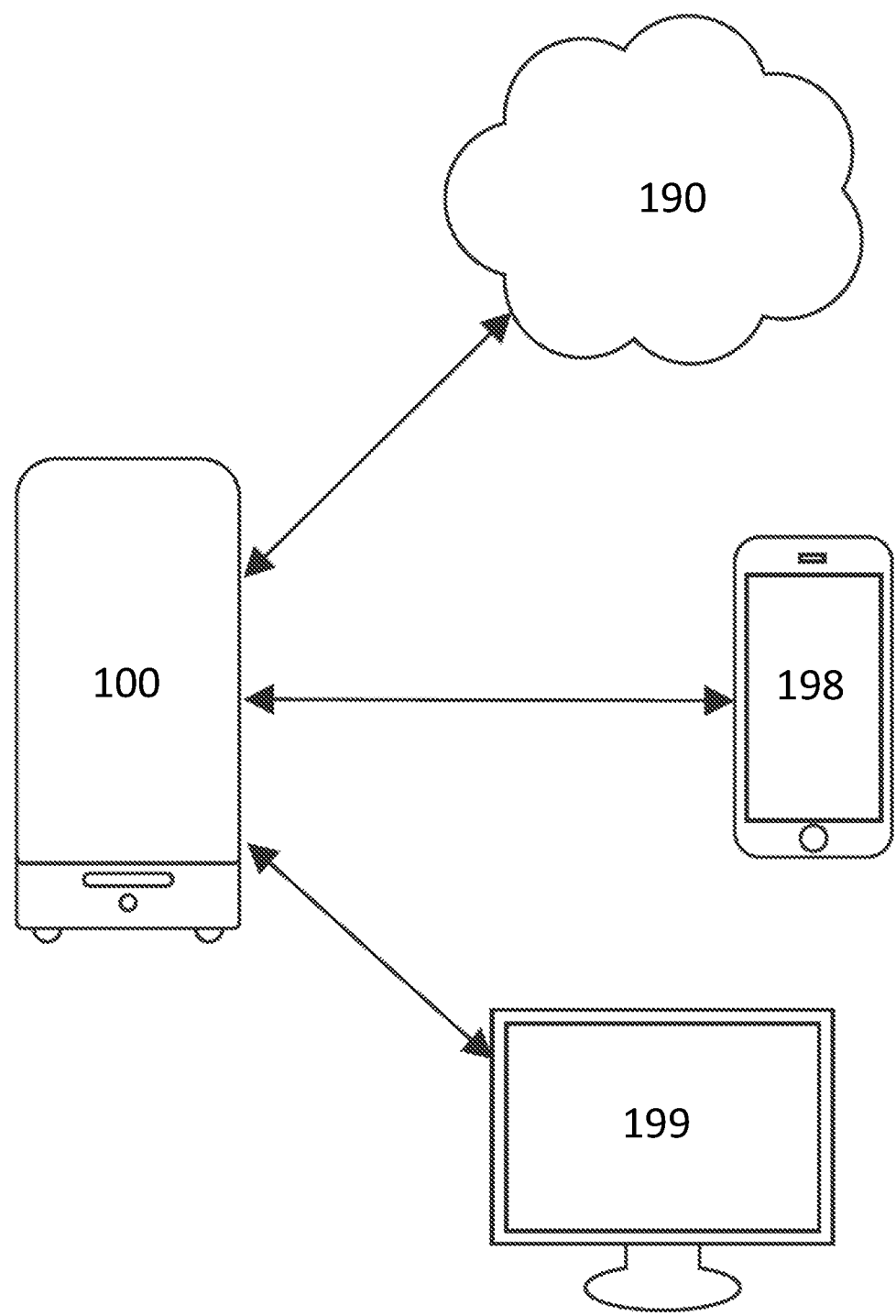
FIG. 57 illustrates a diagram of computer components used to implement features presented herein.

Turning to FIG. 57, a high-level overview is shown of various components disclosed herein that control a scent dispersion device and/or a tray used with a scent dispersion device. An exemplary device 100 is shown connected to a network 190, a computing device 198, and a presentation server 199. The device 100 shown represents a scent dispersion device, such as the scent dispersion device, mini dispersion device, and mega dispersion device, as well as any other devices, or components, described herein. The device 100 may be connected to one or more of the components shown. Variations include no established connection, however. With this connection, the device 100 may be controlled and communicate with the controller of the device 100 to program and reset features.

Presentation server 110 may comprise a computing device designed and/or configured to execute computer instructions, e.g., software, that may be stored on a non-transient computer readable medium. For example, but without limitation, presentation server 110 may comprise a server including at least a processor, volatile memory (e.g., RAM), non-volatile memory (e.g., a hard drive or other non-volatile storage), one or more input and output ports, devices, or interfaces, and buses and/or other communication technologies for these components to communicate with each other and with other devices. Computer instructions may be stored in volatile memory, non-volatile memory, another computer-readable storage medium such as a CD or DVD, on a remote device, or any other computer readable storage medium known in the art. Communication technologies, e.g., buses or otherwise, may be wired, wireless, a combination of such, or any other computer communication technology known in the art. Presentation server 110 may alternatively be implemented on a virtual computing environment, or implemented entirely in hardware, or any combination of such. Presentation server 110 is not limited to implementation on or as a conventional server, but may additionally be implemented, entirely or in part, on a desktop computer, laptop, smart phone, personal display assistant, virtual environment, or other known computing environment or technology.

The computing device 198 may comprise any computing device capable of receiving input from a user, including a mobile device, mobile accessory, smart phone, smart watch, personal display assistance, traditional desktop, laptop, tablet, and other devices.

The computing device 198 may be in communication with presentation server 110 via any communication technology known in the art, including but not limited to direct wired communications, wired networks, direct wireless communications, wireless networks, local area networks, campus area networks, wide area networks, secured networks, unsecured networks, the Internet, any other computer communication technology known in the art, or any combination of such networks or communication technologies. The computing device 198 may communicate with presentation server 110 via network 190, which may be the Internet, network, the cloud, virtual forum, or any other established software connection in the art.

The device 100 may further be in communication with an external source via any communication technology known in the art, including, but not limited to, direct wired communications, wired networks, direct wireless communications, wireless networks, local area networks, campus area networks, wide area networks, secured networks, unsecured networks, the Internet, any other computer communication technology known in the art, or any combination of such networks or communication technologies. Internet platforms may include Echo, Apple Homekit, and Google platform, for example. In a preferred embodiment, the device 100 is controlled by an application, or app.

Platforms used therein include hardware, browser, application, software framework, cloud computing, virtual machine, virtualized version of a complete system, virtualized hardware, OS, software, storage, and other platforms.

The computing device 198 may include an interface for display, such as a display found on a computer display, smartphone display, or other visual display. Displays further include holographic displays, 3D displays, virtual reality displays, or other displays. For representations that include audio formats, the computing device 198 may include speakers, digital sound makers, and other devices that are known in the art and that produce sounds in an electronically controlled manner. For representations that include tactile formats, devices that output tactile displays may be used. Input for a computing device 198 may include, but is not limited to, a keyboard, mouse, touchscreen, trackpad, holographic display, voice control, tilt control, accelerometer control, or any other computer input technology known in the art.

A control representation is presented in one or more of a visual, audio and/or tactile format presented to a user. Representations include static images (e.g., photos, drawings, graphical images) and/or dynamic images (e.g., video, computer-generated video, animated video, 360 video, augmented reality, virtual reality video, and/or any image with moving objects), audio recordings, and/or other types of representations, as discussed in further detail below. Note that TERs may be any of, or a combination of, a video, GIF, image, audio clip, icon, computer-generated image, artwork, or any other media representation. For visual representations, the displays for the visual representations include any kind of display, including electronic display, computer screen, phone screen, touchscreen, projected screen, virtual reality, virtual reality headsets, cardboard, mobile, or other type of display. The user audience may include one or more users, but may include non-human or otherwise automated users.

The displays for the visual representations include any kind of display, including electronic display, computer screen, phone screen, touchscreen, projected screen, virtual reality, virtual reality headsets, cardboard, mobile, or other type of display. The user audience may include one or more users, but may include non-human or otherwise automated users. A type of representation may include an image, a drawing, a GIF, icon, computer-generated image, artwork, photography, any other visual representation known in the art, or a combination thereof.

Figure 58:
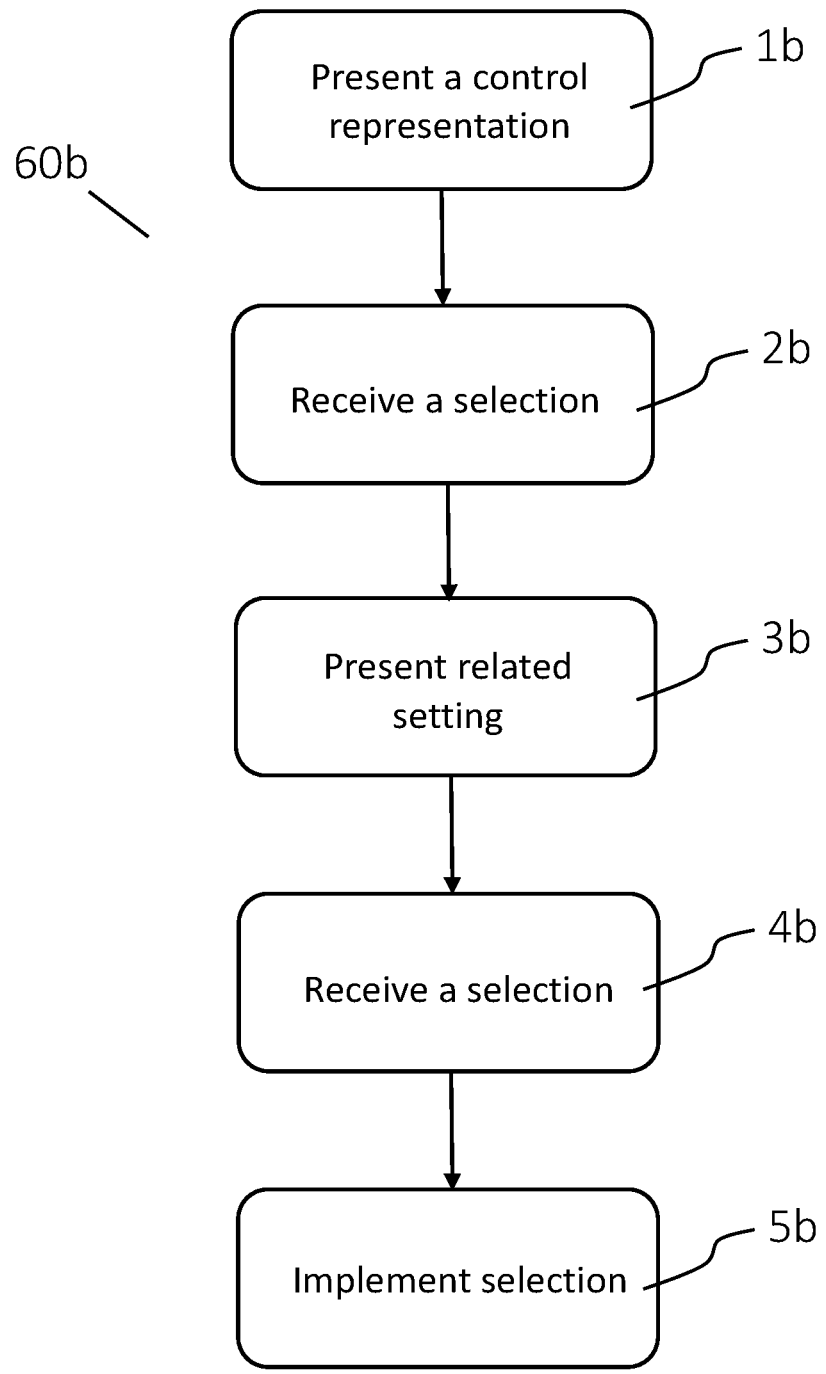
FIG. 58 illustrates a flow chart showing steps of an exemplary embodiment.
Figure 59:
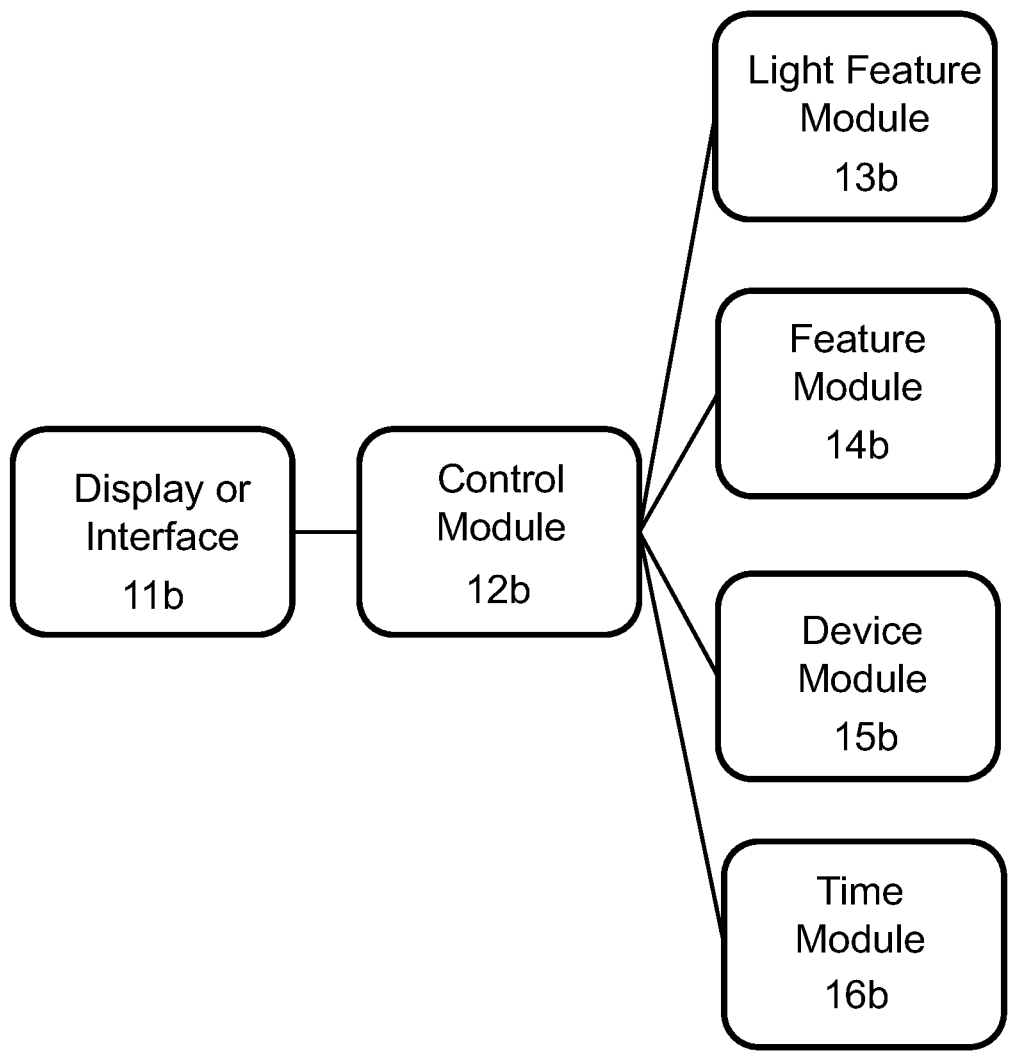
FIG. 59 illustrates a block diagram of modules used to carry out steps described herein.

Turning to FIG. 58, a flowchart 60b is shown illustrating steps for controlling features of a scent dispersion device. For purposes of explaining the flowchart 60b, steps will be described generally in relation to FIGS. 57-65. As discussed, FIG. 57 illustrates an exemplary computing environment as used herein. FIG. 59 illustrates an exemplary diagram that includes various modules used to control the device. FIGS. 60-65 illustrate exemplary display screens used in conjunction with a device.

A first step 1b as shown in FIG. 58 includes presenting a control representation that may be selected to allow for a subset of setting representations to be displayed. The control module 12b shown in FIG. 59 causes the display or interface module 11b to display at least one control representation on a display. The display is controlled by the server 199, device 194, electronic device 198, or internet command 190.

Figure 60:
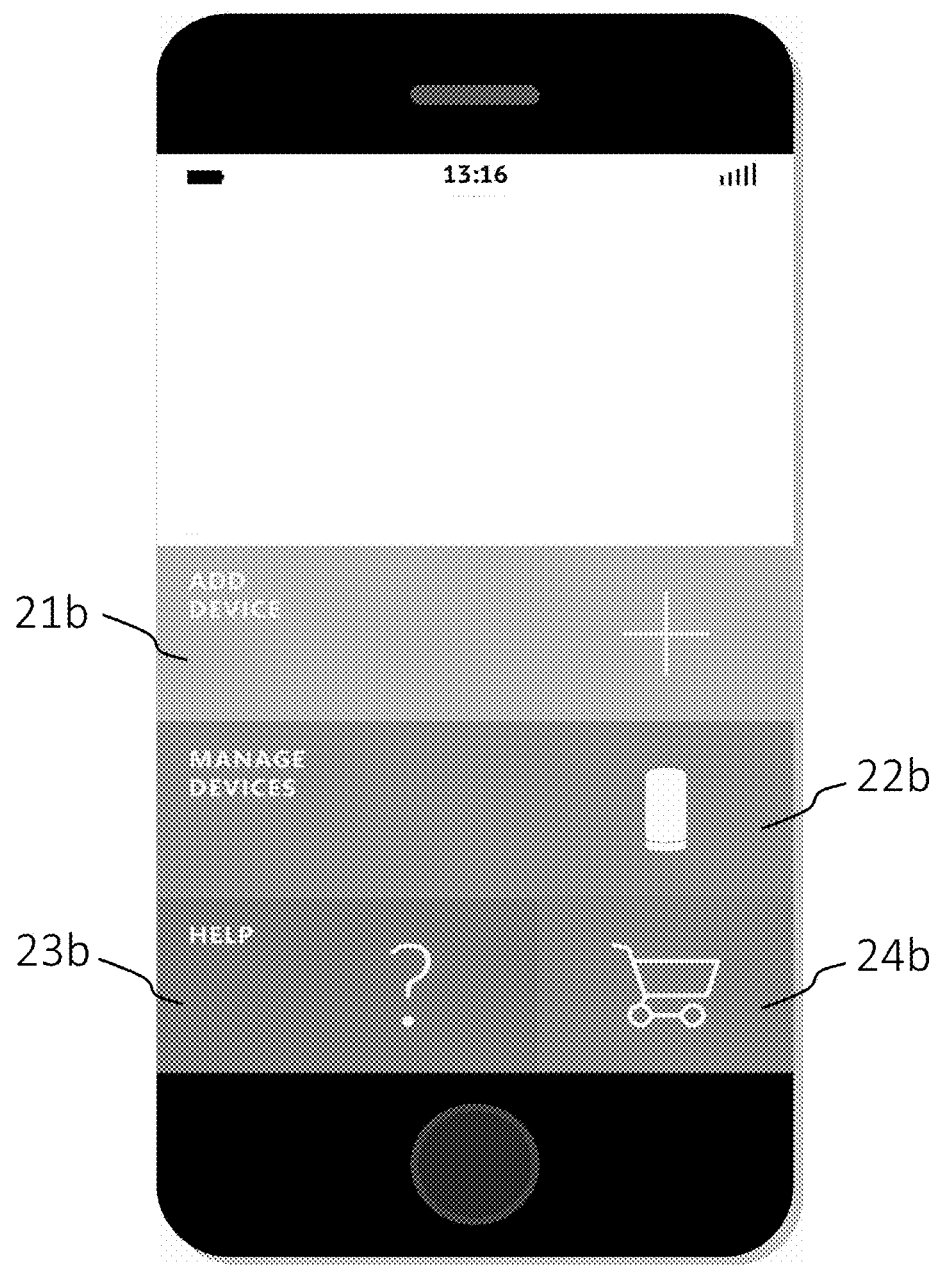
FIG. 60 illustrates an exemplary display user interface of a mobile device.
Figure 61:
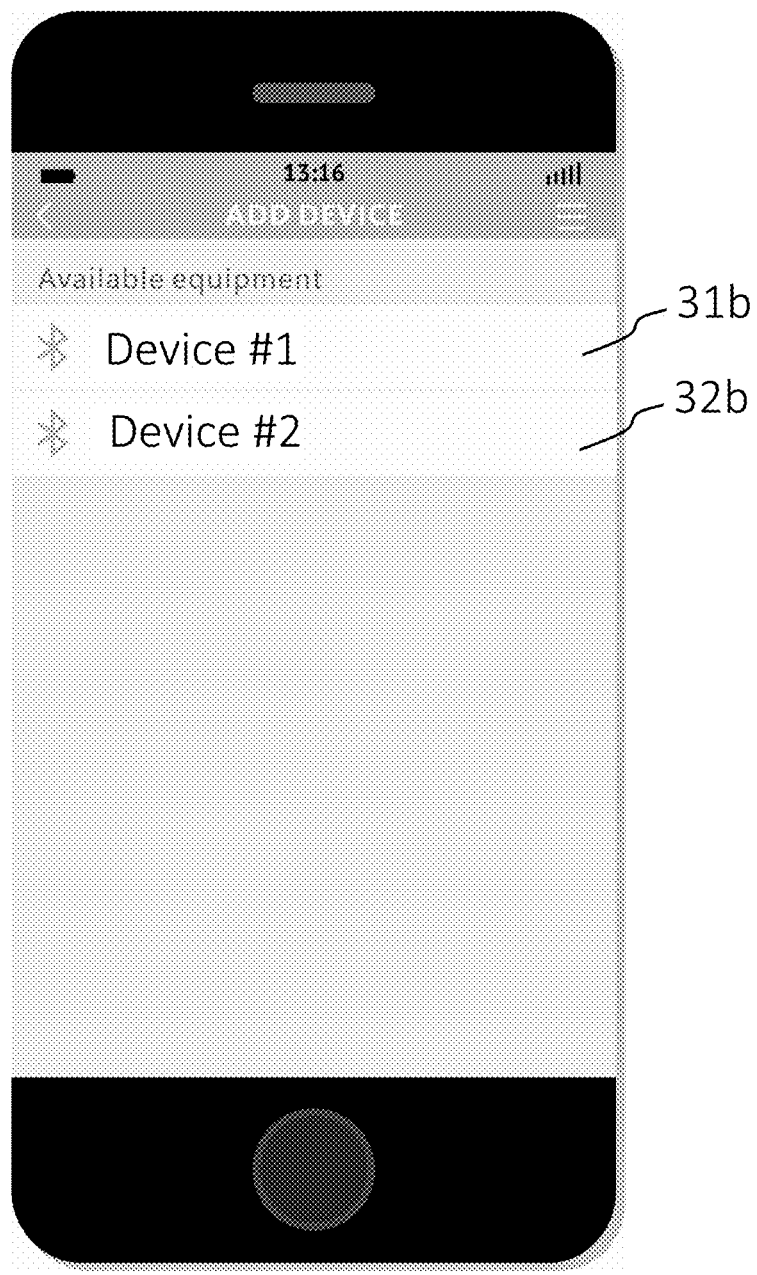
FIG. 61 illustrates an exemplary display user interface of a mobile device.

Exemplary representations for functions are shown in FIG. 60, including representations for Add Device 21b, Manage Devices 22b, Help 23b, and Shopping 24b. The representations will be explained.

By selecting Help 23b, the user may be directed to a forum for communicating questions or looking up questions and answers online. Online chat may be available, as well as direct calling, texting, or other common means of communication by which questions about the device may be answered.

The Shopping 24b selection may directly take the user to an online website where the user may order or purchase additional devices as well as products associated with the device 100.

By selecting the Add Device 21b representation, a display as shown by FIG. 60 illustrates a plurality of devices as shown by Device #1 31b and Device #2 32b. A user then has the option of selecting either device to change the settings for that particular device. Additionally, the user may add or delete a device.

Figure 62:
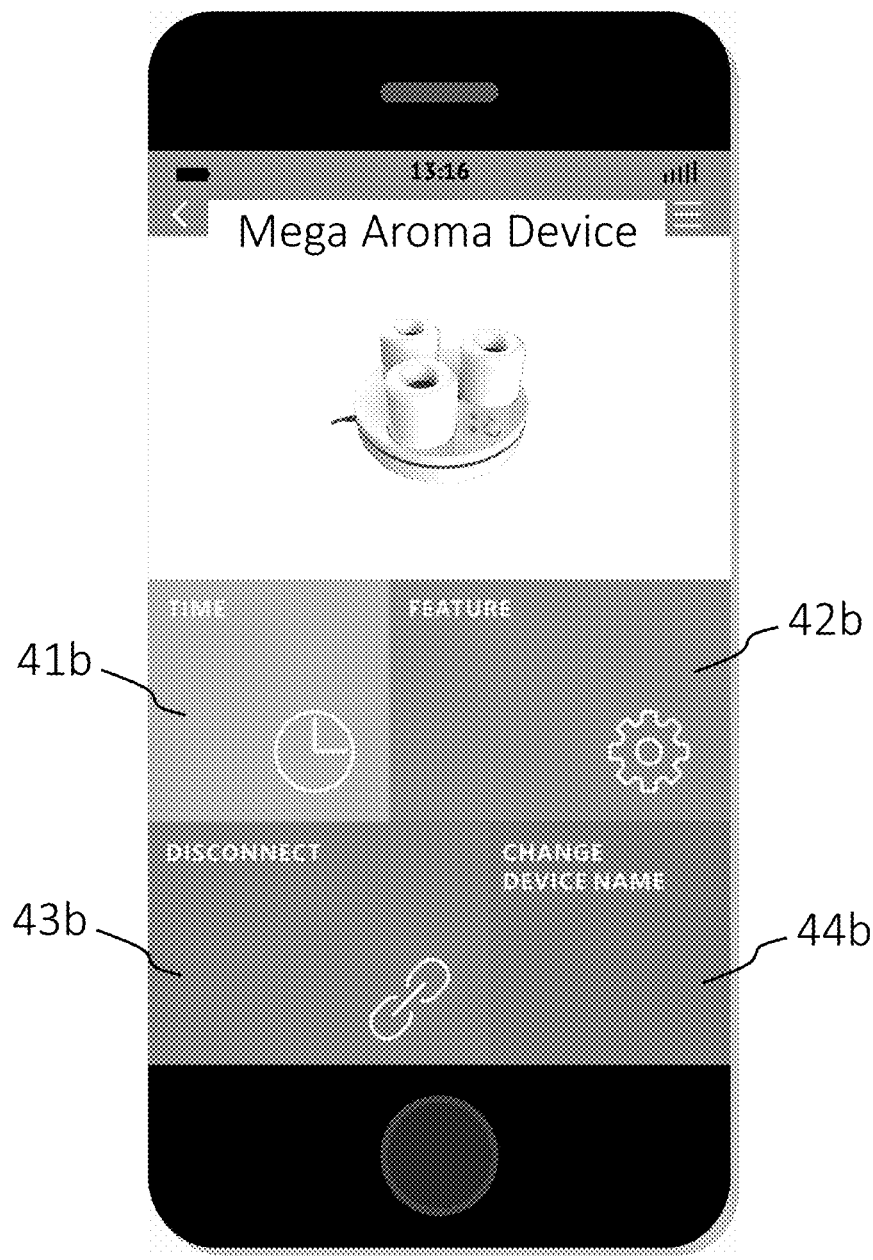
FIG. 62 illustrates an exemplary display user interface of a mobile device.

By selecting the Manage Devices 22b, a display as shown by FIG. 62 may display aspects of the device 100 that may be controlled as shown by various feature representations. Exemplary representations shown include Time 41b, Feature 42b, Disconnect 43b, and Change Device Name 44b are shown in FIG. 62.

After receiving a selection by the user in step 2b, the control module 12b displays a subset of one or more representations or other displays using the display or interface module, which allows the user to make further selections or change settings. Various features may include modules, as shown by Light Feature Module 13b, Feature Module 14b, Device Module 15b, and Time Module 16b. Additional modules are anticipated for various other features.

Figure 63:
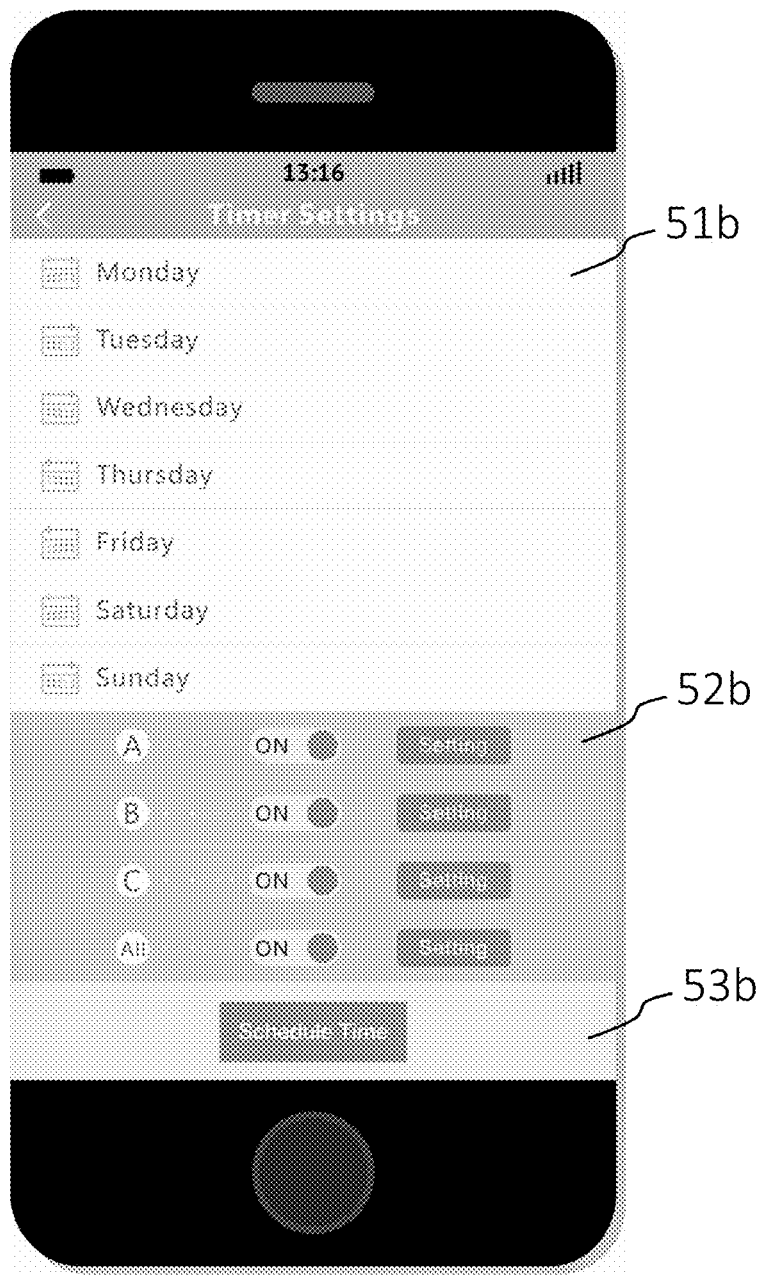
FIG. 63 illustrates an exemplary display user interface of a mobile device.
Figure 64:
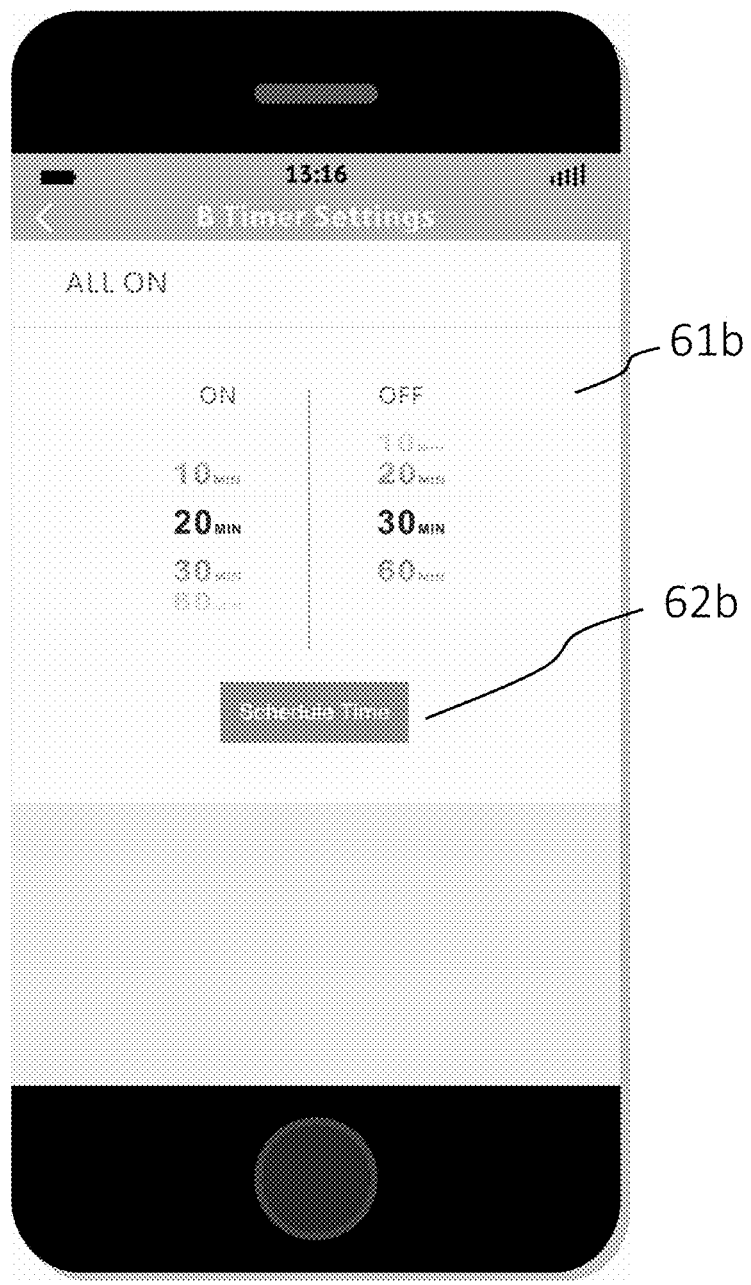
FIG. 64 illustrates an exemplary display user interface of a mobile device.

By selecting Time 41b, the user may be directed to a display like the one shown in FIG. 63. The Calendar days 51b representation allow the user to select a day of the week, month, or year for one time or repeat instances where settings of the device may be defined. For a mega device 400a, A, B, C, and ALL representations 52b include On/Off switches for turning the device on or off, or all the devices, as indicated by the ALL representation, for a selected day.

The setting may further include month, year, and other representations associated with time. Corresponding Setting representations for the selected day allow the user to change specific settings for the device when it is turned on during a particular month, day, or time of day. Schedule time 62b representation allows the time to be set for various features of the device.

Features for the Time 41b that may be controlled include, for example, the timing of the device, such as the length of time that the device is on and/or off. A user may set a plurality of time intervals for a given day for which a feature is on or off. Within the time interval, a user may set another plurality of time intervals for which the feature is on or off. So for example, a user may select the device to be turned on for one hour at morning, lunch, and dinner. Within that hour, the user may select that the device be turned on for five minutes, then off for five minutes. In this way, the device requires little attention during the day.

As shown, a dial representation 61b, depicts a revolving or rotating dial with alternating times that the device is on and off. One dial is for the time on while the other dial is for the time off. In this manner, a user can easily define how long the device should be on and off. The schedule time 62b allows the user to control other time features, such as a specific time of day that the device 100 is to turn on. Also, the timing may further include the time in which the lights are activated.

Figure 65:
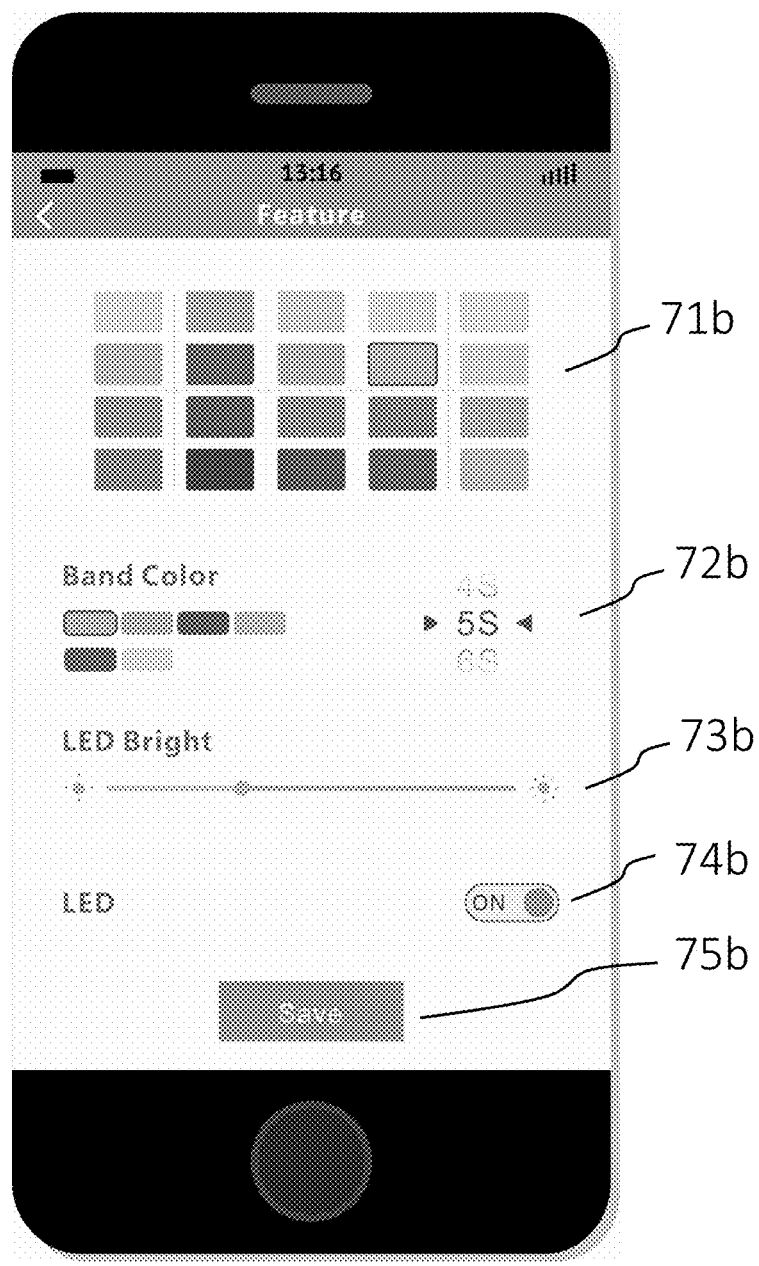
FIG. 65 illustrates an exemplary display user interface of a mobile device.

FIG. 65 depicts controls used to control light as an exemplary control under Feature 42b representation, or a different representation. For example, lighting may be bright during the day, but be dim at night. Light lavender light may be used to indicate a lavender fragrance while a bright lime green may be used to indicate an avocado lime fragrance. Lighting may be controlled by time, or according to fragrance, brightness, fan speed, time of day, charge status, and other purposes that provide additional advantages or serve as visual aids.

As shown in FIG. 65, the Feature 65 includes an array of colors 71b representation in which the user can select at least one or more colors for a light feature of a particular device or plurality of devices. Multiple colors may be used for a particular device or plurality of device and light feature associated with the device or plurality of devices as described herein. Exemplary feature 5S has a plurality colors shown in the Band Colors 72b representation. The dial shown illustrates an exemplary means by which the user selects the feature being controlled and the color for the feature as defined by the user.

Automatic lighting that requires little or no interaction with the user may further be incorporated in the device. Features already discussed herein may be indicated by automatic light.

One or more buttons (e.g., manual input 110 in FIG. 1) on the actual physical device may be programmed so that the device may be manually controlled on the device itself. For example, a button sequence may include holding down the button for three seconds to turn the device off or reset sequences. Another button sequence may include pressing the button three times to activate a 60 minute on/60 minute off repeat cycle. The sequences may be changed remotely over the various external sources described above. The following sequences are exemplary:

Sequence 1—Device is on full time
Sequence 2—Device will alternate on for 60 minutes and off for 60 minutes
Sequence 3—Turns on Bluetooth. When Bluetooth is activated, the fan will stop spinning and the light will blink. A user can now manage the settings from a smart phone.

Other means of control include voice and noise command. Variations include voice prompts initiated by the device or commands initiated by the user with or without a display. For the mega device, the tray may initiate voice prompts and/or receive commands initiated by the user with or without a display. For example, voice recognition may be included such that the device recognizes audible words "on" and "off" and "sequence 1," etc., and activates the associated action to perform.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other non-transitory computer-readable media for carrying or storing computer-executable instructions and/or data structures. Such computer-readable media may be any available media that can be accessed by a general-purpose or special-purpose computer system. Computer-readable media that store computer-executable instructions and/or data are computer storage media. Computer-readable media that carry computer-executable instructions and/or data are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media may include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media may be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, byte code, interpreted code, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

Manufacturing

The refill cartridge 120 is configured to be easily removed and replaced as part of the scent dispersion device (see FIG. 6). The housing 102 of the scent dispersion device allows the refill cartridge to be removed and replaced through the open top of the housing. The cup support of the refill cartridge provides a structure that can be supported in, and easily removed from, the housing. The following describes improvements to manufacturing of the refill cartridge and more generally, a scent delivery system.

A method for making a scented refill cartridge includes making a central axial opening through a solid cylinder made of an absorbent scent retaining material, placing the cylinder within a recess on a platform, pouring liquid fragrance into the central opening to a level that is below a top surface of the cylinder to allow the liquid to be absorbed into the absorbent material, placing the cylinder within a cup support, sealing the top opening with a first removable foil or film; and sealing the bottom opening with a second removable foil or film to seal the cylinder within the interior of the cup support. The scented refill cartridge is configured to be included in a scent dispersion device which includes a housing, fan, and controller, with optional cover that can be decorated.

A system or apparatus for making a scent-absorbed wick includes one or more of a pouring station, sealing station, and labeling station. The pouring station includes a first movable horizontal surface with multiple recesses. Each recess is configured for holding a wick or other absorbent structure. The pouring station further includes a structure for pouring liquid fragrance onto the absorbent structure. Structure is further provided for moving successive recesses in turn into and out of the pouring station.

The stamping station includes a second movable horizontal surface with multiple rows of holders. Each holder is configured for holding a wick, or other volatile or scent absorbent structure, in a cup support stamping station. First structures apply pressure to seal top edges of the cup support and second structures apply pressure to seal bottom edges of the cup support. Further structure is provided for moving multiple rows of holders to move successive rows of holders into and out of first structures, second structures, and stamping station.

The labeling station includes a third horizontal surface that is configured to transport a cup support with wick and one or more coverings. The surface includes multiple holders, each holder configured to hold a cup support, absorbent structure, and one or more coverings. The labeling station includes structure for applying at least one label on the cup support or covering. Structure is also provided for moving each cup support to move successive cup supports in turn into and out of the labeling station.

Figure 66:
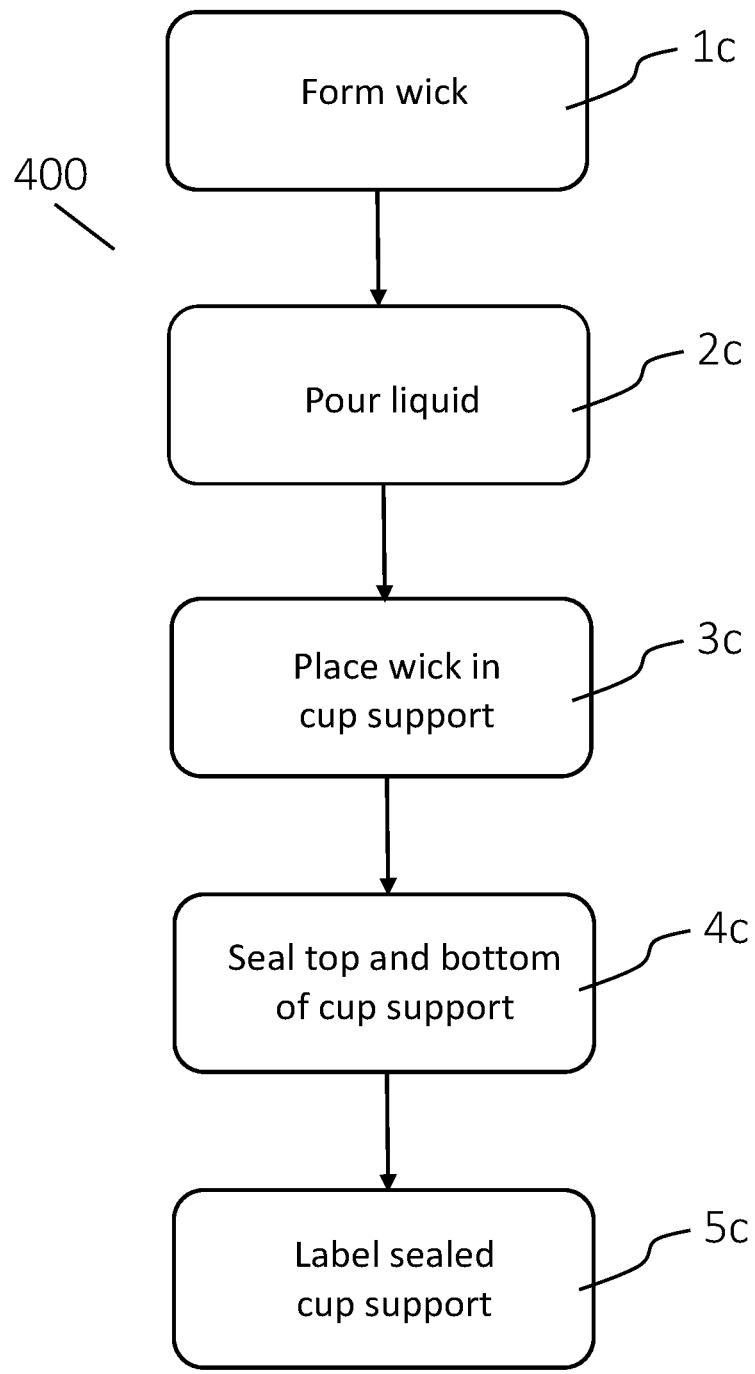
FIG. 66 illustrates a flow chart showing steps used to make a refill cartridge.

When a refill cartridge in the device is spent, it can be replaced with a new one from storage. The seals help prevent the liquid fragrance, or other volatile liquid, from being lost during storage. An example shown in the figures (particularly FIGS. 22 and 23) shows the refill cartridge 120 comprising the cup support 124 with solid vapor impermeable sides and open top and bottom openings (to provide an air path when installed). A flowchart 400 of making a refill cartridge is shown in FIG. 66 and will be discussed in relation to exemplary stations in FIG. 67. The method includes step 1c of forming a wick, a solid porous material in cylindrical form and that may include a hole or central axial opening therethrough, making a hollow cylinder with a concentric circular cross section.

After the wick is formed, liquid is absorbed by the wick in Step 2c. For example, liquid may be poured within the central opening of the wick. Turning to FIG. 68a, a wick 150b is shown next to a platform 144b. The platform 144b includes a platform recess 145b, which is an indented area, or cavity, that is dimensioned to hold the wick 150b. The wick is placed within the recess in FIG. 68b.

The platform recess 145b as shown includes a similar cross-sectional shape as the wick 150b. The platform recess 145b may allow for the wick 150b to be inserted with a friction fit or tight fit. Alternatively, the platform recess 145b may allow for a loose fit with space provided between outer walls of the wick and inner facing walls of the platform recess walls. The recess shown includes a circular cross-section and a depth that is less than half to half the height of the wick height. The height may also be between half the height to the full of the wick height. The height may also be higher than the height of the wick such that the wick is fully contained within the platform recess.

In FIG. 69a, an exemplary pouring structure is shown, including a raised outlet 147b, platform 144b, and wick 150b placed inside platform recess 145b. The raised outlet 147b is configured to communicate liquid fragrance 146b to the wick 150b or to a wick inside a jar or other container.

The raised outlet 147b may be positioned above the wick 150b, at a height measured from the top of the wick that is 0.1 to 0.25 inches, 0.26 to 0.5 inches, 0.6 to 1 inches, or 1.1 to 1.25 inches. The liquid fragrance 146b communicated to the wick may include a metered amount, such as 8 mL, 8.5 mL, 9 mL, 9.5 mL, 10 mL, 10.5 mL, 11 mL, 11.5 mL, 12 mL, 12.5 mL, 13 mL, 13.5 mL, 14 mL, 14.5 mL, 15 mL, 15.5 mL, and 16 mL, but preferably 15 mL. The amount of liquid fragrance 146b will vary in proportion to various factors, including material of the wick, wick dimensions (e.g. height, width, length, diameter, holes or other apertures) temperature, pressure, volatile liquid ingredients, and may therefore be more or less than what is listed.

The liquid fragrance 146b may be communicated by the raised outlet in drops, spurts of liquid, or in one or more continuous streams of liquid. Exemplary rates of liquid flow include 1.1-1.3 mL/s, 1.4 mL/s—1.6 mL/s, 1.7-1.9 mL/s, 2.0-2.2 mL/s and 2.3-2.5 mL/s. The liquid fragrance may be at room temperature, or it may be chilled, heated, or steamed.

After pouring liquid fragrance within the hole of the wick, the method may include waiting for a period of time, such as 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 150-155, 155-160, 160-165, 165-170, 170-175, or 175-180 seconds, or any suitable period of time sufficient to allow the wick to soak up or absorb the liquid fragrance. The waiting period may occur before or after moving the platform away from the raised outlet. Heating or evaporative cooling treatments may be applied as needed or desired. The wick 150b is shown having absorbed liquid fragrance 146b in FIG. 69b.

Figure 67:
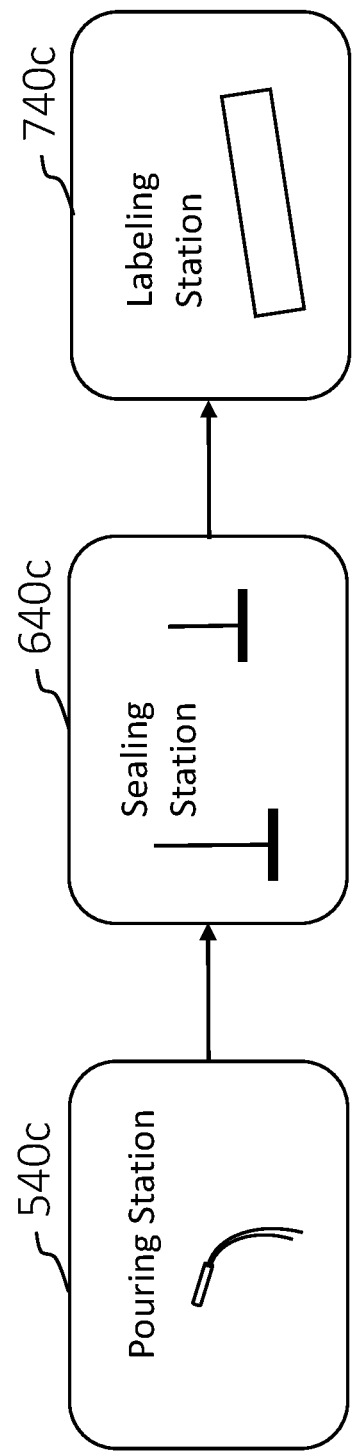
FIG. 67 illustrates exemplary stations used to make a refill cartridge.

For manufacturing purposes, a pouring station 500 indicated in FIG. 67 may be used to pour liquid fragrance into a plurality of wicks.

Figure 70:
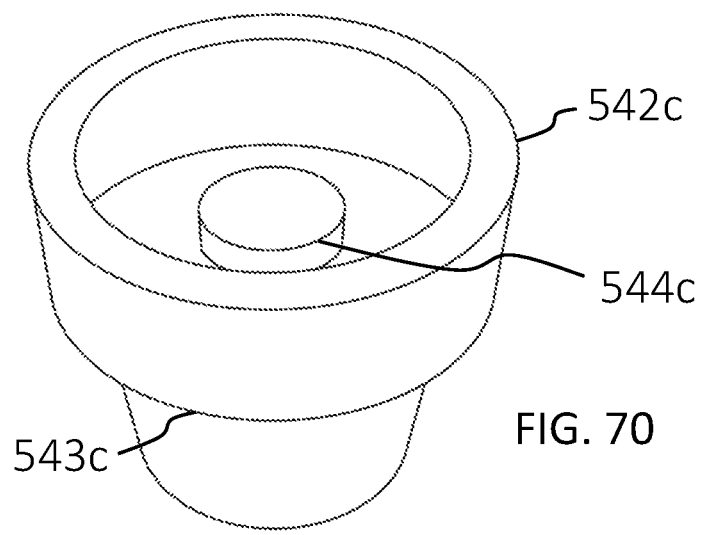
FIG. 70 illustrates a cup holder.

FIG. 70 illustrates a cup holder 542c that may be used for a pouring station. The cup holder 542c includes an open container having a cup-like shape. The exemplary cup holder 542c shown gradually gets narrow at the bottom, but various shapes and sizes of the cup may be used, including a vertical walled cup. The cup holder 542c includes an outer rib 543c, a radially extending ridge on the outer sidewall near or at the top of the cup holder 542c.

Figure 71:
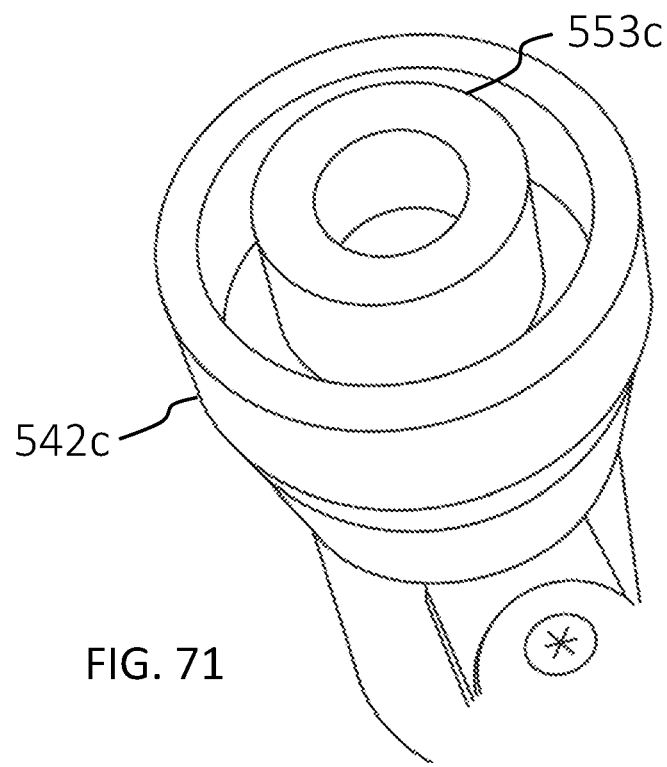
FIG. 71 illustrates an extruded view of a cup holder and a movable horizontal platform.

Within the cup holder 542c is a raised hub 544c having a cylindrical shaped member that extends axially upward from a raised bottom surface 546c of the cup holder 542c. The wick has a central opening that fits around the hub 544c when the wick is placed within the cup holder 542c as shown in FIG. 71. The wick may have a height that is greater than the top of the cup holder 542c, but variations include that the wick may be situated such that the cup and the wick are at a level height with each other.

Figure 72:
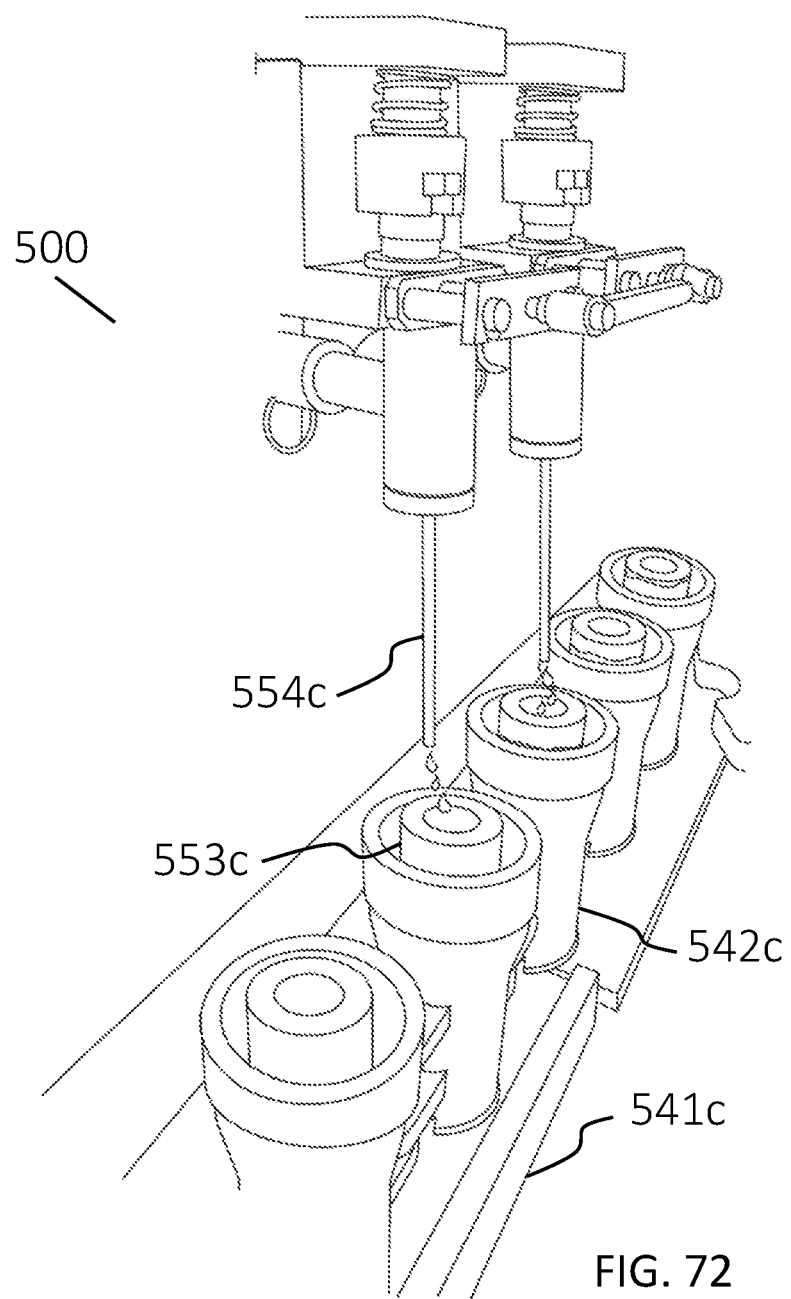
FIG. 72 illustrates a pouring station.

FIG. 72 illustrates a pouring station 500 that includes a movable planar surface 541c with multiple recesses 552c to hold and transport successive wicks 553c to a raised outlet 554c. The act of moving includes moving the platform so that the central axial opening of the wick 553c is directly underneath an outlet 554c that communicates liquid fragrance within the central opening. By pouring the liquid fragrance within the central opening of the wick, there is less surface to absorb through the wick. The hub raises the ground level on which the fragrance is poured which also means that liquid originates above the bottom of the wick. The liquid may originate near the center of the interior of the wick. This enables optimal, efficient distribution of the fragrance within the wick.

If the fragrance were to be distributed on the outside of the wick, fragrance would fill the space between outer walls of the wick and the cup holder, and much of the fragrance would be wasted. The fragrance might not reach an interior of the wick, especially if the wick had a filled center. The hollow interior and pouring of the fragrance within the interior allows less surface to absorb through.

After the liquid fragrance is absorbed within the wick, the following step 3c is to place the wick within the cup support with a central axis of the wick generally aligned with a central axis of the cup support.

The next step 4c is to seal the top and bottom of the cup support. The top and bottom openings during storage are covered with the seal, or in other words, a flexible impermeable material, such as metal foil, polymer film, a combination thereof. A sealing station 640c may be used to join the seal to the support cup.

The height of the wick may be less than the height of the cup support so that a top seal lays flat across the top opening of the cup support. The bottom of the cup support allows a seal to lay flat across the bottom opening of the cup support. Dimensions of the wick may include an outer diameter between 1.00 to 1.25 inches, 1.25 to 1.50 inches, 1.50 to 1.75 inches, and 1.75 to 2.00 inches, an inner diameter between 0.25 to 0.50, 0.50 to 1.00 inch, 1.00 to 1.25 inches, and 1.25 to 1.50 inches, and a height between 0.75 to 1.00 inch, 1.00 inch to 1.25 inches, and 1.25 inches to 2.00 inches. Other dimensions are anticipated.

Figure 73:
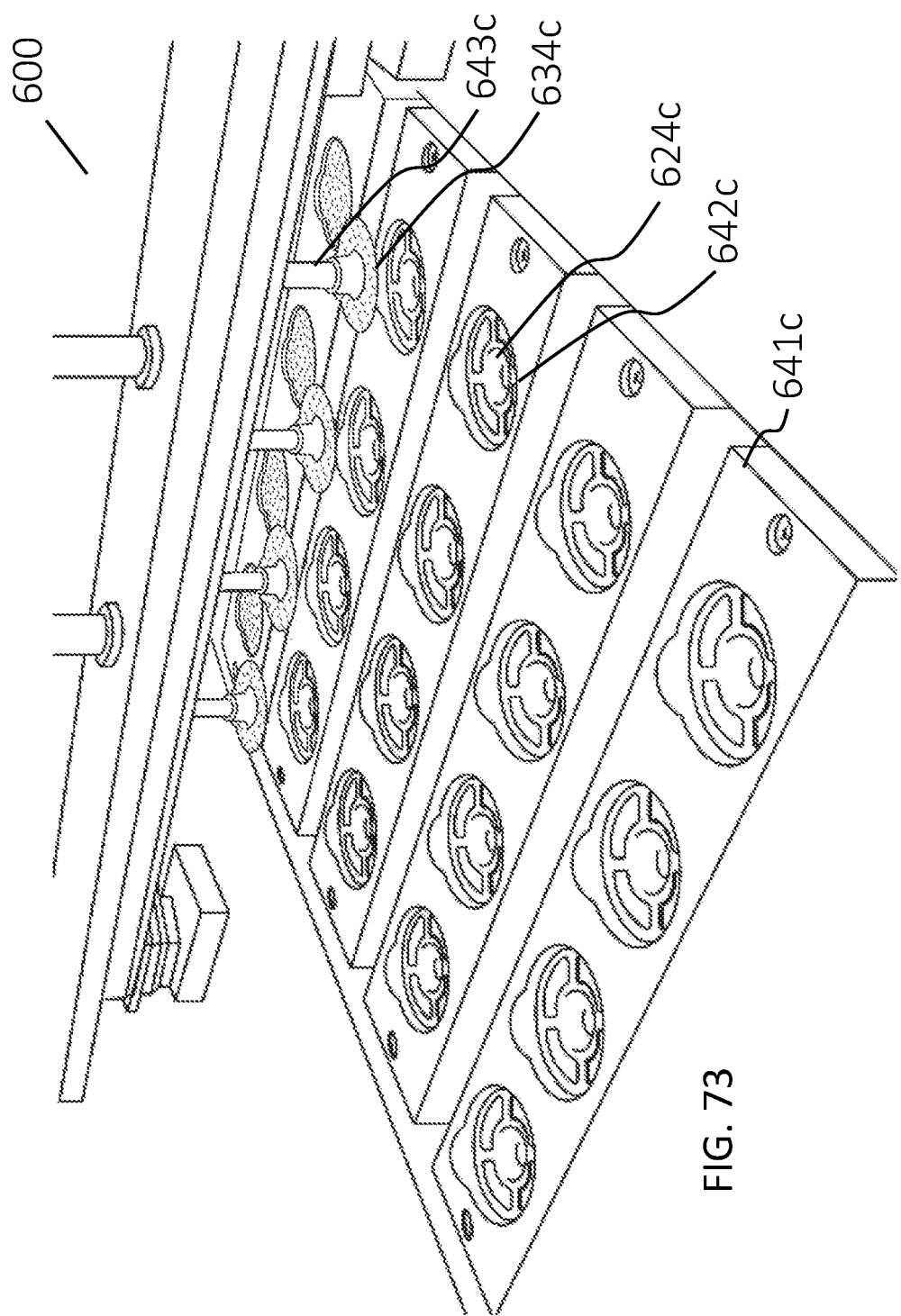
FIG. 73 illustrates an exemplary aspect of a sealing station.
Figure 74:
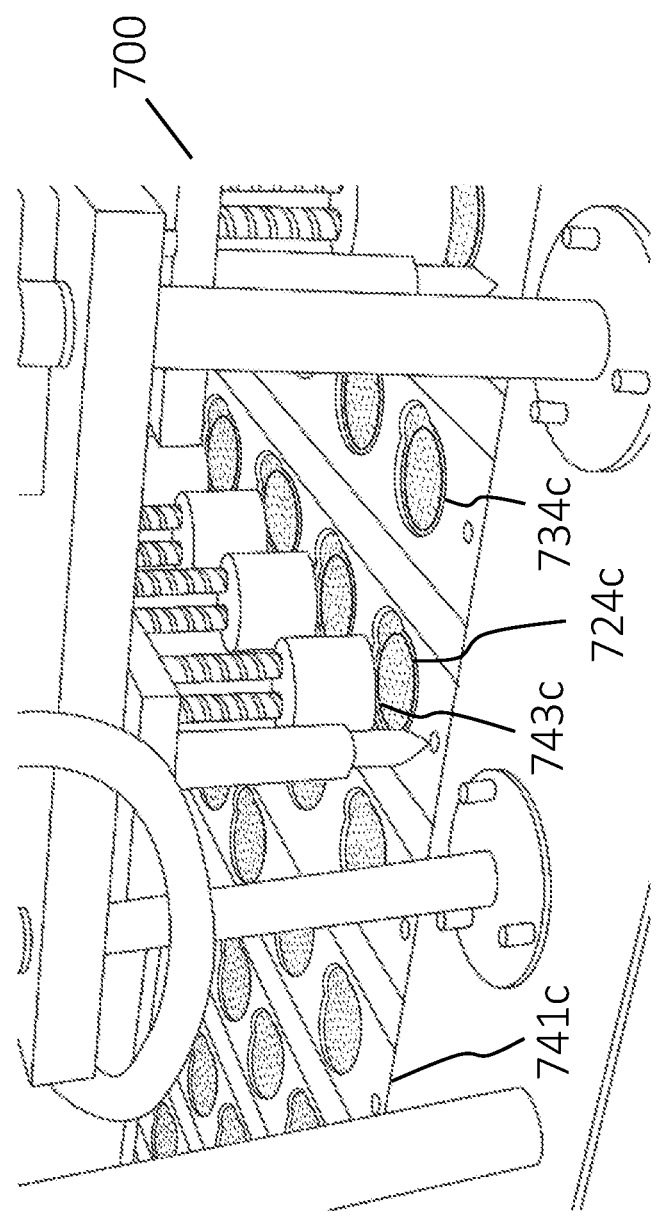
FIG. 74 illustrates an exemplary aspect of a sealing station.
Figure 75:
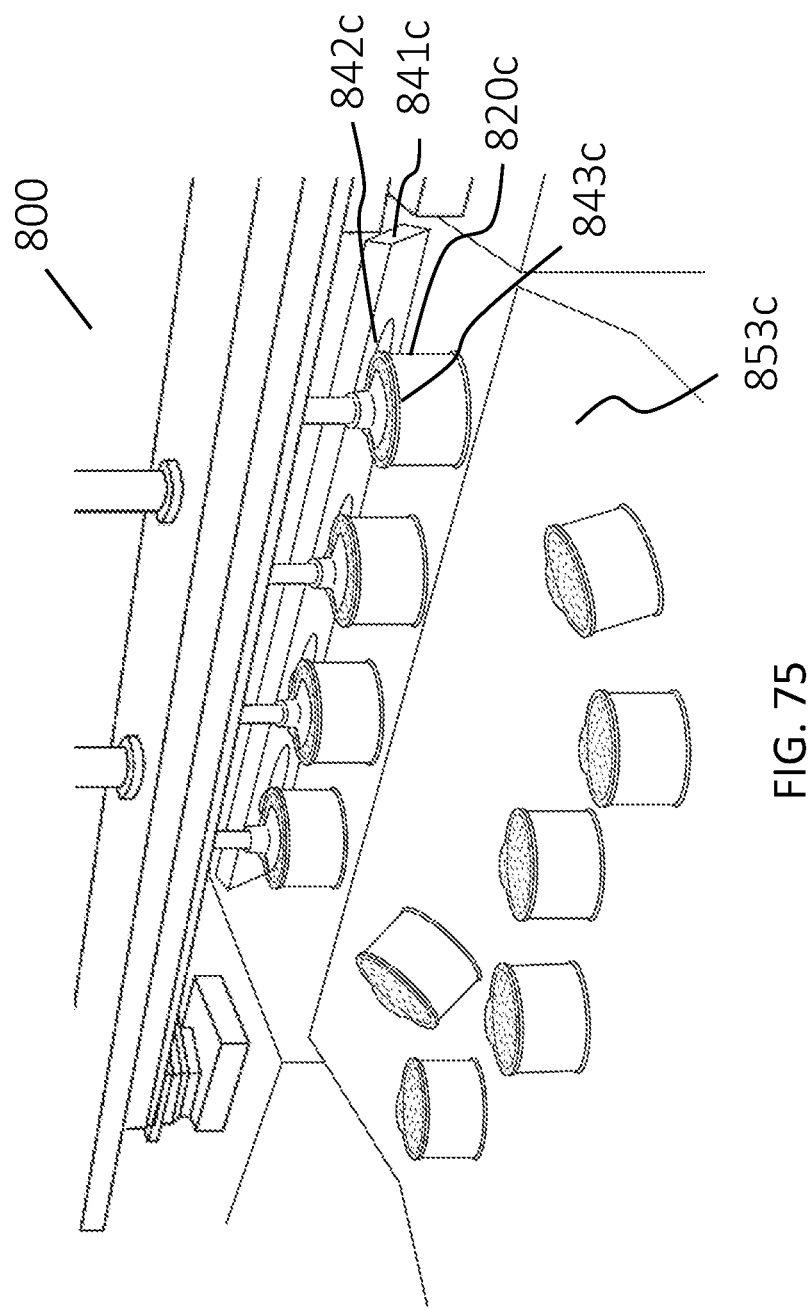
FIG. 75 illustrates an exemplary aspect of a sealing station.
Figure 76:
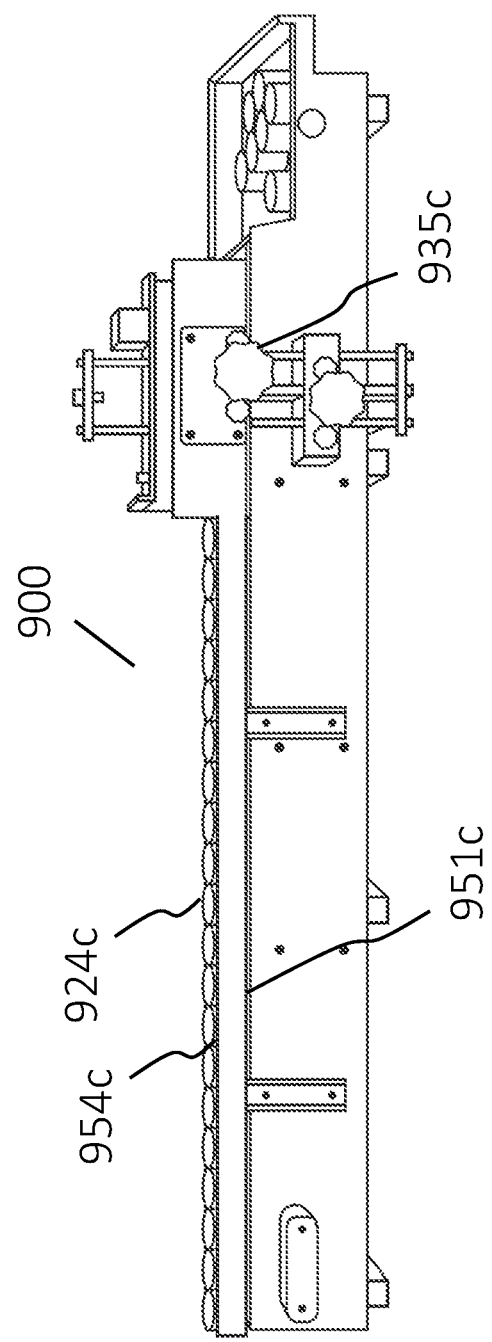
FIG. 76 illustrates a labeling station.

FIGS. 73-75 depict aspects of a sealing station whereby cup supports holding wicks receive seals on top openings and bottom openings. Cup supports holding wicks are transported in rows, each row receiving a first seal and then a second seal.

One aspect of the sealing station may include structure that places a seal on the support cup. As shown in FIG. 600, an exemplary movable planar surface 641c includes rows of holders 642c that are transported in a horizontal manner to a row of suction seal tools 643c. The suction seal tool 643c uses suction to grip a seal 634c and hold it to the suction seal tool 643c. The suction seal tool 643c is configured to force air flows inside an intake structure, such as a nozzle and hose, to create suction. Once the suction seal tool 643c is aligned with respective cup support 624c, a nozzle or other type of end portion of the suction seal tool 643c is lowered vertically downward using pneumatic pressure or other force means. At the end of the nozzle is the seal 634c, which is placed on a top or bottom outer edge of the cup support, depending on which direction the cup support is facing. Once placed over the bottom opening of the cup support 624c, suction ceases and the suction seal tool 643c is raised using the pneumatic pressure or other force means, and the exemplary movable planar surface moves forward such that another row of support cups may receive seals.

Another aspect of the sealing station 640c may be a structure that adheres or otherwise attaches the seal to the support cup. As shown in FIG. 700, an exemplary movable planar surface 741c includes cup supports in rows of holders 742c that are transported in a horizontal manner to a row of stamping tools 743c whereby each cup support in a row receives simultaneous pressure by top stamping tools 343b. Each stamping tool 743c includes a rounded, circular end piece, or cylindrical end piece with a hollowed center and that is the same or a similar diameter as the cup support. The cylindrical end piece is also heated. The stamping tool includes an open position where the end piece is raised above the cup support and a closed position where the structure contacts outer edges of the cup support and applies pressure to seal top seals to outer edges of the cup supports.

Once the bottom stamping tool 743c is aligned with respective cup support 724c, the cylindrical end piece is lowered vertically downward using pneumatic pressure or other force means to contact the seal and apply pressure. The heat and pressure make the seal 734c adhere to edges of the top or bottom of the cup support, depending on which direction the cup support is facing. Pressure may further be distributed to other areas on top of cup supports. After stamping the seal on to the cup support to seal off the edges of the opening of the cup support, the bottom stamping tool moves vertically upward using the pneumatic pressure or other force means, and the exemplary movable planar surface moves forward such that another row of support cups may be sealed.

While the bottom side of the support cups is shown, the top side is treated in a similar manner. Another aspect of the sealing station includes rotating the support cups to their opposite facing side such that their opposite facing sides receive seals, and are sealed with a pressurized heat treatment in the same manner as the side with seals.

In an alternative configuration, instead of the upper rims of the cup supports facing the top structures, the cup supports may be face down, with the upper rims facing downward. The seals are placed underneath the cup supports, such that the structures place pressure directly on the bottom of the cup supports with the seals underneath the cup supports. This configuration seals the upper rims of the cup supports to the top seals. Alternatives further include the use of a removable adhesive to seal the cup supports.

In another aspect of the sealing station, a structure may serve to remove sealed cartridges from the holders. As shown in FIG. 800, an exemplary movable planar surface 841c includes rows of holders 842c that are transported in a horizontal manner to a row of removal suction tools 843c. The removal suction tool 843c uses suction to grip a cartridge 820c and hold it to the removal suction tool 843c. The removal suction tool 843c is configured to force air flows inside an intake structure, such as a nozzle and hose, to create suction. It may be the same or similar in structure and function as the suction seal tool 643c. Once the removal suction tool 843c is aligned with a respective cup support 824c, a nozzle or other type of end portion of the removal suction tool 843c vertically lowers downward using pneumatic pressure or other force means. The nozzle contacts the cartridges and applies suction to grip the cartridge. The nozzle is then held constant or raised vertically upward as the movable planar surface is revolves or otherwise moves away from the cartridge. The nozzle maintains a hold on the cartridge until the planar surface is substantially or completely removed away from the cartridge. Then, the removal suction tool 843c stops applying suction to release the cartridge on to an exit ramp 853c or other second surface. In this manner, the cartridge is removed from the sealing station.

The station, or stations, that are used to seal the cup support, may vary in the order of sealing. For example, the bottom seals may be applied first, followed by the top seals. Alternatively, the top seals may be applied first, followed by the bottom seals.

A time delay between top and bottom sealing is 65-70 s, 70-75 s, 75-80 s, 80-85 s, 85-90 s, 90-95 s, 95-100 s, 100-105 s, or 105-110 s, more preferably 95-100 s. The time between two sealers on one machine is 1 s, 2 s, 3 s, 4 s, 5 s, 6 s, more preferably 4 s. Note that the cup supports are made of PET plastic, or of a like material that provides that liquid fragrance does not escape once the sealing process is completed and the refill cartridges are stored.

A final step 5c is to label the cup support at a labeling station 740c. FIG. 900 depicts a labeling station which includes a movable horizontal surface 951c that is configured to transport a cup support 924c with wick and one or more seals, the surface 951c including multiple holders 954c for holding cup supports 924c. The holders 954c may be in rows or in a single file. The labeling station includes a labeling wrapper structure 935c for applying at least one label around outer sidewalls each cup support 954c. The labeling wrapper structure may comprise a rotating mechanism that rotates the cup support 924c so that a label is wrapped arounds its outer side walls. Labels may also or alternatively be applied on the top or bottom of the cup support and seals. Structure is further included for moving each cup support to move successive cup supports in turn into and out of the labeling station. Other known means of applying labels are also anticipated.

While the manufacturing process may be divided into separate stations, it is contemplated that one or more of the stations be joined. One or more of a continuous transport, conveyer belt system, rotation mechanisms, rotating discs, ramps or other lifting and lowering mechanisms may be used. Variations further include that stations be divided into sub-stations, and additional stations are anticipated. The stations may be fully or partially automated and programmed to work in sync with each other. Manual labor may also be included for one or more actions described herein. Variation While the wick has been described as a hollowed cylinder, other shapes are anticipated. For example, a torus or donut shape is possible. Outer sidewalls may have pointed extensions, for example, so as to define an outer star shape. This shape, or another shape may be used to maximize surface area for airflow. The wick may be of any logical shape.

Openings in the wick may be offset, angled, or at a 90 degree angle to the axial direction of the shape. Instead of one hole, there may be multiple holes, apertures, bumps, recesses, and other features. The material may be non-porous, but have holes. Also, there may be no hole whatsoever. The edges of the wick may be generally curved or alternatively, the edges may have one or more curves and undulations that allow for desired air flow.

Seals for the refill cartridge may be replaced by lids, such as plastic lids that are of the same material as the cup support. One or more of a top and bottom lid may twist, snap, or otherwise attach to the cup support. Variations of the refill cartridge include no seals sealed to the cartridge. Storage in such cases are accomplished through means that include no seals.

Reference is made to figures of the aroma device and a refill cartridge, which are exemplary and are not limiting to the scope of the invention. Referring to FIGS. 16-29, which show various examples of the aroma device and features of the device, the device comprises a housing which contains a refill cartridge, and a fan. The housing shown is generally cylindrical and vertically aligned to provide an upward air path through the housing. The fan draws air through openings at or near the bottom of the housing and forces the air upward through the interior of the housing. The openings are below the fan, and can be of any suitable configuration, including any one of or more of openings in the bottom of the housing, slots on the side, and the like.

The fan is powered by a battery and is controlled by a controller. The battery and controller are contained in the housing at any suitable location, such as below the fan in a position to not block the air flow.

The battery may be any suitable battery. A rechargeable battery is suitable and may include within the housing recharging circuits. The recharging circuit may include a plug in the housing for a charging jack, or a wireless inductive charging system.

The controller controls the fan. In addition to turning the fan on or off, the controller may also control the fan speed. The controller may include settings so that the device turns on at intervals of time, for example, every 30 minutes, every 60 minutes, or every 90 minutes. The controller also provides the interface with the user by any suitable system including wireless communication, such as Wi-Fi or Bluetooth. This can be in conjunction with an app on a cell phone or tablet, or with a dedicated user interface. With wireless communication, the controller may be in communication with any suitable device to provide data or user input. For example, sensors (motion, chemical, particle, temperature, moisture, etc.) may be provided to signal an event or condition. The controller may be programmable to determine operation of the fan based upon sensor and user inputs, and the time.

Other electronic elements such as lights, sound generators, sensors, and the like may be incorporated into the device and be associated with the controller. For example, lights may indicate whether the device is turned on or off.

The fan directs air upward through a refill cartridge. The refill cartridge is placed above the fan in the housing. Directly above the fan or as close as practical to the fan is a suitable location. As described above, the refill cartridge contains a wick, or a solid porous material, or some other saturated fiber core, capable of carrying or absorbing a volatile liquid scent or aroma that can be desorbed or vaporized into air passing through the refill cartridge.

Structure may be included to direct air into the holes or to diffuse evaporated scent into the air stream, such as the streamline narrowing stream constrictor shown at the bottom of cup in FIGS. 3 and 20.

The device comprising the housing, fan, battery, controller, and refill cartridge is a standalone fully functional system for introducing scent into the air. However, advantages can be derived by addition of an outer cover. The outer cover fits over the outer surface of housing such that it can be easily installed and removed. A suitable configuration is a cylindrical cover that slidably fits over the housing. The outer cover has a vent to provide an air path to the outside for air blown up by the fan through the refill cartridge. The vent may also include components to mix or direct the scented are from the device.

Air flow up through and exiting the cover can be improved by shaping or streamlining the interior. This can be accomplished by molding a shaped interior during molding of the cover. Alternately, as shown in FIG. 24, an insert ring may be provided.

The interior of the cover has to be dimensioned to fit over the housing as described, but the exterior may be plain as shown in FIG. 16, or the exterior may have the form including any of several decorative elements, such as a sculpture, candle holder, model, or the like. Examples of decorative elements are shown in FIG. 25 and FIG. 26.

The volatile liquid scent can be any suitable diluted or undiluted oil or water based scent material in the liquid state that volatizes into vapor in air. This includes scented oils, essential oils, and any suitable fragrance composition. In suitable applications, odoriferous and stinky materials are contemplated. Also contemplated are volatile materials that have a medicinal, biological, or like application, and are to be dispersed into the air. The device does not include a heater to volatize the liquid, so suitable materials are those that vaporize or evaporate sufficiently in the fan directed air stream without heating.

The components of the device may be constructed by any suitable method, such any one of or a combination of molding, milling, machining, bending, stamping, cutting or the like.

The components may be manufactured of any suitable material which includes any one or a combination or composite of thermosetting or thermoplastic polymers that are synthetic or natural (polyethylene, polypropylene, nylon, etc.), or metals (aluminum, steel, etc.).

The combination of components as described allows for advantages not found in previous devices. The device is standalone since it is battery powered, and wirelessly controlled and regulated.

The vaporization of the scent is assisted by the air flow, and not by a heater. Air flow is optimized by providing a straight upward vertical air flow up through and out of the device, with streamlining and construction to minimize friction and impediments to the airflow. Instead of increasing airflow with a larger fan, air flow is optimized by this streamlining, allowing a relatively low power consumption of the fan while maintaining a large airflow.

In tests of an exemplary prototype an air flow as high as 2.2 meters per second measured by anemometer near the exit was obtained. Due to the inner wall design directing air flow out the top opening, the device almost works like a blow gun. Despite a relatively small size of the device, the fragrance/room coverage is quite significant. It is expected that a higher air flow and air speed can be obtained by optimizing the design and increasing the size of the device.

The controller for the device or the tray is programmable and can incorporate almost any suitable function for operating the fan and any optional LED light and other added components. With wireless communication combined with a user interface and any number of various devices, the fan can be regulated based upon time, environmental conditions, preset settings, and communications from the user. This allows the operation of the device to be efficient and power saving.

Accordingly, the battery can last long due to low power consumption, by efficient control of the fan operation by the controller. In addition, the fan is efficient and the air path is designed for efficiency lowering power consumption. Further, the present device does not require a heater, which is power hungry and inefficient for dispersing materials into the air.

The device is fully operable without or with the cover. With cover the device can be interchangeably decorated to any configuration. Appearance can be most anything and can be interchanged easily with a new totally different appearance.

The device can operate for a long time without intervention or maintenance due to the long battery life, and the potentially large capacity of the refill cartridge, which is only limited by dimensions of the device.

The device is easily maintained. Assembly and disassembly for maintenance, refill cartridge replacement, change of outer cover, can be accomplished by sliding components and locking components without the used or tools or other like assists.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for making a scented refill cartridge, the method comprising:
    providing a wick with a central axial opening therethrough, the wick having an absorbent scent-retaining material;
    placing the wick within a recess on a platform;
    pouring liquid fragrance into the central opening to a level that is below a top surface of the wick to allow the liquid to be absorbed into the absorbent material;
    placing the wick within a cup support, the cup having an interior, a top opening, and a bottom opening;
    sealing one or more of the top opening and bottom opening with a covering to seal the wick within the interior of the cup.

2. The method of claim 1, wherein the covering includes a removable foil or film.

3. The method of claim 1, further comprising an act of moving the platform so that the central axial opening of the wick is directly underneath an outlet that communicates liquid fragrance.

4. The method of claim 1, wherein the liquid fragrance is at room temperature.

5. The method of claim 1, wherein the liquid fragrance is metered.

6. The method of claim 1, further comprising between the pouring step and the placing step, further comprising steps of waiting for a period of time.

7. The method of claim 1, wherein the cup includes an inner ridge for supporting the wick within the interior of the cup.

8. The method of claim 1, wherein the recess is dimensioned such that it provides a friction fit with the wick.

9. The method of claim 1, wherein the recess includes a circular cross-section and a depth that is less than half to half the height of the wick.

10. The method of claim 3, wherein placing the wick within the cup further includes an act of aligning the wick on the inner ridge so that the inner ridge only partially covers a bottom surface of the wick and the bottom surface of the wick is at least partially exposed through the bottom opening of the cup, providing air pathways to communicate with the bottom surface of the wick.

11. The method of claim 1, wherein placing the wick within the cup further includes an act of centering the cylinder between inner walls of the cup and thus defining air pathways between the inner walls of the cup and outer walls of the cylinder for air to flow from the bottom opening of the cup to the top opening of the cup.

12. The method of claim 1, wherein pouring occurs at a pouring station and the method further comprises steps of:
    moving the platform along a horizontal plane to move the wick from the pouring station and to move a second wick to the pouring station so that a second wick on the platform may receive liquid fragrance, and
    pouring liquid fragrance into a central opening of the second wick.

13. The method of claim 1, wherein placing the wick within the cup further includes an act of positioning the wick so that the wick may form a concentric configuration with a fan to communicate air through the cup.

14. The method of claim 1, wherein the wick, when placed within the cup, rests below the top opening of the cup and above the bottom opening of the cup.

15. An apparatus for making a scent-absorbed wick comprising:
    a first movable horizontal surface,
    multiple recesses in the first movable surface, each recess for holding an absorbent structure with at least one hole or opening,
    a pouring station, including structure for pouring liquid fragrance into the at least one hole or opening when a recess with an absorbent structure is at the pouring station,
    structure for moving the recess to move successive recesses in turn into and out of the pouring station.

16. The apparatus of claim 15, further comprising:
    a second movable horizontal surface, multiple rows of holders in the second movable surface, each holder for holding the absorbent structure in a cup support stamping station, including first structures for applying pressure to seal top edges of the cup support and second structures for applying pressure to seal bottom edges of the cup support,
    structure for moving the multiple rows of holders to move successive rows of holders into and out of the first structures, second structures, and stamping station.

17. The apparatus of claim 15, wherein the first movable horizontal surface includes a belt, or a rotating disc, that is configured to transport scent-absorbed solid wicks into and out of the pouring station.

18. The apparatus of claim 16, wherein the second movable horizontal surface includes a belt, or rotating disc, that is configured to transport rows of holders of cup supports with scent-absorbed wicks into and out of the first structures, second structures, and stamping station.

19. The apparatus of claim 16, wherein the pressure for sealing the bottom edges and the top edges includes a first hydraulic actuator that actuates a facing to press against the bottom edges of the cup support and a second hydraulic actuator that actuates a facing to press against the top edges of the cup support.

20. The apparatus of claim 15, further comprising:
    a third horizontal surface that is configured to transport a cup support with wick and one or more coverings, the surface including multiple holders,
    a labeling station, including structure for applying at least one label on the cup support or covering,
    structure for moving each cup support to move successive cup supports in turn into and out of the labeling station.

* * * * *